(12) United States Patent
Menzel

(10) Patent No.: US 7,087,415 B2
(45) Date of Patent: Aug. 8, 2006

(54) METHODS AND COMPOSITIONS FOR DIRECTED GENE ASSEMBLY

(75) Inventor: Rolf Menzel, Lincoln University, PA (US)

(73) Assignee: Athena Biotechnologies, Inc., Newark, DE (US)

( * ) Notice: Subject to any disclaimer, the term of this patent is extended or adjusted under 35 U.S.C. 154(b) by 338 days.

(21) Appl. No.: 09/920,118

(22) Filed: Jul. 31, 2001

(65) Prior Publication Data

US 2002/0102734 A1 Aug. 1, 2002

Related U.S. Application Data

(60) Provisional application No. 60/222,139, filed on Jul. 31, 2000.

(51) Int. Cl.
C12N 15/64 (2006.01)
C12Q 1/68 (2006.01)
C12P 19/34 (2006.01)

(52) U.S. Cl. .................. 435/91.4; 435/6; 435/91.1

(58) Field of Classification Search ............... 435/91.4, 435/91.1, 320.1, 455, 471, 252.3, 235.1, 435/325; 536/23.1, 24.1
See application file for complete search history.

(56) References Cited

U.S. PATENT DOCUMENTS

| | | | |
|---|---|---|---|
| 4,760,025 A | 7/1988 | Estell et al. | |
| 4,914,031 A | 4/1990 | Zukowski et al. | |
| 4,980,288 A | 12/1990 | Bryan et al. | |
| 4,990,452 A | 2/1991 | Bryan et al. | |
| 5,093,257 A | 3/1992 | Gray | |
| 5,155,033 A | 10/1992 | Estell et al. | |
| 5,182,204 A | 1/1993 | Estell et al. | |
| 5,185,258 A | 2/1993 | Caldwell et al. | |
| 5,204,015 A | 4/1993 | Caldwell et al. | |
| 5,310,675 A | 5/1994 | Estell et al. | |
| 5,316,935 A | 5/1994 | Arnold et al. | |
| 5,316,941 A | 5/1994 | Estell et al. | |
| 5,340,735 A | 8/1994 | Christianson et al. | |
| 5,346,823 A | 9/1994 | Estell et al. | |
| 5,397,705 A | 3/1995 | Zukowski et al. | |
| 5,399,283 A | 3/1995 | Stabinsky et al. | |
| 5,441,882 A | 8/1995 | Estell et al. | |
| 5,500,364 A | 3/1996 | Christianson et al. | |
| 5,521,077 A | 5/1996 | Khosla et al. | |
| 5,605,793 A | 2/1997 | Stemmer | |
| 5,631,217 A | 5/1997 | Branner et al. | |
| 5,665,587 A | 9/1997 | Aaslyng et al. | |
| 5,674,833 A | 10/1997 | Mikkelsen et al. | |
| 5,700,676 A | 12/1997 | Bott et al. | |
| 5,723,323 A | 3/1998 | Kauffman et al. | |
| 5,763,192 A | 6/1998 | Kauffman et al. | |
| 5,763,257 A | 6/1998 | Bott et al. | |
| 5,801,038 A | 9/1998 | Bott et al. | |
| 5,811,238 A | 9/1998 | Stemmer et al. | |
| 5,814,476 A | 9/1998 | Kauffman et al. | |
| 5,817,483 A | 10/1998 | Kauffman et al. | |
| 5,824,514 A | 10/1998 | Kauffman et al. | |
| 5,830,696 A | 11/1998 | Short | |
| 5,830,721 A | 11/1998 | Stemmer et al. | |
| 5,837,458 A | 11/1998 | Minshull et al. | |
| 5,888,732 A * | 3/1999 | Hartley et al. | ................. 435/6 |
| 5,939,250 A | 8/1999 | Short | |
| 5,955,340 A | 9/1999 | Bott et al. | |
| 5,958,672 A | 9/1999 | Short | |
| 5,965,408 A | 10/1999 | Short | |
| 5,972,682 A | 10/1999 | Bott et al. | |
| 5,976,862 A | 11/1999 | Kauffman et al. | |
| 5,985,598 A * | 11/1999 | Russo et al. | ............... 435/69.1 |
| 6,004,788 A | 12/1999 | Short | |
| 6,030,779 A | 2/2000 | Short | |
| 6,054,267 A | 4/2000 | Short | |
| 6,057,103 A | 5/2000 | Short | |
| 6,096,548 A | 8/2000 | Stemmer | |
| 6,117,679 A | 9/2000 | Stemmer | |

FOREIGN PATENT DOCUMENTS

| | | |
|---|---|---|
| WO | WO 93/19172 | 9/1993 |
| WO | WO 95/22625 | 8/1995 |
| WO | WO 97/07205 | 2/1997 |
| WO | WO 98/27230 | 6/1998 |
| WO | WO 98/31837 | 7/1998 |
| WO | WO 98/42728 | 10/1998 |
| WO | WO 98/42832 | 10/1998 |
| WO | WO 99/23107 | 5/1999 |

(Continued)

OTHER PUBLICATIONS

Lodish H, Berk A, Zipursky SL, Matsudaira P, Baltimore D, Dar J, Molecular Cell Biology, Fourth Edition, 2000, W.H. Freeman and Company, New York, pp. 488-489.*

(Continued)

Primary Examiner—Ram R. Shukla
Assistant Examiner—Patrick S. Riggins
(74) Attorney, Agent, or Firm—Drinker Biddle & Reath, LLP

(57) ABSTRACT

The present invention is directed to methods and compositions for use of homologous recombination for directed evolution, gene reassembly, and directed mutagenesis. One aspect of the present invention relates to methods for use of bacterial conjugative transfer and homologous recombination for directed evolution, gene reassembly, and directed mutagenesis. Another aspect of the present invention relates to compositions for use in or produced by the methods of the present invention, including libraries, archives and databases.

54 Claims, 26 Drawing Sheets

FOREIGN PATENT DOCUMENTS

Figure 1:
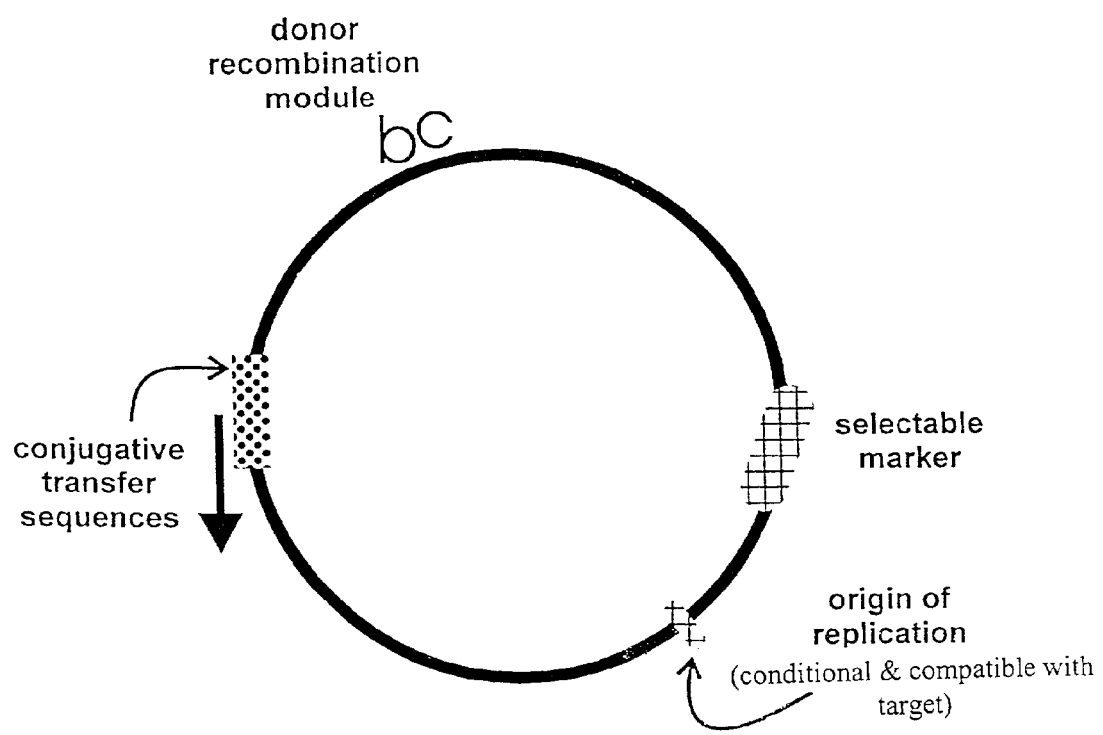

| | | |
|---|---|---|
| WO | WO 99/29902 | 6/1999 |
| WO | WO 99/65927 | 12/1999 |
| WO | WO 00/09682 | 2/2000 |
| WO | WO 00/09727 | 2/2000 |
| WO | WO 00/18906 | 4/2000 |
| WO | WO 00/20573 | 4/2000 |
| WO | WO 00/28008 | 5/2000 |
| WO | WO 00/28017 | 5/2000 |
| WO | WO 00/28018 | 5/2000 |
| WO | WO 00/288018 | 5/2000 |

OTHER PUBLICATIONS

Chang et al., 1999, "Evolution of a cytokine using DNA family shuffling", Nature Biotechnol. 17:793-797.

Crameri et al., 1998, "DNA shuffling of a family of genes from diverse species accelerates directed evolution", Nature 391:288-291.

Evens and Wichter, 1993, "Biotechnology: an introduction to recombinant DNA technology and product availability", Ther. Drug Monit. 15:514-520.

Kobayashi and Inouye, 1992, "Functional analysis of a chaperone: mutational hot spots in the subtilisin propeptide and a second site suppressor mutation within the subtilisin molecule", J. Mol. Biol. 226:931-933.

Kuchner and Arnold, 1997, "Directed evolution of enzyme catalysts", Trends Biotechnol. 12:523-530.

LeBlanc et al., 1998, "Genetic transfer methods for *Streptococcus sobrinus* and other oral streptococci", Meth. Cell Sci. 20:85-93.

Li et al., 1995, "Functional analysis of the propeptide of subtilisin E as an intramolecular chaperone for protein folding. Refolding and inhibitory abilities of propeptide mutants", J. Biol. Chem 270:25127-25132.

Manganelli, 1998, "Insertion vectors for construction of recombinant conjugative transposons in *Bacillus subtilis* and *Enterococcus faecalis*", FEMS Microbiol. 168:259-268.

Marrs et al., 1999, "Novel approaches for discovering industrial enzymes", Curr. Opin. Microbiol. 2:241-245.

Oliphant et al., 1986, "Cloning of random-sequence oligodeoxynucleotides", Gene 44:177-183.

Piotukh et al., 1992, "Design of hybrid metalloprotcinases from Bacillus", Molekulyarnaya. Biologiya 26:601-604 (in Russian with English abstract).

Pompon and Nicolas, 1989, "Protein engineering by cDNA recombination in yeasts: shuffling of mammalian cytochromeP-450 functions", Gene 83:15-24.

Stemmer, 1994, "Rapid evolution of a protein *in vitro* by DNA shuffling", Nature 370:389-391.

Stemmer, 1994, "DNA shuffling by random fragmentation and reassembly: *In vitro* recombination for molecular evolution", Proc. Natl. Acad. Sci. USA 91:10747-10751.

Thykjaer et al., 1997, "Gene targeting approaches using positive-negative selection and large flanking regions", Plant Mol. Biol. 35:523-530.

Wackett, 1998, "Directed evolution of new enzymes and pathways for environmental biocatalysis", Ann. NY Acad. Sci. 864:142-152.

* cited by examiner

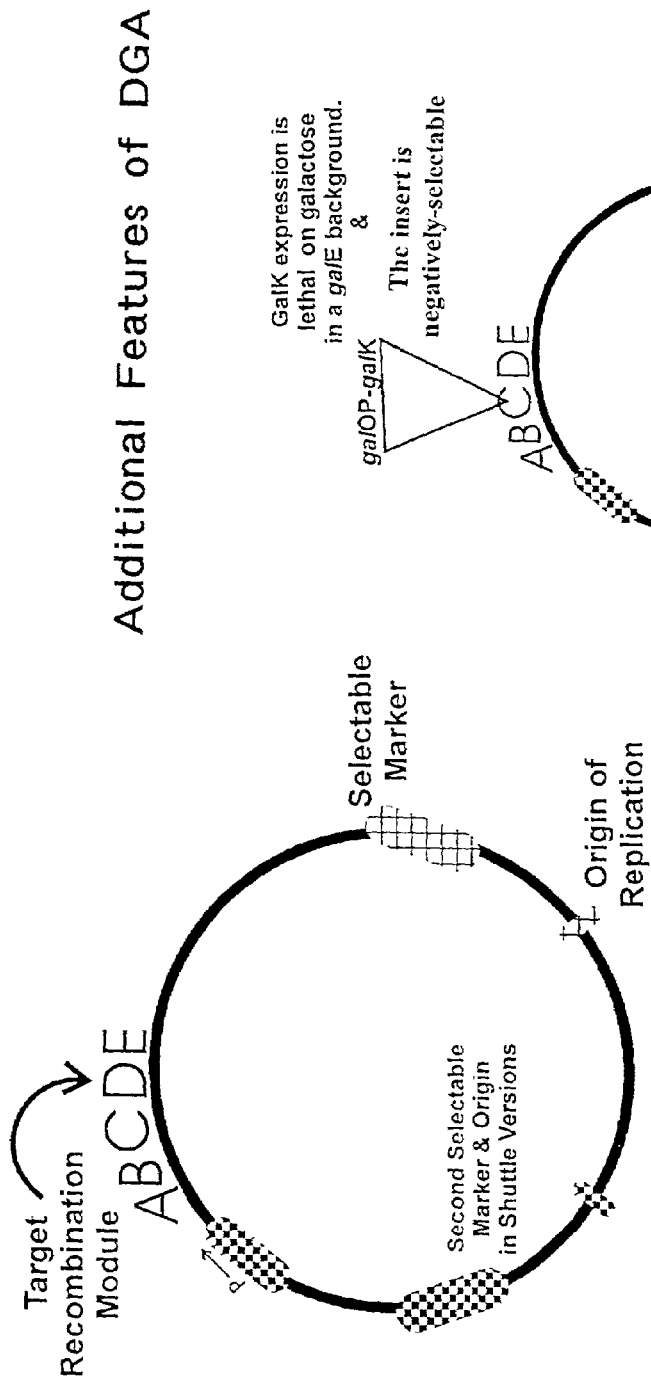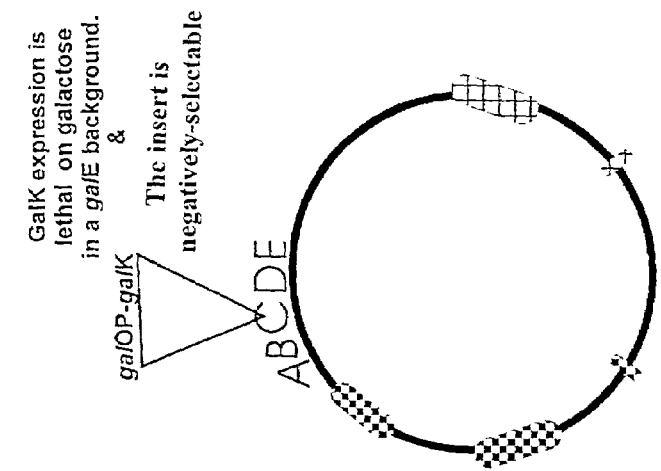
FIG. 2

```
+1   I  K  A    D  K  V    Q  A  Q    G  F  K    G  A  N    V  K  V    A  V  L
 1   ATTAAAGCG  GACAAAGTG  CAGGCTCAA  GGCTTTAAG  GGAGCGAAT  GTAAAAGTA  GCCGTCCTG

+1   D  T  G    I  Q  A    S  H  P    D  L  N    V  V  G    G  A  S    F  V  A
64   GATACAGGA  ATCCAAGCT  TCTCATCCG  GACTTGAAC  GTAGTCGGC  GGAGCAAGC  TTTGTGGCT

+1   G  E  A    Y  N  T    D  G  N    G  H  G    A  H  V    A  G  T    V  A  A
127  GGCGAAGCT  TATAACACC  GACGGCAAC  GGACACGGC  GCACATGTT  GCCGGTACA  GTAGCTGCG

+1   L  D  N    T  T  G    V  L  G    V  A  P    S  V  S    L  Y  A    V  K  V
190  CTTGACAAT  ACAACGGGT  GTATTAGGC  GTTGCGCCA  AGCGTATCC  TTGTACGCG  GTTAAAGTA

+1   L  N  S    S  G  S    G  S  Y    S  G  I    V  S  G    I  E  W    A  T  T
253  CTGAATTCA  AGCGGAAGC  GGATCATAC  AGCGGCATT  GTAAGCGGA  ATCGAGTGG  GCGACAACA

+2   N  G  M    D  V  I    N  M  S    L  G  G    A  S  G    S  T  A    M  K  Q
316  AACGGCATG  GATGTTATC  AATATGAGC  CTTGGGGGA  GCATCAGGC  TCGACAGCG  ATGAAACAG

+1   A  V  D    N  A  Y    A  K  G    V  V  V    V  A  A    A  G  N    S  G  S
379  GCAGTCGAC  AATGCATAT  GCAAAAGGG  GTTGTCGTT  GTAGCTGCA  GCAGGGAAC  AGCGGATCT
```

**DNA Sequence 5A20 *B.licheniformis* isolate**

```
+1   I  K  A    P  A  L    H  S  Q    G  Y  T    G  S  N    V  K  V    A  V  I
 1   ATTAAAGCG  CCGGCTCTT  CACTCTCAA  GGCTACACA  GGTTCTAAC  GTAAAAGTA  GCCGTAATT

+1   D  S  G    I  D  S    S  H  P    D  L  N    V  R  G    G  A  S    F  V  P
64   GACAGCGGA  ATTGACTCT  TCTCATCCT  GACTTGAAC  GTCAGAGGC  GGAGCAAGC  TTCGTACCT

+1   S  E  T    N  P  Y    Q  D  G    S  S  H    G  T  H    V  A  G    T  V  A
127  TCTGAAACA  AACCCATAC  CAAGATGGC  AGTTCTCAC  GGCACACAT  GTAGCCGGT  ACGGTTGCC

+1   A  L  N    N  S  I    G  V  L    G  V  A    P  N  A    S  L  Y    A  V  K
190  GCACTTAAT  AACTCAATC  GGTGTTTTG  GGCGTAGCG  CCAAACGCA  TCGTTATAT  GCAGTAAAA

+1   V  L  D    S  T  G    N  G  Q    Y  S  W    I  I  N    G  I  E    W  A  I
253  GTTCTTGAT  TCAACAGGA  AACGGCCAA  TACAGCTGG  ATTATTAAC  GGCATTGAG  TGGGCCATT

+1   S  N  K    M  D  V    I  N  M    S  L  G    G  P  S    G  S  T    A  L  K
316  TCCAACAAA  ATGGACGTG  ATTAACATG  AGCCTTGGC  GGACCTTCT  GGTTCTACA  GCTTTGAAA

+1   S  V  V    D  R  A    V  A  S    G  I  V    V  V  A    A  A  G    N  E  G
379  TCAGTCGTT  GATAGAGCC  GTAGCCAGC  GGTATCGTC  GTTGTTGCT  GCAGCCGGA  AATGAAGGC

+1   T  S  G    S  S  S    T  I  G    Y  P  A    K  Y  P    S  T  I    A  V  G
442  ACTTCCGGA  AGCTCAAGC  ACAATCGGC  TATCCTGCA  AAATATCCT  TCTACCATT  GCGGTAGGT

+1   A  V  N    S  S  N    Q  R  G    S  F  S    S  V  G    P  E  L    E  V  M
505  GCGGTAAAC  AGCAGCAAC  CAAAGAGGT  TCATTCTCA  AGCGTAGGT  CCTGAGCTT  GAAGTCATG

+1   A  P  G
568  GCTCCTGGC
```

**DNA Sequence 3A13 *B.subtilis* isolate**

FIG. 16

```
      M   M   R   K   K   S   F   W   L   G   M   L   T   A   L   M   L   V   F   T   M
   1  ATGATGAGG AAAAAGAGT TTTTGGCTT GGGATGCTG ACGGCCTTA ATGCTCGTG TTCACGATG

A   F   S   D   S   A   S   A   A   Q   P   A   K   N   V   E   K   D   Y   I   V
  64  GCCTTCAGC GATTCCGCG TCTGCTGCT CAGCCGGCG AAAAATGTT GAAAAGGAT TATATTGTC

G   F   K   S   G   V   K   T   A   S   V   K   K   D   I   I   K   E   S   G   G
 127  GGATTTAAG TCGGGAGTG AAAACCGCA TCCGTCAAA AAGGACATC ATCAAAGAG AGCGGCGGA

K   V   D   K   Q   F   R   I   I   N   A   A   K   A   K   L   D   K   E   A   L
 190  AAAGTGGAC AAGCAGTTT AGAATCATC AACGCGGCA AAAGCGAAG CTAGACAAA GAAGCGCTT

E   E   V   K   N   D   P   D   V   A   Y   V   E   E   D   H   V   A   H   A   L
 253  GAGGAAGTC AAAAATGAT CCGGATGTC GCTTATGTG GAAGAGGAT CACGTAGCT CATGCTTTG

A   Q   T   V   P   Y   G   I   P   L   I   K   A   D   K   V   Q   A   Q   G   Y
 316  GCGCAAACC GTTCCTTAC GGCATTCCT CTCATTAAA GCGGACAAA GTGCAGGCT CAAGGCTAC

K   G   A   N   V   K   V   A   V   L   D   T   G   I   Q   A   S   H   P   D   L
 379  AAGGGAGCG AACGTAAAA GTCGCCGTC CTGGATACA GGAATCCAA GCTTCTCAT CCGGACTTG

N   V   V   G   G   A   S   F   V   A   G   E   A   Y   N   T   D   G   N   G   H
 442  AACGTAGTC GGCGGAGCA AGCTTCGTA GCTGGCGAA GCTTATAAC ACCGACGGC AACGGACAC

G   T   H   V   A   G   T   V   A   A   L   D   N   T   T   G   V   L   G   V   A
 505  GGCACGCAT GTTGCCGGT ACAGTAGCT GCGCTTGAC AATACAACG GGTGTATTA GGCGTTGCG

P   N   V   S   L   Y   A   V   K   V   L   N   S   S   G   S   G   S   Y   S   G
 568  CCGAACGTA TCCTTGTAC GCGGTTAAA GTGCTGAAT TCAAGCGGA AGCGGATCT TACAGCGGC

I   V   S   G   I   E   W   A   T   N   G   M   D   V   I   N   M   S   L   G
 631  ATTGTAAGC GGAATCGAG TGGGCGACG ACAAACGGC ATGGATGTT ATCAACATG AGCCTTGGA

G   P   S   G   S   T   A   M   K   Q   A   V   D   N   A   Y   A   R   G   V   V
 694  GGACCATCA GGCTCAACA GCGATGAAA CAGGCGGTT GACAATGCA TATGCAAGA GGGGTTGTC

V   V   A   A   G   N   S   G   S   S   G   N   T   N   T   I   G   Y   P   A
 757  GTTGTGGCG GCTGCTGGG AACAGCGGA TCTTCAGGA AACACGAAT ACAATCGGC TATCCTGCG

K   Y   D   S   V   I   A   V   G   A   V   D   P   N   S   N   R   A   S   F   S
 820  AAATACGAC TCTGTCATC GCAGTTGGC GCGGTAGAC CCTAACAGC AACAGAGCT TCATTTTCC

S   V   G   A   E   L   E   V   M   A   P   G   A   G   V   Y   S   T   Y   P   T
 883  AGCGTCGGA GCAGAGCTT GAAGTCATG GCTCCTGGC GCAGGCGTG TACAGCACT TACCCAACC

S   T   Y   A   T   L   N   G   T   S   M   A   S   P   H   V   A   G   A   A   A
 946  AGCACTTAT GCAACATTG AACGGAACG TCAATGGCT TCTCCTCAT GTAGCGGGA GCAGCAGCT

L   I   L   S   K   H   P   N   L   S   A   S   Q   V   R   N   R   L   S   S   T
1009  TTGATCTTG TCAAAACAT CCGAACCTT TCAGCTTCA CAAGTCCGC AACCGTCTC TCCAGTACG

A   T   Y   L   G   S   S   F   Y   Y   G   K   G   L   I   N   V   E   A   A   A
1072  GCGACTTAT TTGGGAAGC TCCTTCTAC TATGGAAAA GGTCTGATC AATGTCGAA GCTGCCGCT

Q   *
1135  CAATAA
```

DNA Sequence 5A36 *B.licheniformis* complete

FIG. 17A

```
       V   R   S      K   K   L      W   I   S      L   L   F      A   L   T      L   I   F      T   M   A
   1  GTGAGAAGC  AAAAAATTG  TGGATCAGC  TTGTTGTTT  GCGTTAACG  TTAATCTTT  ACGATGGCG

F   S   N      M   S   A      Q   A   A      G   K   S      S   T   E      K   K   Y      I   V   G
  64  TTCAGCAAC  ATGTCTGCG  CAGGCTGCC  GGAAAAAGC  AGTACAGAA  AAGAAATAC  ATTGTCGGA

F   K   Q      T   M   S      A   M   S      S   A   K      K   K   D      V   I   S      E   K   G
 127  TTTAAACAG  ACAATGAGT  GCCATGAGT  TCCGCCAAG  AAAAAGGAT  GTTATTTCT  GAAAAGGC

G   K   V      Q   K   Q      F   K   Y      V   N   A      A   A   T   L   D      E   K   A
 190  GGAAAGGTT  CAAAAGCAA  TTTAAGTAT  GTTAACGCG  GCCGCAGCA  ACATTGGAT  GAAAAAGCT

V   K   E      L   K   K      D   P   S      V   A   Y      V   E   E      D   H   I      A   H   E
 253  GTAAAGAA  TTGAAAAAA  GATCCGAGC  GTTGCATAT  GTGGAAGAA  GATCATATT  GCACATGAA

Y   A   Q      S   V   P      Y   G   I      S   Q   I      K   A   P      A   L   H      S   Q   G
 316  TATGCGCAA  TCTGTTCCT  TATGGCATT  TCTCAAATT  AAAGCGCCG  GCTCTTCAC  TCTCAAGGC
      ─────────  ─────────  ─────────  ─────────  ─────────→
       Y   T   G      S   N   V      K   V   A      V   I   D      S   G   I      D   S   S      H   P   D
 379  TACACAGGC  TCTAACGTA  AAAGTAGCT  GTTATCGAC  AGCGGAATT  GACTCTTCT  CATCCTGAC

L   N   V      R   G   G      A   S   F      V   P   S      E   T   N      P   Y   Q      D   G   S
 442  TTAAACGTC  AGAGGCGGA  GCAAGCTTC  GTACCTTCT  GAAACAAAC  CCATACCAG  GACGGCAGT

S   H   G      T   H   V      A   G   T      I   A   A      L   N   N      S   I   G      V   L   G
 505  TCTCACGGT  ACGCATGTA  GCCGGTACG  ATTGCCGCT  CTTAATAAC  TCAATCGGT  GTTCTGGGC

V   A   P      S   A   S      L   Y   A      V   K   V      L   D   S      T   G   S      G   Q   Y
 568  GTAGCGCCA  AGCGCATCA  TTATATGCA  GTAAAAGTG  CTTGATTCA  ACAGGAAGC  GGCCAATAT

S   W   I      I   N   G      I   E   W      A   I   S      N   N   M      D   V   I      N   M   S
 631  AGCTGGATT  ATTAACGGC  ATTGAGTGG  GCCATTTCC  AACAATATG  GATGTTATC  AACATGAGC

L   G   G      P   T   G      S   T   A      L   K   T      V   V   D      K   A   V      S   S   G
 694  CTTGGCGGA  CCTACTGGT  TCTACAGCG  CTGAAAACA  GTCGTTGAC  AAAGCCGTT  TCCAGCGGT

I   V   V      A   A   A      A   G   N      E   G   S      S   G   S      T   S   T      V   G   Y
 757  ATCGTCGTT  GCTGCCGCA  GCCGGAAAC  GAAGGTTCA  TCCGGAAGC  ACAAGCACA  GTCGGCTAC

P   A   K      Y   P   S      T   I   A      V   G   A      V   N   S      S   N   Q      R   A   S
 820  CCTGCAAAA  TATCCTTCT  ACTATTGCA  GTAGGTGCG  GTAAACAGC  AGCAACCAA  AGAGCTTCA

F   S   S      A   G   S      E   L   D      V   M   A      P   G   V      S   I   Q      S   T   L
 883  TTCTCCAGC  GCAGGTTCT  GAGCTTGAT  GTGATGGCT  CCTGGCGTG  TCCATCCAA  AGCACACTT
                                     ←─────────  ─────────  ─────────  ─────────
       P   G   G      T   Y   G      A   Y   N      G   T   S      M   A   T      P   H   V      A   R   A
 946  CCTGGAGGC  ACTTACGGC  GCTTATAAC  GGAACGTCC  ATGGCGACT  CCTCACGTT  GCCCGAGCA

A   A   L      I   L   S      K   H   P      T   W   T      N   A   Q      V   R   D      R   L   E
1009  GCAGCGTTA  ATTCTTTCT  AAGCACCCG  ACTTGGACA  AACGCGCAA  GTCCGTGAT  CGTTTAGAA

S   T   A      T   Y   L      G   N   S      F   Y   Y      G   K   G      L   I   N      V   Q   A
1072  AGCACTGCA  ACATATCTT  GGAAACTCT  TTCTACTAT  GGAAAAGGG  TTAATCAAC  GTACAAGCA

A   A   Q      *
1135  GCTGCACAA  TAA
```

DNA Sequence 3A1 *B.subtilis* complete

FIG 17. B

| Oligonucleotide Name | Oligonucleotide SEQ ID NO. | Sequence of oligonucleotide |
|---|---|---|
| MCS1F | SEQ ID NO:1 | 5'-AATTCGCGTTTAAACTTAATTAAGGTACCCATTTTTTGGCAGATCTAGACCAAAAAA TGGGGGGCCCGCCGCTCCCCGGGTGGCGCGCC-3' |
| MCS1R | SEQ ID NO:2 | 5'-AATTGGCGCGCCACCCGGGGAGCGGCGGGCCCGCCGCCCCCATTTTTTGGTCTAGATCTGCCAAA AAATGGGTACCTTAATTAAGTTTAAACGCG-3' |
| BglKF | SEQ ID NO:3 | 5'-GACTGCGAGATCATAGATATAGATTTCACTACGCGGCTGCTCAAACCTGG-3' |
| BglKR | SEQ ID NO:4 | 5'-CCAGGTTTGAGCAGCCGCGTAGTGAAATCTATATCTATGATCTCGCAGTC-3' |
| CC_UPPER | SEQ ID NO:5 | 5'-AATTTACCATGGAGCAATTGCATATGGTTTAAACAGCTCGAGTAGATCTTGGCCGGCCCCATGCAT-3' |
| CC_LOWER | SEQ ID NO:6 | 5'-CGGCGTTATGCATGGTACCCAGCTGACGCTAGCCAAGCGGCCGCAAGATCTACTCGAG CTGTTTAAACCATATGCAATTGCTCCATGG-3' |
| internal primer - upper | SEQ ID NO:7 | 5'-CGCAA(T/A)C(T/C)GTTCCTTA(C/T)GG-3' |
| internal primer - upper | SEQ ID NO:8 | 5'-GCCAGGAGCCAT(C/G)AC(A/T)TCAA-3' |

FIG. 24A

| Oligonucleotide Name | Oligonucleotide SEQ ID NO. | Sequence of oligonucleotide |
|---|---|---|
| *B. lichenformis* Subtilisin Forward Primer | SEQ ID NO:9 | 5'-GGGGTACCGCGGGTCTATTCATACTTTCG-3' |
| *B. lichenformis* Subtilisin Reverse Primer | SEQ ID NO:10 | 5'-GCAGATCTCATTTGTTAGAATATGTTATTGAGCGGC-3' |
| *B. subtilis* Subtilisin Forward Primer | SEQ ID NO:11 | 5'-AGCGGAGATCTCTATTATTGTGCAGCTG-3' |
| *B. subtilis* Subtilisin Reverse Primer | SEQ ID NO:12 | 5'-GCGCGGTACCTGATAAAAGGAGAGGGTAAAGAG-3' |
| Galactokinase upper primer | SEQ ID NO:17 | 5'-GGAAGATCTAGAGGTTTTCACCGTCATCACCG-3' |
| Galactokinase lower primer | SEQ ID NO:18 | 5'-GGTAGATCTCTTTCGTCGTCTTCAAGAATTCCGC-3' |

FIG. 24B

SEQUENCE LISTING

```
<160> NUMBER OF SEQ ID NOS: 22

<210> SEQ ID NO 1
<211> LENGTH: 87
<212> TYPE: DNA
<213> ORGANISM: Artificial Sequence
<220> FEATURE:
<223> OTHER INFORMATION: Description of artificial sequence: Primer

<400> SEQUENCE: 1
aattcgcgtt taaacttaat taaggtaccc attttttggc agatctagac caaaaaatgg      60
gggcggccgc tccccgggtg gcgcgcc                                         87

<210> SEQ ID NO 2
<211> LENGTH: 87
<212> TYPE: DNA
<213> ORGANISM: Artificial Sequence
<220> FEATURE:
<223> OTHER INFORMATION: Description of artificial sequence: Primer

<400> SEQUENCE: 2
aattggcgcg ccacccgggg agcggccgcc cccatttttt ggtctagatc tgccaaaaaa      60
tgggtacctt aattaagttt aaacgcg                                         87

<210> SEQ ID NO 3
<211> LENGTH: 50
<212> TYPE: DNA
<213> ORGANISM: Artificial Sequence
<220> FEATURE:
<223> OTHER INFORMATION: Description of artificial sequence: Primer

<400> SEQUENCE: 3
gactgcgaga tcatagatat agatttcact acgcggctgc tcaaacctgg               50

<210> SEQ ID NO 4
<211> LENGTH: 50
<212> TYPE: DNA
<213> ORGANISM: Artificial Sequence
<220> FEATURE:
<223> OTHER INFORMATION: Description of artificial sequence: Primer

<400> SEQUENCE: 4
ccaggtttga gcagccgcgt agtgaaatct atatctatga tctcgcagtc               50

<210> SEQ ID NO 5
<211> LENGTH: 87
<212> TYPE: DNA
<213> ORGANISM: Artificial Sequence
<220> FEATURE:
<223> OTHER INFORMATION: Description of artificial sequence: Primer

<400> SEQUENCE: 5
aatttaccat ggagcaattg catatggttt aaacagctcg agtagatctt gcggccgctt      60
```

```
ggctagcgtc agctgggtac catgcat                                              87

<210> SEQ ID NO 6
<211> LENGTH: 87
<212> TYPE: DNA
<213> ORGANISM: Artificial Sequence
<220> FEATURE:
<223> OTHER INFORMATION: Description of artificial sequence: Primer

<400> SEQUENCE: 6
cgcgttatgc atggtaccca gctgacgcta gccaagcggc cgcaagatct actcgagctg         60
tttaaaccat atgcaattgc tccatgg                                              87

<210> SEQ ID NO 7
<211> LENGTH: 19
<212> TYPE: DNA
<213> ORGANISM: Artificial Sequence
<220> FEATURE:
<223> OTHER INFORMATION: Description of artificial sequence: Primer

<400> SEQUENCE: 7
cgcaawcygt tccttaygg                                                       19

<210> SEQ ID NO 8
<211> LENGTH: 20
<212> TYPE: DNA
<213> ORGANISM: Artificial Sequence
<220> FEATURE:
<223> OTHER INFORMATION: Description of artificial sequence: Primer

<400> SEQUENCE: 8
gccaggagcc atsacwtcaa                                                      20

<210> SEQ ID NO 9
<211> LENGTH: 28
<212> TYPE: DNA
<213> ORGANISM: Artificial Sequence
<220> FEATURE:
<223> OTHER INFORMATION: Description of artificial sequence: Primer

<400> SEQUENCE: 9
ggggtaccgc ggtctattca tactttcg                                             28

<210> SEQ ID NO 10
<211> LENGTH: 36
<212> TYPE: DNA
<213> ORGANISM: Artificial Sequence
<220> FEATURE:
<223> OTHER INFORMATION: Description of artificial sequence: Primer

<400> SEQUENCE: 10
gcagatctca tttgttagaa tatgttattg agcggc                                    36

<210> SEQ ID NO 11
<211> LENGTH: 27
<212> TYPE: DNA
<213> ORGANISM: Artificial Sequence
<220> FEATURE:
<223> OTHER INFORMATION: Description of artificial sequence: Primer

<400> SEQUENCE: 11
agcgagatct ctattattgt gcagctg                                              27

<210> SEQ ID NO 12
```

-continued

```
<211> LENGTH: 33
<212> TYPE: DNA
<213> ORGANISM: Artificial Sequence
<220> FEATURE:
<223> OTHER INFORMATION: Description of artificial sequence: Primer

<400> SEQUENCE: 12
gcgcggtacc tgataaaagg agagggtaaa gag                                  33

<210> SEQ ID NO 13
<211> LENGTH: 1140
<212> TYPE: DNA
<213> ORGANISM: Bacillus licheniformis
<220> FEATURE:
<221> NAME/KEY: CDS
<222> LOCATION: (1)..(1140)

<400> SEQUENCE: 13
```

| | | | | | | | | | | | | | | | | |
|---|---|---|---|---|---|---|---|---|---|---|---|---|---|---|---|---|
| atg | atg | agg | aaa | aag | agt | ttt | tgg | ctt | ggg | atg | ctg | acg | gcc | tta | atg | 48 |
| Met | Met | Arg | Lys | Lys | Ser | Phe | Trp | Leu | Gly | Met | Leu | Thr | Ala | Leu | Met | |
| 1 | | | | 5 | | | | | 10 | | | | | 15 | | |
| ctc | gtg | ttc | acg | atg | gcc | ttc | agc | gat | tcc | gcg | tct | gct | gct | cag | ccg | 96 |
| Leu | Val | Phe | Thr | Met | Ala | Phe | Ser | Asp | Ser | Ala | Ser | Ala | Ala | Gln | Pro | |
| | | | 20 | | | | | 25 | | | | | 30 | | | |
| gcg | aaa | aat | gtt | gaa | aag | gat | tat | att | gtc | gga | ttt | aag | tcg | gga | gtg | 144 |
| Ala | Lys | Asn | Val | Glu | Lys | Asp | Tyr | Ile | Val | Gly | Phe | Lys | Ser | Gly | Val | |
| | 35 | | | | | 40 | | | | | 45 | | | | | |
| aaa | acc | gca | tcc | gtc | aaa | aag | gac | atc | atc | aaa | gag | agc | ggc | gga | aaa | 192 |
| Lys | Thr | Ala | Ser | Val | Lys | Lys | Asp | Ile | Ile | Lys | Glu | Ser | Gly | Gly | Lys | |
| 50 | | | | | 55 | | | | | 60 | | | | | | |
| gtg | gac | aag | cag | ttt | aga | atc | atc | aac | gcg | gca | aaa | gcg | aag | cta | gac | 240 |
| Val | Asp | Lys | Gln | Phe | Arg | Ile | Ile | Asn | Ala | Ala | Lys | Ala | Lys | Leu | Asp | |
| 65 | | | | | 70 | | | | | 75 | | | | | 80 | |
| aaa | gaa | gcg | ctt | gag | gaa | gtc | aaa | aat | gat | ccg | gat | gtc | gct | tat | gtg | 288 |
| Lys | Glu | Ala | Leu | Glu | Glu | Val | Lys | Asn | Asp | Pro | Asp | Val | Ala | Tyr | Val | |
| | | | | 85 | | | | | 90 | | | | | 95 | | |
| gaa | gag | gat | cac | gta | gct | cat | gct | ttg | gcg | caa | acc | gtt | cct | tac | ggc | 336 |
| Glu | Glu | Asp | His | Val | Ala | His | Ala | Leu | Ala | Gln | Thr | Val | Pro | Tyr | Gly | |
| | | | | 100 | | | | | 105 | | | | | 110 | | |
| att | cct | ctc | att | aaa | gcg | gac | aaa | gtg | cag | gct | caa | ggc | tac | aag | gga | 384 |
| Ile | Pro | Leu | Ile | Lys | Ala | Asp | Lys | Val | Gln | Ala | Gln | Gly | Tyr | Lys | Gly | |
| | | | 115 | | | | | 120 | | | | | 125 | | | |
| gcg | aac | gta | aaa | gtc | gcc | gtc | ctg | gat | aca | gga | atc | caa | gct | tct | cat | 432 |
| Ala | Asn | Val | Lys | Val | Ala | Val | Leu | Asp | Thr | Gly | Ile | Gln | Ala | Ser | His | |
| | | 130 | | | | | 135 | | | | | 140 | | | | |
| ccg | gac | ttg | aac | gta | gtc | ggc | gga | gca | agc | ttc | gta | gct | ggc | gaa | gct | 480 |
| Pro | Asp | Leu | Asn | Val | Val | Gly | Gly | Ala | Ser | Phe | Val | Ala | Gly | Glu | Ala | |
| 145 | | | | | 150 | | | | | 155 | | | | | 160 | |
| tat | aac | acc | gac | ggc | aac | gga | cac | ggc | acg | cat | gtt | gcc | ggt | aca | gta | 528 |
| Tyr | Asn | Thr | Asp | Gly | Asn | Gly | His | Gly | Thr | His | Val | Ala | Gly | Thr | Val | |
| | | | | 165 | | | | | 170 | | | | | 175 | | |
| gct | gcg | ctt | gac | aat | aca | acg | ggt | gta | tta | ggc | gtt | gcg | ccg | aac | gta | 576 |
| Ala | Ala | Leu | Asp | Asn | Thr | Thr | Gly | Val | Leu | Gly | Val | Ala | Pro | Asn | Val | |
| | | | 180 | | | | | 185 | | | | | 190 | | | |
| tcc | ttg | tac | gcg | gtt | aaa | gtg | ctg | aat | tca | agc | gga | agc | gga | tct | tac | 624 |
| Ser | Leu | Tyr | Ala | Val | Lys | Val | Leu | Asn | Ser | Ser | Gly | Ser | Gly | Ser | Tyr | |
| | | 195 | | | | | 200 | | | | | 205 | | | | |
| agc | ggc | att | gta | agc | gga | atc | gag | tgg | gcg | acg | aca | aac | ggc | atg | gat | 672 |
| Ser | Gly | Ile | Val | Ser | Gly | Ile | Glu | Trp | Ala | Thr | Thr | Asn | Gly | Met | Asp | |
| | 210 | | | | | 215 | | | | | 220 | | | | | |
| gtt | atc | aac | atg | agc | ctt | gga | gga | cca | tca | ggc | tca | aca | gcg | atg | aaa | 720 |
| Val | Ile | Asn | Met | Ser | Leu | Gly | Gly | Pro | Ser | Gly | Ser | Thr | Ala | Met | Lys | |

```
                    225                 230                 235                 240
cag gcg gtt gac aat gca tat gca aga ggg gtt gtc gtt gtg gcg gct        768
Gln Ala Val Asp Asn Ala Tyr Ala Arg Gly Val Val Val Val Ala Ala
                    245                 250                 255 gct ggg aac agc gga tct tca gga aac acg aat aca atc ggc tat cct        816
Ala Gly Asn Ser Gly Ser Ser Gly Asn Thr Asn Thr Ile Gly Tyr Pro
                260                 265                 270 gcg aaa tac gac tct gtc atc gca gtt ggc gcg gta gac cct aac agc        864
Ala Lys Tyr Asp Ser Val Ile Ala Val Gly Ala Val Asp Pro Asn Ser
            275                 280                 285 aac aga gct tca ttt tcc agc gtc gga gca gag ctt gaa gtc atg gct        912
Asn Arg Ala Ser Phe Ser Ser Val Gly Ala Glu Leu Glu Val Met Ala
        290                 295                 300 cct ggc gca ggc gtg tac agc act tac cca acc agc act tat gca aca        960
Pro Gly Ala Gly Val Tyr Ser Thr Tyr Pro Thr Ser Thr Tyr Ala Thr
305                 310                 315                 320 ttg aac gga acg tca atg gct tct cct cat gta gcg gga gca gca gct       1008
Leu Asn Gly Thr Ser Met Ala Ser Pro His Val Ala Gly Ala Ala Ala
                325                 330                 335 ttg atc ttg tca aaa cat ccg aac ctt tca gct tca caa gtc cgc aac       1056
Leu Ile Leu Ser Lys His Pro Asn Leu Ser Ala Ser Gln Val Arg Asn
            340                 345                 350 cgt ctc tcc agt acg gcg act tat ttg gga agc tcc ttc tac tat gga       1104
Arg Leu Ser Ser Thr Ala Thr Tyr Leu Gly Ser Ser Phe Tyr Tyr Gly
        355                 360                 365 aaa ggt ctg atc aat gtc gaa gct gcc gct caa taa                       1140
Lys Gly Leu Ile Asn Val Glu Ala Ala Ala Gln
370                 375
```

<210> SEQ ID NO 14
<211> LENGTH: 379
<212> TYPE: PRT
<213> ORGANISM: Bacillus licheniformis

<400> SEQUENCE: 14

```
Met Met Arg Lys Lys Ser Phe Trp Leu Gly Met Leu Thr Ala Leu Met
1               5                   10                  15

Leu Val Phe Thr Met Ala Phe Ser Asp Ser Ala Ser Ala Ala Gln Pro
            20                  25                  30

Ala Lys Asn Val Glu Lys Asp Tyr Ile Val Gly Phe Lys Ser Gly Val
        35                  40                  45

Lys Thr Ala Ser Val Lys Lys Asp Ile Ile Lys Glu Ser Gly Gly Lys
    50                  55                  60

Val Asp Lys Gln Phe Arg Ile Ile Asn Ala Ala Lys Ala Lys Leu Asp
65                  70                  75                  80

Lys Glu Ala Leu Glu Glu Val Lys Asn Asp Pro Asp Val Ala Tyr Val
                85                  90                  95

Glu Glu Asp His Val Ala His Ala Leu Ala Gln Thr Val Pro Tyr Gly
            100                 105                 110

Ile Pro Leu Ile Lys Ala Asp Lys Val Gln Ala Gln Gly Tyr Lys Gly
        115                 120                 125

Ala Asn Val Lys Val Ala Val Leu Asp Thr Gly Ile Gln Ala Ser His
    130                 135                 140

Pro Asp Leu Asn Val Val Gly Gly Ala Ser Phe Val Ala Gly Glu Ala
145                 150                 155                 160

Tyr Asn Thr Asp Gly Asn Gly His Gly Thr His Val Ala Gly Thr Val
                165                 170                 175
```

-continued

```
Ala Ala Leu Asp Asn Thr Thr Gly Val Leu Gly Val Ala Pro Asn Val
            180                 185                 190

Ser Leu Tyr Ala Lys Val Leu Asn Ser Ser Gly Ser Gly Ser Tyr
        195                 200             205

Ser Gly Ile Val Ser Gly Ile Glu Trp Ala Thr Thr Asn Gly Met Asp
        210                 215                 220

Val Ile Asn Met Ser Leu Gly Gly Pro Ser Gly Ser Thr Ala Met Lys
225                 230                 235                 240

Gln Ala Val Asp Asn Ala Tyr Ala Arg Gly Val Val Val Ala Ala
                245                 250                 255

Ala Gly Asn Ser Gly Ser Ser Gly Asn Thr Asn Thr Ile Gly Tyr Pro
            260                 265                 270

Ala Lys Tyr Asp Ser Val Ile Ala Val Gly Ala Val Asp Pro Asn Ser
        275                 280                 285

Asn Arg Ala Ser Phe Ser Ser Val Gly Ala Glu Leu Glu Val Met Ala
        290                 295                 300

Pro Gly Ala Gly Val Tyr Ser Thr Tyr Pro Thr Ser Thr Tyr Ala Thr
305                 310                 315                 320

Leu Asn Gly Thr Ser Met Ala Ser Pro His Val Ala Gly Ala Ala Ala
            325                 330                 335

Leu Ile Leu Ser Lys His Pro Asn Leu Ser Ala Ser Gln Val Arg Asn
            340                 345                 350

Arg Leu Ser Ser Thr Ala Thr Tyr Leu Gly Ser Ser Phe Tyr Tyr Gly
            355                 360                 365

Lys Gly Leu Ile Asn Val Glu Ala Ala Ala Gln
        370                 375
```

<210> SEQ ID NO 15
<211> LENGTH: 1146
<212> TYPE: DNA
<213> ORGANISM: Bacillus subtilis
<220> FEATURE:
<221> NAME/KEY: CDS
<222> LOCATION: (1)..(1146)

<400> SEQUENCE: 15

```
gtg aga agc aaa aaa ttg tgg atc agc ttg ttg ttt gcg tta acg tta    48
Val Arg Ser Lys Lys Leu Trp Ile Ser Leu Leu Phe Ala Leu Thr Leu
1               5                   10                  15 atc ttt acg atg gcg ttc agc aac atg tct gcg cag gct gcc gga aaa    96
Ile Phe Thr Met Ala Phe Ser Asn Met Ser Ala Gln Ala Ala Gly Lys
            20                  25                  30 agc agt aca gaa aag aaa tac att gtc gga ttt aaa cag aca atg agt    144
Ser Ser Thr Glu Lys Lys Tyr Ile Val Gly Phe Lys Gln Thr Met Ser
        35                  40                  45 gcc atg agt tcc gcc aag aaa aag gat gtt att tct gaa aaa ggc gga    192
Ala Met Ser Ser Ala Lys Lys Lys Asp Val Ile Ser Glu Lys Gly Gly
    50                  55                  60 aag gtt caa aag caa ttt aag tat gtt aac gcg gcc gca gca aca ttg    240
Lys Val Gln Lys Gln Phe Lys Tyr Val Asn Ala Ala Ala Ala Thr Leu
65                  70                  75                  80 gat gaa aaa gct gta aaa gaa ttg aaa aaa gat ccg agc gtt gca tat    288
Asp Glu Lys Ala Val Lys Glu Leu Lys Lys Asp Pro Ser Val Ala Tyr
                85                  90                  95 gtg gaa gaa gat cat att gca cat gaa tat gcg caa tct gtt cct tat    336
Val Glu Glu Asp His Ile Ala His Glu Tyr Ala Gln Ser Val Pro Tyr
            100                 105                 110 ggc att tct caa att aaa gcg ccg gct ctt cac tct caa ggc tac aca    384
```

| | | | | | | | | | | | | |
|---|---|---|---|---|---|---|---|---|---|---|---|---|
| Gly | Ile | Ser | Gln | Ile | Lys | Ala | Pro | Ala | Leu | His | Ser | Gln | Gly | Tyr | Thr |
| | | | 115 | | | | 120 | | | | | 125 | | | |

```
ggc tct aac gta aaa gta gct gtt atc gac agc gga att gac tct tct      432
Gly Ser Asn Val Lys Val Ala Val Ile Asp Ser Gly Ile Asp Ser Ser
    130             135                 140 cat cct gac tta aac gtc aga ggc gga gca agc ttc gta cct tct gaa      480
His Pro Asp Leu Asn Val Arg Gly Gly Ala Ser Phe Val Pro Ser Glu
145                 150                 155                 160 aca aac cca tac cag gac ggc agt tct cac ggt acg cat gta gcc ggt      528
Thr Asn Pro Tyr Gln Asp Gly Ser Ser His Gly Thr His Val Ala Gly
                165                 170                 175 acg att gcc gct ctt aat aac tca atc ggt gtt ctg ggc gta gcg cca      576
Thr Ile Ala Ala Leu Asn Asn Ser Ile Gly Val Leu Gly Val Ala Pro
            180                 185                 190 agc gca tca tta tat gca gta aaa gtg ctt gat tca aca gga agc ggc      624
Ser Ala Ser Leu Tyr Ala Val Lys Val Leu Asp Ser Thr Gly Ser Gly
        195                 200                 205 caa tat agc tgg att att aac ggc att gag tgg gcc att tcc aac aat      672
Gln Tyr Ser Trp Ile Ile Asn Gly Ile Glu Trp Ala Ile Ser Asn Asn
    210                 215                 220 atg gat gtt atc aac atg agc ctt ggc gga cct act ggt tct aca gcg      720
Met Asp Val Ile Asn Met Ser Leu Gly Gly Pro Thr Gly Ser Thr Ala
225                 230                 235                 240 ctg aaa aca gtc gtt gac aaa gcc gtt tcc agc ggt atc gtc gtt gct      768
Leu Lys Thr Val Val Asp Lys Ala Val Ser Ser Gly Ile Val Val Ala
                245                 250                 255 gcc gca gcc gga aac gaa ggt tca tcc gga agc aca agc aca gtc ggc      816
Ala Ala Ala Gly Asn Glu Gly Ser Ser Gly Ser Thr Ser Thr Val Gly
            260                 265                 270 tac cct gca aaa tat cct tct act att gca gta ggt gcg gta aac agc      864
Tyr Pro Ala Lys Tyr Pro Ser Thr Ile Ala Val Gly Ala Val Asn Ser
        275                 280                 285 agc aac caa aga gct tca ttc tcc agc gca ggt tct gag ctt gat gtg      912
Ser Asn Gln Arg Ala Ser Phe Ser Ser Ala Gly Ser Glu Leu Asp Val
    290                 295                 300 atg gct cct ggc gtg tcc atc caa agc aca ctt cct gga ggc act tac      960
Met Ala Pro Gly Val Ser Ile Gln Ser Thr Leu Pro Gly Gly Thr Tyr
305                 310                 315                 320 ggc gct tat aac gga acg tcc atg gcg act cct cac gtt gcc cga gca     1008
Gly Ala Tyr Asn Gly Thr Ser Met Ala Thr Pro His Val Ala Arg Ala
                325                 330                 335 gca gcg tta att ctt tct aag cac ccg act tgg aca aac gcg caa gtc     1056
Ala Ala Leu Ile Leu Ser Lys His Pro Thr Trp Thr Asn Ala Gln Val
            340                 345                 350 cgt gat cgt tta gaa agc act gca aca tat ctt gga aac tct ttc tac     1104
Arg Asp Arg Leu Glu Ser Thr Ala Thr Tyr Leu Gly Asn Ser Phe Tyr
        355                 360                 365 tat gga aaa ggg tta atc aac gta caa gca gct gca caa taa             1146
Tyr Gly Lys Gly Leu Ile Asn Val Gln Ala Ala Ala Gln
        370                 375                 380

<210> SEQ ID NO 16
<211> LENGTH: 381
<212> TYPE: PRT
<213> ORGANISM: Bacillus subtilis

<400> SEQUENCE: 16

Val Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
```

```
                    20                  25                  30
Ser Ser Thr Glu Lys Lys Tyr Ile Val Gly Phe Lys Gln Thr Met Ser
            35                  40                  45

Ala Met Ser Ser Ala Lys Lys Lys Asp Val Ile Ser Glu Lys Gly Gly
    50                  55                  60

Lys Val Gln Lys Gln Phe Lys Tyr Val Asn Ala Ala Ala Thr Leu
65                  70                  75                  80

Asp Glu Lys Ala Val Lys Glu Leu Lys Lys Asp Pro Ser Val Ala Tyr
                85                  90                  95

Val Glu Glu Asp His Ile Ala His Glu Tyr Ala Gln Ser Val Pro Tyr
                100                 105                 110

Gly Ile Ser Gln Ile Lys Ala Pro Ala Leu His Ser Gln Gly Tyr Thr
                115                 120                 125

Gly Ser Asn Val Lys Val Ala Val Ile Asp Ser Gly Ile Asp Ser Ser
                130                 135                 140

His Pro Asp Leu Asn Val Arg Gly Gly Ala Ser Phe Val Pro Ser Glu
145                 150                 155                 160

Thr Asn Pro Tyr Gln Asp Gly Ser Ser His Gly Thr His Val Ala Gly
                165                 170                 175

Thr Ile Ala Ala Leu Asn Asn Ser Ile Gly Val Leu Gly Val Ala Pro
                180                 185                 190

Ser Ala Ser Leu Tyr Ala Val Lys Val Leu Asp Ser Thr Gly Ser Gly
                195                 200                 205

Gln Tyr Ser Trp Ile Ile Asn Gly Ile Glu Trp Ala Ile Ser Asn Asn
                210                 215                 220

Met Asp Val Ile Asn Met Ser Leu Gly Gly Pro Thr Gly Ser Thr Ala
225                 230                 235                 240

Leu Lys Thr Val Val Asp Lys Ala Val Ser Ser Gly Ile Val Val Ala
                245                 250                 255

Ala Ala Ala Gly Asn Glu Gly Ser Ser Gly Ser Thr Ser Thr Val Gly
                260                 265                 270

Tyr Pro Ala Lys Tyr Pro Ser Thr Ile Ala Val Gly Ala Val Asn Ser
                275                 280                 285

Ser Asn Gln Arg Ala Ser Phe Ser Ser Ala Gly Ser Glu Leu Asp Val
290                 295                 300

Met Ala Pro Gly Val Ser Ile Gln Ser Thr Leu Pro Gly Gly Thr Tyr
305                 310                 315                 320

Gly Ala Tyr Asn Gly Thr Ser Met Ala Thr Pro His Val Ala Arg Ala
                325                 330                 335

Ala Ala Leu Ile Leu Ser Lys His Pro Thr Trp Thr Asn Ala Gln Val
                340                 345                 350

Arg Asp Arg Leu Glu Ser Thr Ala Thr Tyr Leu Gly Asn Ser Phe Tyr
                355                 360                 365

Tyr Gly Lys Gly Leu Ile Asn Val Gln Ala Ala Gln
                370                 375                 380
```

<210> SEQ ID NO 17
<211> LENGTH: 32
<212> TYPE: DNA
<213> ORGANISM: Artificial Sequence
<220> FEATURE:
<223> OTHER INFORMATION: Description of artificial sequence: Primer

<400> SEQUENCE: 17
ggaagatcta gaggttttca ccgtcatcac cg                                    32

```
<210> SEQ ID NO 18
<211> LENGTH: 34
<212> TYPE: DNA
<213> ORGANISM: Artificial Sequence
<220> FEATURE:
<223> OTHER INFORMATION: Description of artificial sequence: Primer

<400> SEQUENCE: 18
ggtagatctc tttcgtcgtc ttcaagaatt ccgc                              34

<210> SEQ ID NO 19
<211> LENGTH: 441
<212> TYPE: DNA
<213> ORGANISM: Bacillus subtilis
<220> FEATURE:
<221> NAME/KEY: CDS
<222> LOCATION: (1)..(441)

<400> SEQUENCE: 19 att aaa gcg gac aaa gtg cag gct caa ggc ttt aag gga gcg aat gta    48
Ile Lys Ala Asp Lys Val Gln Ala Gln Gly Phe Lys Gly Ala Asn Val
1               5                   10                  15 aaa gta gcc gtc ctg gat aca gga atc caa gct tct cat ccg gac ttg    96
Lys Val Ala Val Leu Asp Thr Gly Ile Gln Ala Ser His Pro Asp Leu
            20                  25                  30 aac gta gtc ggc gga gca agc ttt gtg gct ggc gaa gct tat aac acc   144
Asn Val Val Gly Gly Ala Ser Phe Val Ala Gly Glu Ala Tyr Asn Thr
        35                  40                  45 gac ggc aac gga cac ggc gca cat gtt gcc ggt aca gta gct gcg ctt   192
Asp Gly Asn Gly His Gly Ala His Val Ala Gly Thr Val Ala Ala Leu
    50                  55                  60 gac aat aca acg ggt gta tta ggc gtt gcg cca agc gta tcc ttg tac   240
Asp Asn Thr Thr Gly Val Leu Gly Val Ala Pro Ser Val Ser Leu Tyr
65                  70                  75                  80 gcg gtt aaa gta ctg aat tca agc gga agc gga tca tac agc ggc att   288
Ala Val Lys Val Leu Asn Ser Ser Gly Ser Gly Ser Tyr Ser Gly Ile
                85                  90                  95 gta agc gga atc gag tgg gcg aca aca aac ggc atg gat gtt atc aat   336
Val Ser Gly Ile Glu Trp Ala Thr Thr Asn Gly Met Asp Val Ile Asn
            100                 105                 110 atg agc ctt ggg gga gca tca ggc tcg aca gcg atg aaa cag gca gtc   384
Met Ser Leu Gly Gly Ala Ser Gly Ser Thr Ala Met Lys Gln Ala Val
        115                 120                 125 gac aat gca tat gca aaa ggg gtt gtc gtt gta gct gca gca ggg aac   432
Asp Asn Ala Tyr Ala Lys Gly Val Val Val Val Ala Ala Ala Gly Asn
    130                 135                 140 agc gga tct                                                       441
Ser Gly Ser
145

<210> SEQ ID NO 20
<211> LENGTH: 147
<212> TYPE: PRT
<213> ORGANISM: Bacillus subtilis

<400> SEQUENCE: 20

Ile Lys Ala Asp Lys Val Gln Ala Gln Gly Phe Lys Gly Ala Asn Val
1               5                   10                  15

Lys Val Ala Val Leu Asp Thr Gly Ile Gln Ala Ser His Pro Asp Leu
            20                  25                  30

Asn Val Val Gly Gly Ala Ser Phe Val Ala Gly Glu Ala Tyr Asn Thr
```

```
                    35                  40                  45
Asp Gly Asn Gly His Gly Ala His Val Ala Gly Thr Val Ala Ala Leu
     50                  55                  60

Asp Asn Thr Thr Gly Val Leu Gly Val Ala Pro Ser Val Ser Leu Tyr
 65                  70                  75                  80

Ala Val Lys Val Leu Asn Ser Gly Ser Gly Ser Tyr Ser Gly Ile
                 85                  90                  95

Val Ser Gly Ile Glu Trp Ala Thr Thr Asn Gly Met Asp Val Ile Asn
                100                 105                 110

Met Ser Leu Gly Gly Ala Ser Gly Ser Thr Ala Met Lys Gln Ala Val
                115                 120                 125

Asp Asn Ala Tyr Ala Lys Gly Val Val Val Ala Ala Gly Asn
                130                 135                 140

Ser Gly Ser
145

<210> SEQ ID NO 21
<211> LENGTH: 576
<212> TYPE: DNA
<213> ORGANISM: Bacillus subtilis
<220> FEATURE:
<221> NAME/KEY: CDS
<222> LOCATION: (1)..(576)

<400> SEQUENCE: 21 att aaa gcg ccg gct ctt cac tct caa ggc tac aca ggt tct aac gta      48
Ile Lys Ala Pro Ala Leu His Ser Gln Gly Tyr Thr Gly Ser Asn Val
 1               5                  10                  15 aaa gta gcc gta att gac agc gga att gac tct tct cat cct gac ttg      96
Lys Val Ala Val Ile Asp Ser Gly Ile Asp Ser Ser His Pro Asp Leu
             20                  25                  30 aac gtc aga ggc gga gca agc ttc gta cct tct gaa aca aac cca tac    144
Asn Val Arg Gly Gly Ala Ser Phe Val Pro Ser Glu Thr Asn Pro Tyr
         35                  40                  45 caa gat ggc agt tct cac ggc aca cat gta gcc ggt acg gtt gcc gca    192
Gln Asp Gly Ser Ser His Gly Thr His Val Ala Gly Thr Val Ala Ala
     50                  55                  60 ctt aat aac tca atc ggt gtt ttg ggc gta gcg cca aac gca tcg tta    240
Leu Asn Asn Ser Ile Gly Val Leu Gly Val Ala Pro Asn Ala Ser Leu
 65                  70                  75                  80 tat gca gta aaa gtt ctt gat tca aca gga aac ggc caa tac agc tgg    288
Tyr Ala Val Lys Val Leu Asp Ser Thr Gly Asn Gly Gln Tyr Ser Trp
                 85                  90                  95 att att aac ggc att gag tgg gcc att tcc aac aaa atg gac gtg att    336
Ile Ile Asn Gly Ile Glu Trp Ala Ile Ser Asn Lys Met Asp Val Ile
                100                 105                 110 aac atg agc ctt ggc gga cct tct ggt tct aca gct ttg aaa tca gtc    384
Asn Met Ser Leu Gly Gly Pro Ser Gly Ser Thr Ala Leu Lys Ser Val
                115                 120                 125 gtt gat aga gcc gta gcc agc ggt atc gtc gtt gtt gct gca gcc gga    432
Val Asp Arg Ala Val Ala Ser Gly Ile Val Val Val Ala Ala Ala Gly
                130                 135                 140 aat gaa ggc act tcc gga agc tca agc aca atc ggt tat cct gca aaa    480
Asn Glu Gly Thr Ser Gly Ser Ser Ser Thr Ile Gly Tyr Pro Ala Lys
145                 150                 155                 160 tat cct tct acc att gcg gta ggt gcg gta aac agc agc aac caa aga    528
Tyr Pro Ser Thr Ile Ala Val Gly Ala Val Asn Ser Ser Asn Gln Arg
                165                 170                 175 ggt tca ttc tca agc gta ggt cct gag ctt gaa gtc atg gct cct ggc    576
```

-continued

```
Gly Ser Phe Ser Ser Val Gly Pro Glu Leu Glu Val Met Ala Pro Gly
            180                 185                 190

<210> SEQ ID NO 22
<211> LENGTH: 192
<212> TYPE: PRT
<213> ORGANISM: Bacillus subtilis

<400> SEQUENCE: 22

Ile Lys Ala Pro Ala Leu His Ser Gln Gly Tyr Thr Gly Ser Asn Val
1               5                   10                  15

Lys Val Ala Val Ile Asp Ser Gly Ile Asp Ser Ser His Pro Asp Leu
            20                  25                  30

Asn Val Arg Gly Gly Ala Ser Phe Val Pro Ser Glu Thr Asn Pro Tyr
            35                  40                  45

Gln Asp Gly Ser Ser His Gly Thr His Val Ala Gly Thr Val Ala Ala
        50                  55                  60

Leu Asn Asn Ser Ile Gly Val Leu Gly Val Ala Pro Asn Ala Ser Leu
65                  70                  75                  80

Tyr Ala Val Lys Val Leu Asp Ser Thr Gly Asn Gly Gln Tyr Ser Trp
                85                  90                  95

Ile Ile Asn Gly Ile Glu Trp Ala Ile Ser Asn Lys Met Asp Val Ile
            100                 105                 110

Asn Met Ser Leu Gly Gly Pro Ser Gly Ser Thr Ala Leu Lys Ser Val
            115                 120                 125

Val Asp Arg Ala Val Ala Ser Gly Ile Val Val Ala Ala Ala Ala Gly
        130                 135                 140

Asn Glu Gly Thr Ser Gly Ser Ser Ser Thr Ile Gly Tyr Pro Ala Lys
145                 150                 155                 160

Tyr Pro Ser Thr Ile Ala Val Gly Ala Val Asn Ser Ser Asn Gln Arg
                165                 170                 175

Gly Ser Phe Ser Ser Val Gly Pro Glu Leu Glu Val Met Ala Pro Gly
            180                 185                 190
```

METHODS AND COMPOSITIONS FOR DIRECTED GENE ASSEMBLY

The present application claims priority under 35 U.S.C. § 119(e) to U.S. provisional application Ser. No. 60/222,139, filed Jul. 31, 2000, the entire contents of which is incorporated herein by reference in its entirety.

1. INTRODUCTION

The present invention is directed to methods and compositions for use of homologous recombination for directed evolution, gene reassembly, and directed mutagenesis. One aspect of the present invention relates to methods and compositions for use of bacterial conjugative transfer and homologous recombination for directed evolution, gene reassembly, and directed mutagenesis.

2. BACKGROUND OF THE INVENTION

Evolution can be viewed as an algorithm wherein a sequence gives rise to variants and a selection performed on that derivative pool allows for the survival of progeny with an incremental enhancement of the selected trait (Daniel C. Dennett, *Darwin's Dangerous Idea*, Touchstone, New York, N.Y. 1995). Iterative cycles of the process drive the production of increasingly refined embodiments of the selected trait. In popular models of natural evolution the global "fitness" of the organism is the driving selective force. Beginning at the dawn of civilization man has intervened in the process to exert selections on potential food corps and animals, not for the fitness of the organism, but rather for utility to his kind. This is a "directed evolution".

In recombinant DNA technologies, individual genes can be isolated and expressed in foreign host organisms allowing the controlled production of specific gene products. This ability forms the basis of the biotechnology industry, with applications in medicine, agriculture and various chemical industries (see, e.g., Evens and Witcher, 1993, Ther. Drug Monit. 15(6):514–20; Steve Prentis, Biotechnology: a new industrial revolution, G. Braziller, NY, NY 1984; Symposium on Biotechnology for Fuels and Chemicals, Totowa, N.J.: Humana Press, 1997). With recombinant DNA technologies, and the isolation of individual genes directed evolution procedures can be applied to these isolated genes. The term "directed evolution", as commonly used, applies to efforts made to improve the characteristics of a gene product with a particular commercial end in mind (Marrs et al., 1999, Curr. Opin. Microbiol 2(3):241–5), although in some instances the term has been applied to groups of genes defining a pathway (Wackett, 1998, Ann. N Y Acad. Sci. 864:142–52).

The first efforts to accomplish this involved the application of various mutagenesis procedures that introduce changes at single, or at times several, residues of the coding sequence (Kuchner and Arnold, 1997, Trends Biotechnol. 12:523–30). Such efforts have reported some success, albeit, limited. The number of potential changes to be explored is immense, vastly exceeding an experimenter's ability to produce and analyze them. It is clear that most changes are detrimental while only rare alterations yield enhancements in desired trait.

More recently, specialized PCR technologies have been applied to the problem of directed evolution (Stemmer, 1994, Proc. Natl. Acad. Sci. 91:10747–51). The most popular version, primerless PCR or so-called sexual PCR, allows for the re-assortment, or "shuffling," of closely related sequences. Briefly, a set of related gene sequences are fragmented, denatured, allowed to reanneal, and PCR extension is then performed through a number of cycles to reconstruct unit length genes. This process produces novel sequences that are complex permutations of the substrates. This process has proven to produce genes with significantly varied characteristics, and in many instances phenotypes dramatically improved for selected properties (e.g., Chang et al., 1999, Nat. Biotechnol. 8:793–7). In a set of experiments with a related family of β-lactamases, mutagenesis was compared directly with shuffling. The shuffling procedure proven to dramatically enhance resistance to a novel β-lactam (500-fold) where only modest improvements (8-fold) were noted in with mutagenesis alone (Crameri et al., 1998, Nature 391:288–91). Both mutagenesis and re-assortment sample an array of potential variants. When sampling re-assorted variants, the set of sampled sequences contains variants that are composed of sequence stretches that have themselves been "pre-selected," over evolutionary time scales, for function. This is in contrast to the sequences derived from mutagenesis where the combinations are likely to be encountered for the first time without "pre-selection." The hypothesized "pre"-selection aspect of this re-assortment procedure may allow for the apparently more productive nature of the so-called shuffling strategy.

Although "gene shuffling" has had some success and can be credited with popularizing the notion that cloned genes can be tailored to provide more useful variants through directed evolution procedures, it has clear limitations that make alternative strategies desirable. For example, one major shortcoming of "shuffling," or more precisely, random complex permutation sampling, is that information about a particular member of a combinatorial set only becomes accessible when the exact identity of that member is revealed. When complex permutations are sampled randomly, as in so-called gene shuffling, any information about the context of the sample is lost until its identity is revealed, following sequence determination. Furthermore, random permutation sampling through primeness PCR is a process that requires all subsequent iterations to repeat the enzymatic steps of the process: DNA isolation, DNA fragmentation, PCR reconstruction, and product cloning. A faster and more cost-effective procedure would be desirable.

Plasmid-based recombination has previously been used as an approach for producing novel genes (Piotukh et al., 1992, Molekulyarnaya Biologiya 26(4) part 2:601–604) used homologous recombination to construct hybrid metalloproteinases. This approach used direct repeat recombination, a process requiring only a single crossover event. Such recombination can produce novel genetic arrangements, but each round of iteration requires re-cloning of the sequences targeted for the recombination process, and reagents used for one event cannot reused or archived for subsequent procedures. Although a highly efficient process, this type of recombination does not lend itself to combinatorial reassortments or multiuse libraries.

Citation of a reference herein shall not be construed as an admission that such is prior art to the present invention.

3. SUMMARY OF THE INVENTION

The present invention provides methods and compositions for directed gene assembly ("DGA") that generate pluralities of divergent DNA molecules that can be used for functional analysis and directed evolution of genes ("target genes") in a laboratory setting. In these methods, a vector-borne donor molecule provides sequences that recombine with sequences of a vector-borne target molecule through homologous recombination to direct the assembly of divergent DNA molecules. In the present invention the directed assembly is achieved independently of the phenotypic characteristics encoded by the target sequences. Rather, selection is based on marker sequences physically linked to the target sequences. The resultant variant target molecules make possible a variety of subsequent selections or screens that may be executed on a diverse plurality of the recombinant products. Such subsequent screens can often be executed in a second host organism (other than the host in which the recombination event is selected) where prior enrichment for the recombinant product is required to make the process tractable.

Such bimolecular homologous recombination events allow for substrates of the process to be used repeatedly in iterative combinatorial exchanges. With respect to such iterations, the present invention involves directed, rather than random, iterative exchanges based on information obtained by analysis of the variants obtained in the previous iteration(s). Since the substrates are vectors that replicate in a host cell, e.g., a bacterium, they can be archived. For example, information about the potential function of substrates of the process may be deliberately sought by directing exchanges with sequences encoding structurally or empirically characterized target proteins.

The combination of archival and repeated uses results in historical information that leads to databases. For example, the present invention can be employed to create collections of protein structural domains that may be employed in directed evolution procedures that take into account increasing information about protein structure.

In its simplest form, the present invention involves a vector-based system that works through direct pair-wise exchanges between a donor and a target. This is in marked contrast to exchanges that can be catalyzed in primeness PCR strategies where multiple parents are made to participate in an exchange resulting in complex permutation sampling. In general, complex permutation sampling is not desirable because it only provides useful information from those members of a library for which full sequence information is determined, and as a consequence is not a powerful strategy for guiding subsequent iterative rounds. Unlike the PCR strategy, the DGA donor/target strategy of the invention proceeds in a logical and directed manner based on a systematic search where the iterative rounds involve mixing cells, e.g., bacteria, without new rounds of molecular biology procedures.

Advantages of the methods of the present invention are exemplified in Section 6, infra. Generation of variants of bacterial subtilisins, which are serine proteases that cleave polypeptides, using DGA produced a >95% yield of variants with functional protease activity (see, e.g., Section 6.6.2). This result can be contrasted with results reported for PCR-based shuffling of subtilisin sequences (Ness et al., 1999, Nature Biotechnology 17: 893–896). In the PCR-based shuffling experiments, only 6% of the resultant products showed protease activity. Thus, DGA methodology, which produces functional variants, significantly reduces the burden of labor-intensive assays required to screen against the 94% inactive products from the PCR procedure.

The donor/target selection described herein is based on the placement of a negative selection sequence into a position in the target sequence where the directed substitution is desired. The process is designed to take advantage of the in vivo biological process of homologous recombination. Three kinds of reagents are required for this process: (1) a donor DNA, (2) a target DNA and (3) a negative selection insert in the target DNA in the region where DNA segment replacement is desired. In one embodiment, the product of the homologous recombination is selected for directly, i.e., in a one-step process. In a more preferred embodiment, a two-step procedure is used to select for the product of homologous recombination, which entails selection of an intermediate state in the process followed by selection of the product of homologous recombination. In such an embodiment, the intermediate state is one in which the target cell contains both the donor vector and the target vector. Without wishing to be bound by any theory or mechanism, it is believed that this intermediate state more particularly involves an intermediate of the homologous recombination process referred to as a co-integrant. In the latter embodiment, a fourth element is required, namely a positively selectable sequence in the donor DNA to allow for selection of the intermediate state.

The invention encompasses, first, a method for generating a population of variant sequence modules in cells, e.g., bacterial cells, said method comprising: (a) transferring a donor vector into a target cell which is capable of homologous recombination, wherein (i) said donor vector comprises a donor recombination module comprising, in the following order from 5' to 3': a first donor DNA sequence and a second donor DNA sequence; and (ii) said target cell comprises a target vector comprising a target recombination module comprising, in the following order from 5' to 3': a first target DNA sequence; a negatively selectable marker; and a second target DNA sequence, wherein said first donor DNA sequence is homologous to said first target DNA sequence, and said second donor DNA sequence is homologous to said second target DNA sequence; and (b) selecting for a population of target cells which do not contain the negatively selectable marker, so that a population of variant sequence modules in cells, in particular, the target cells is generated. Generally, selecting for target cells that do not contain the negatively selectable marker is accomplished by subjecting the cells to conditions that do not allow growth of donor cells or of target cells that still contain the negatively selectable marker (i.e., have not undergone recombination with the donor vector resulting in loss of the negatively selectable marker). To ensure loss of donor cells, for example, a selectable marker (e.g., a tetracycline resistance-encoding element) can be included in the chromosomal background of the target cell, but be absent from the donor cell. Imposing appropriate selective pressure (e.g., inclusion of tetracycline) results in selected loss of donor cells. In a variation of this method, the target recombination module is present in the target cell integrated into the target cell genome. Preferably, the target recombination module is integrated in a manner that readily allows excision or isolation of the module out genome, i.e., via flanking unique restriction sites or by specific amplification of the module.

In another embodiment, the invention provides a method for generating a population of a variant sequence modules in cells, e.g., bacterial cells, said method comprising:(a) transferring a donor vector into a target bacterial cell which is capable of homologous recombination, wherein (i) said donor vector comprises a donor recombination module comprising, in the following order from 5' to 3': a first non-functional fragment of a positively selectable marker; a first donor DNA sequence; and a second donor DNA sequence; (ii) said target cell comprises a target vector comprising a target recombination module comprising, in the following order from 5' to 3': a second non-functional fragment of the positively selectable marker; a first target DNA sequence; and a second target DNA sequence, wherein said first donor DNA sequence is homologous to said first target DNA sequence, and said second donor DNA sequence is homologous to said second target DNA sequence, and recombination between said first non-functional fragment of the selectable marker and said second non-functional fragment of the selectable marker results in a functional selectable marker; and (b) selecting for a population of target cells which contain a functional positively selectable marker, so that a population of a variant sequence modules in the cells is generated. In a variation of this method, the target recombination module is present in the target cell integrated into the target cell genome. Preferably, the target recombination module is integrated in a manner that readily allows excision or isolation of the module out genome, i.e., via flanking unique restriction sites or by specific amplification of the module.

The cells undergoing DGA, i.e., target cells into which the donor vector has been transferred, are subjected to conditions that allow homologous recombination to take place. Conditions that allow homologous recombination to occur merely refer to standard growth or maintenance conditions for the particular cells being used in the particular instance.

In a preferred embodiment, the donor vector and target vector of the foregoing methods are present in bacterial cells. In one embodiment of the method, the bacterial cell is an *E. coli* cell. In other embodiments, the bacterial cell is a naturally transformable cell such as *Acinetobacter calcoaceticus*, *Haemophilus influenzae*, or *Neisseria meningitidis*. In another preferred embodiment, the donor vector and the target vector are present in a bacterial cell, and said transferring is by conjugative transfer of at least the donor recombination module of the donor vector from the donor cell to the target cell. In other embodiments, the donor vector is transformed into the target cell or is transferred into the target cell via a phage particle.

In another preferred embodiment, the donor vector further comprises a positively selectable marker. Where the donor vector further comprises a positively selectable marker, the methods of the present invention preferably further entail, between step (a) and step (b): (a') selecting for a population of target cells, e.g., bacterial cells, with the donor vector, by selecting for the presence of the positively selectable marker in the donor vector.

In one embodiment, these methods further comprise the step of: (c) selecting said population of target cells which do not contain the negatively selectable marker for a desired phenotype. In another embodiment, the invention provides a method for optimizing a phenotype comprising the above-mentioned method, further comprising: the step of (d) repeating steps (a)–(c), wherein the target recombination module used in step (d) is derived from a target cell selected in step (c), and said selection is based on information obtained from the analysis of the variant sequence modules obtained in step (c).

In another embodiment, the donor vector further comprises a third donor sequence, located 3' to the first donor sequence and 5' to the second donor sequence. In another embodiment, the target recombination module of step (d) is identical to the target recombination module of step (a). In another embodiment, the target recombinant module of step (d) is different from the target recombination module of step (a). In yet another embodiment, the methods further comprise, prior to step (a), the step of mutagenizing the donor DNA vector. In one embodiment, the step of mutagenizing the donor vector is carried out in vitro. In another embodiment, the step of mutagenizing the donor molecule is carried out in vivo.

In another embodiment, the negatively selectable marker comprises a conditionally lethal sequence and selecting the recombinant comprises selecting against said conditionally lethal sequence. In yet another embodiment, the negatively selectable marker of the target recombination module is a polar insert sequence which prevents expression of a downstream reporter gene, such that deletion of said polar insert results in expression of the reporter gene, and the step of selecting for a population of target cells which do not contain the negatively selectable marker comprises detecting or selecting for expression of said reporter gene. In various embodiments, the polar insert is a Tn5 or a Tn10 sequence.

In certain embodiments, the negatively selectable marker can be selected against on the basis of its physical properties. Such selection is referred to herein as "molecular selection." In one such embodiment, the negatively selectable marker in the target recombination module comprises a unique restriction endonuclease recognition site, and selection for a recombinant variant comprises selecting against molecules with the restriction endonuclease recognition site. In another such embodiment, the negatively selectable marker is selected against on the basis of its size, said selection comprising amplifying DNA from cells to identify and isolate sequences comprising recombinant target modules that have lost the negative selection insert.

In various embodiments of the present invention, there is at least 75%, at least 80%, more preferably at least 85%, yet more preferably at least 90%, and most preferably at least 95% sequence identity between the first donor DNA sequence and the first target DNA sequence and between the second donor DNA sequence and the second target sequence.

In a preferred embodiment of the invention, the donor vector is a suicide vector.

The invention further provides kits suitable for directed assembly of a target DNA molecule. These kits comprise donor vectors, donor cells, target vectors and/or target cells of the invention.

In one embodiment, such a kit comprises in one or more containers: a) a donor vector comprising a donor recombination module comprising, in the following order from 5' to 3': a first donor DNA sequence and a second donor DNA sequence, and b) a target cell which is capable of homologous recombination, said cell comprising a double-stranded DNA target vector useful for directed assembly of a target DNA molecule of interest, said target vector comprising a target recombination module comprising, in the following order from 5' to 3': a first target DNA sequence; a negatively selectable marker; and a second target DNA sequence, such that said first donor DNA sequence is homologous to said first target DNA sequence, and said second donor DNA sequence is homologous to said second target DNA sequence.

In another embodiment, such a kit comprises, in one or more containers: a) a donor vector, comprising a donor recombination module comprising, in the following order from 5' to 3': a first non-functional fragment of a positively selectable marker, a first donor DNA sequence, and a second donor DNA sequence; b) a target cell comprising a target vector comprising, in the following order from 5' to 3': a second non-functional fragment of the positively selectable marker; a first target DNA sequence; and a second target DNA sequence, wherein them said first donor DNA sequence is homologous to said first target DNA sequence, and said second donor DNA sequence is homologous to said second target DNA sequence, and recombination between said first non-functional fragment of the selectable marker and said second non-functional fragment of the selectable marker results in a functional selectable marker. In one embodiment, the donor vector is present within a cell, i.e., a donor cell.

In one kit embodiment, the donor vector further comprises a third donor sequence, located 3' to the first donor sequence and 5' to the second donor sequence. In another kit embodiment, the donor vector further comprises a positively selectable marker. In a preferred embodiment, the cells of the kit are bacterial cells, preferably E. coli cells or naturally transformable bacterial cells.

The invention further provides libraries suitable for the practice of directed gene assembly. Such libraries can be donor or vector libraries and can comprise a plurality of any of the donor or target vectors of the invention, including vectors comprising variant target sequences that have been produced via DGA. Such libraries can also comprise variant target gene or target gene sequences produced via DGA that no longer contain intervening selectable markers and encode variant target gene products, including optimized variant target gene products. Libraries can also comprise a plurality of archived sequences or modules, optionally present within cells.

The invention further encompasses databases of archived modules. An archived module, as used herein, refers to a donor DNA sequence or target DNA sequence, whether or not the donor or target sequence has undergone DNA or phenotype optimization, where the sequence comprising the archived module is known or has been demonstrated to encode a protein segment or domain that provides a particular function and has been stored and cataloged (archived).

The present invention still further provides a computer readable medium having a database recorded thereon in computer readable form, wherein said database comprises one or more module profiles and wherein each module profile describes a phenotype in a DGA assay, and wherein each module profile is associated with a particular vector in a particular target cell.

4. BRIEF DESCRIPTION OF THE FIGURES

FIG. 1. Features of the Donor Vector. FIG. 1 shows a donor vector (Section 5.1.1) comprising a recombination module (referred to as "bc"), described in Section 5.1.1.1; a selectable marker, described in Section 5.1.1.4; an origin of replication, which is preferably conditional and compatible with the target vector, described in Section 5.1.1.3; and, optionally, where the donor vector is to be transferred into the target cell by means of conjugation, conjugative transfer sequences as described in Section 5.1.1.2.

FIG. 2. Features of the Target Vector. The left panel FIG. 2 shows a target vector Section 5.1.2) comprising a target recombination module ("ABCDE"), described in Section 5.1.2.1; a selectable marker and an origin of replication for propagation of the target vector in the target cell (Section 5.1.2.2), and, optionally, an additional selectable "shuttle" origin of replication and selectable marker that can be used to propagate the vector in a different cell (Section 5.1.2.2). The right panel shows a target vector as in the left panel, further comprising negatively selectable marker galK, which is the galactokinase gene under the control of the galactose operator ("galOP"). This negatively selectable marker (see Section 5.1.2.1.1) imparts galactose sensitivity on target cells with a galE genotype that comprise the target vector.

Figure 3:
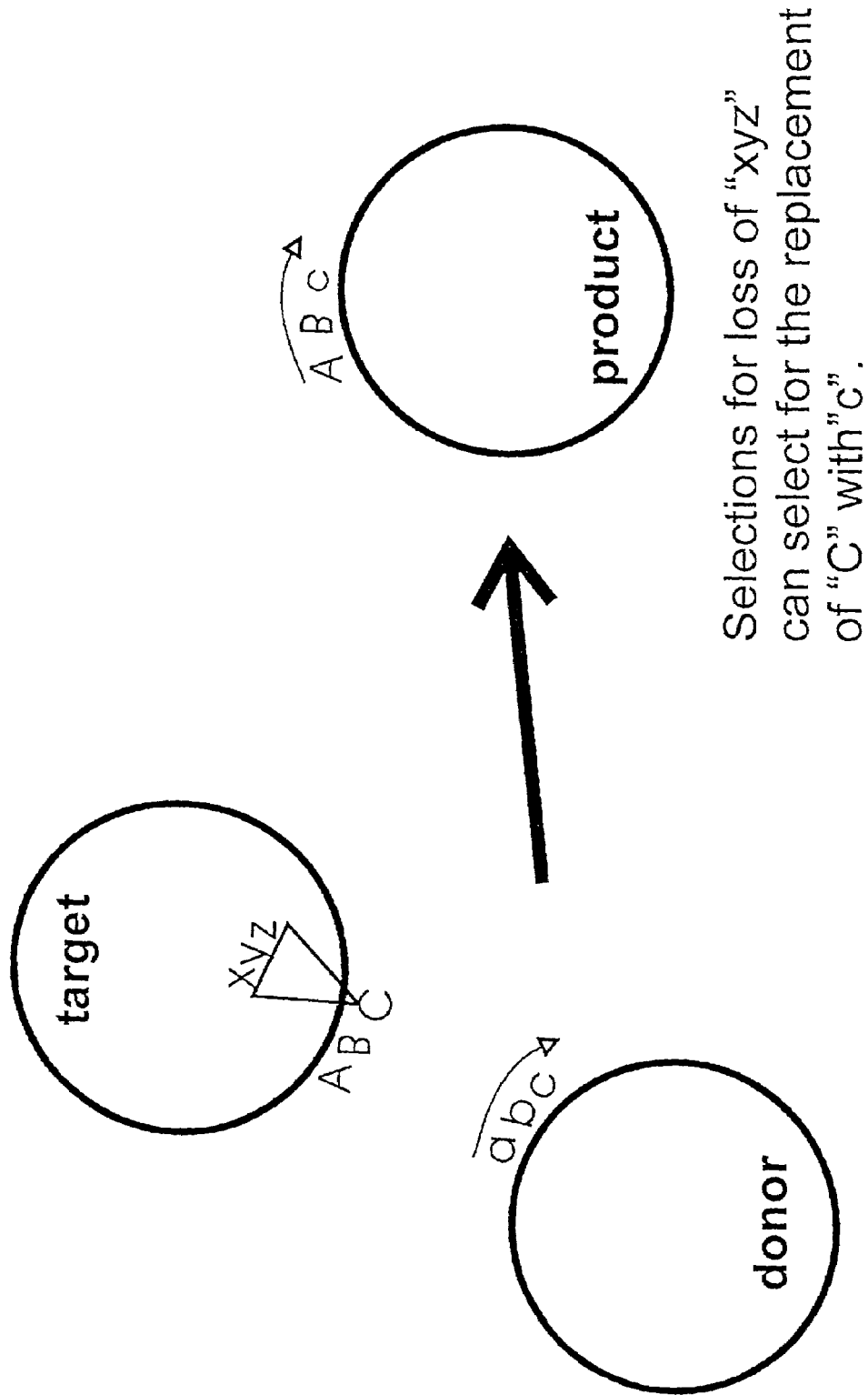

FIG. 3. Method for Selecting Recombinant Product: Selection Against Non-Recombinants. FIG. 3 shows how the product of a DGA event can be selected for (see Section 5.2) by selecting against a negatively selectable marker ("xyz") present in the target recombination module ("ABC"). A recombination event between the donor recombination module ("abc") in which the strand crossover sites flank the negatively selectable marker results in the generation of a variant target module ("ABc") lacking the negatively selectable marker. The negatively selectable marker can be selected against (see Section 5.2.1) to identify recombinant variant target vectors with variant target modules.

Figure 4:
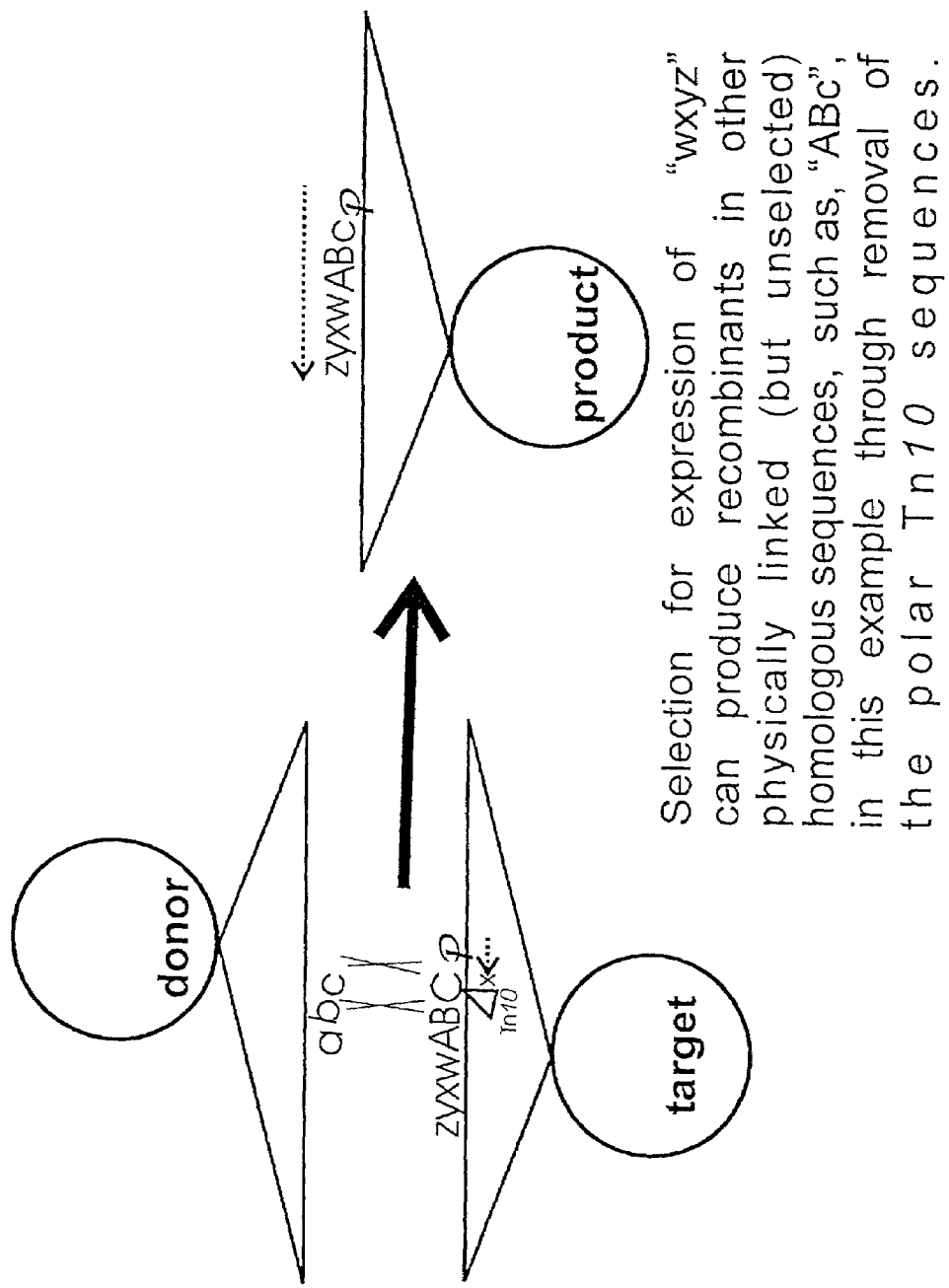

FIG. 4. Method for Selecting Recombinant Product: Elimination of Polar Sequence. FIG. 4 shows how the product of a DGA event can be selected for (see Section 5.2) by selecting against a polar sequence such as Tn10 present in the target recombination module ("ABC"). The target vector further comprises a promoter sequence on the 5' side of the target recombination module and a reporter gene ("wxyz") placed 3' of the target recombination module (see Section 5.1.2.1.1). The polar sequence inhibits expression of the reporter gene. A recombination event between the donor recombination module ("abc") in which the strand crossover sites flank the polar sequence results in the generation of a variant target module ("ABc") lacking the polar sequence. In the absence of the polar sequence, the reporter gene ("wxyz") can be transcribed and selected for (see Section 5.2.1) to identify recombinant variant target vectors with variant target modules.

Figure 5:
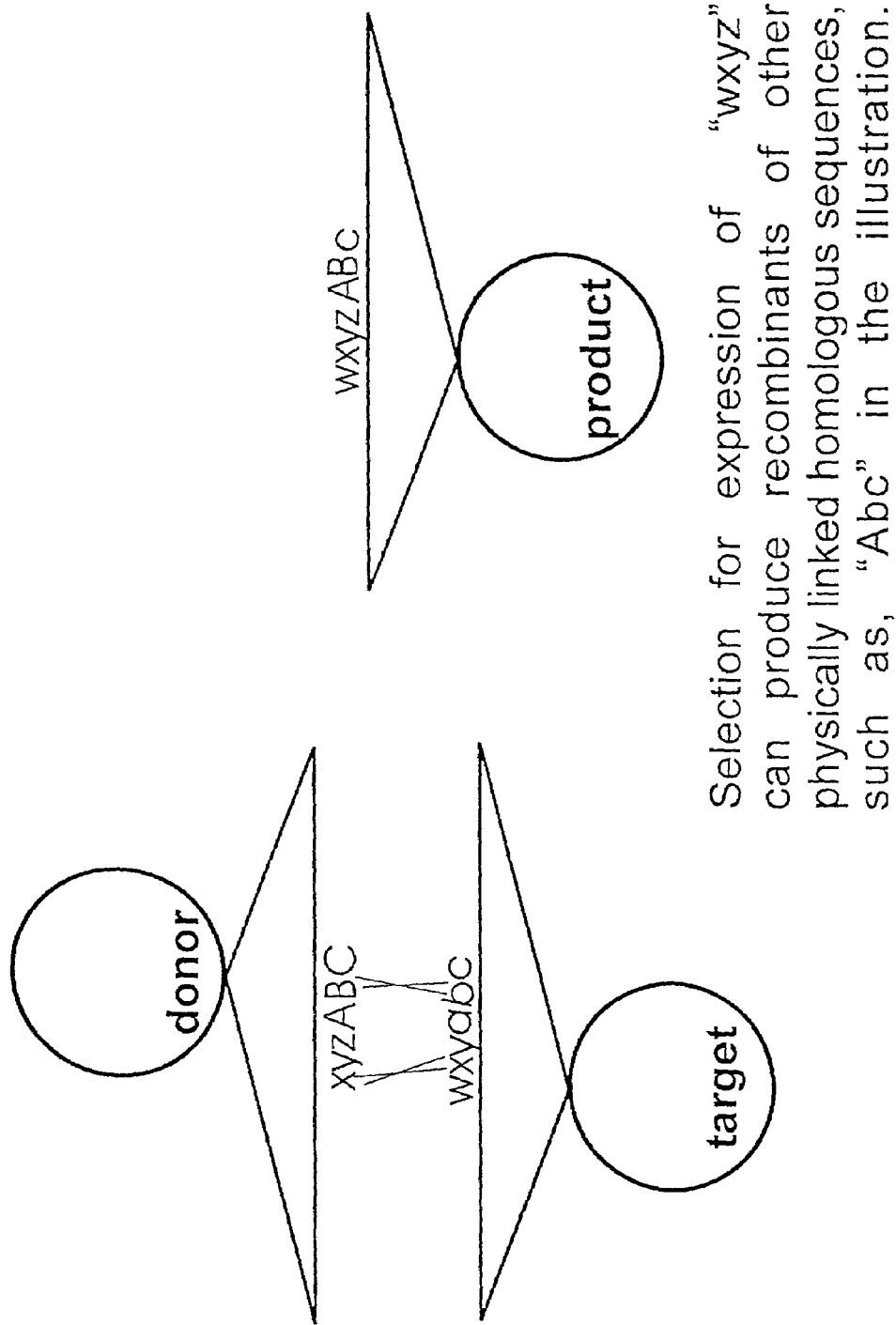

FIG. 5. Method for Selecting Recombinant Product: Reconstruction of Flanking Selectable Marker. FIG. 5 shows how the product of a DGA event can be selected for (see Section 5.2) by reconstruction of a reporter gene ("wxyz"), as described in Section 5.1.2.1.2. The target vector comprises a non functional fragment of the reporter gene ("wxy") and the donor vector comprises a second, complementary non-functional fragment ("xyz") of the reporter gene. A recombination event between the donor recombination module ("ABC") and the target recombination module ("abc") results in the generation of a variant target module ("ABc") and a functional reporter gene ("wxyz"), which can be expressed and selected for (see Section 5.2.1) to identify recombinant variant target vectors with variant target modules.

Figure 6:
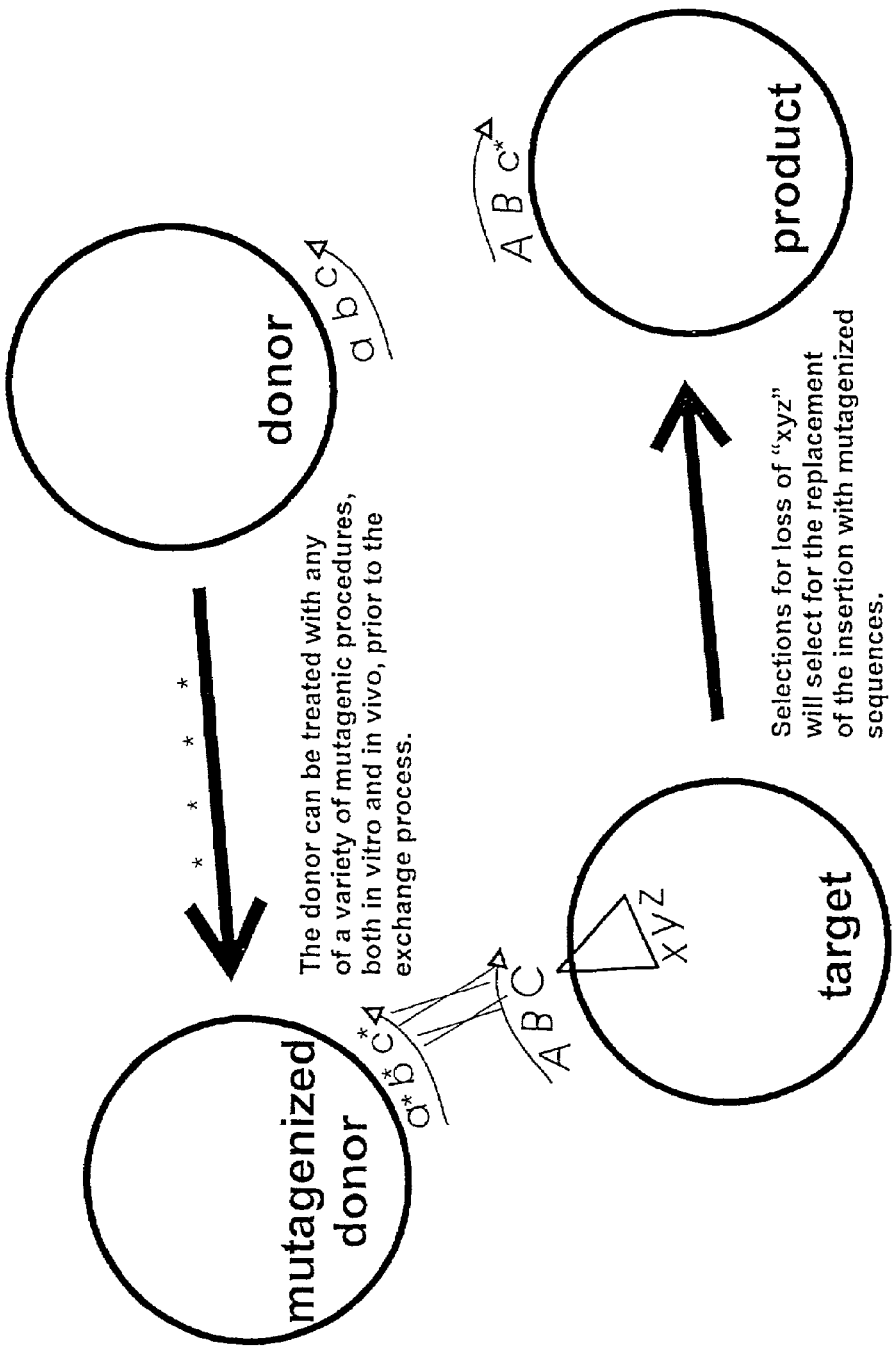

FIG. 6. Directed mutagenesis. FIG. 6 shows a DGA process essentially as described in FIG. 3, but where the donor is mutagenized (as described in Section 5.2) prior to DGA, to produce a mutagenized donor recombination module ("a*b*c*"). DGA using a mutagenized donor results in the variant target module "Abc*".

Figure 7:
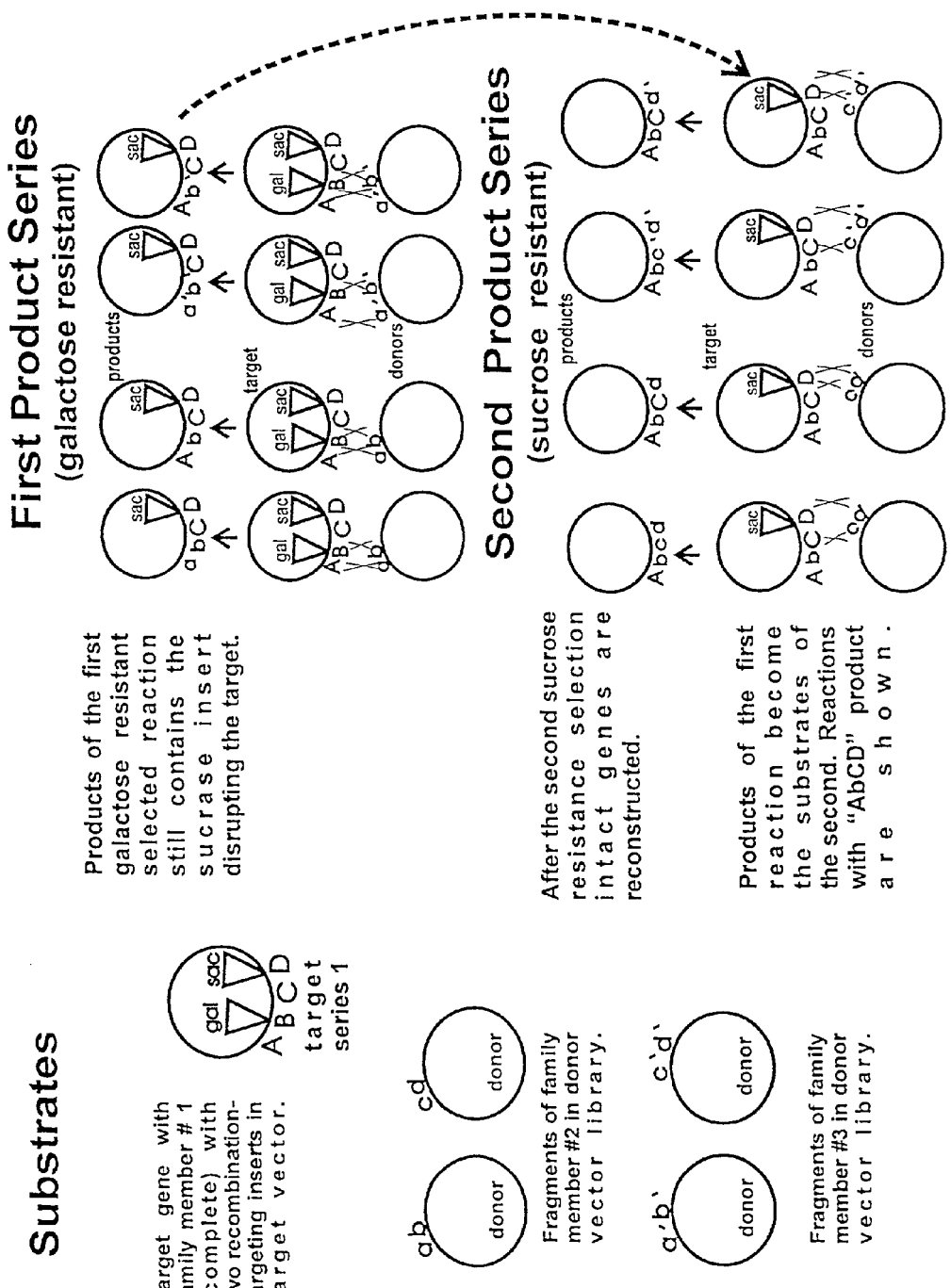

FIG. 7. Gene Family Re-Assortment. FIG. 7 shows how starting with a target recombination module ("ABCD") with two negatively selectable markers ("gal" and "sac") allows for 2 successive rounds of DGA, thereby generating greater diversity. In the example of FIG. 7, for each target recombination module ("ABCD"), the first round of DGA utilizes two related donor modules ("ab" and "a'b'") homologous to the "AB" portions of the target recombination module and the second recombination step utilizes another two related donor modules ("cd" and "c'd'") homologous to the "CD" portions of the target recombination module. Gene family re-assortment is described in Section 5.2.5.

Figure 8:
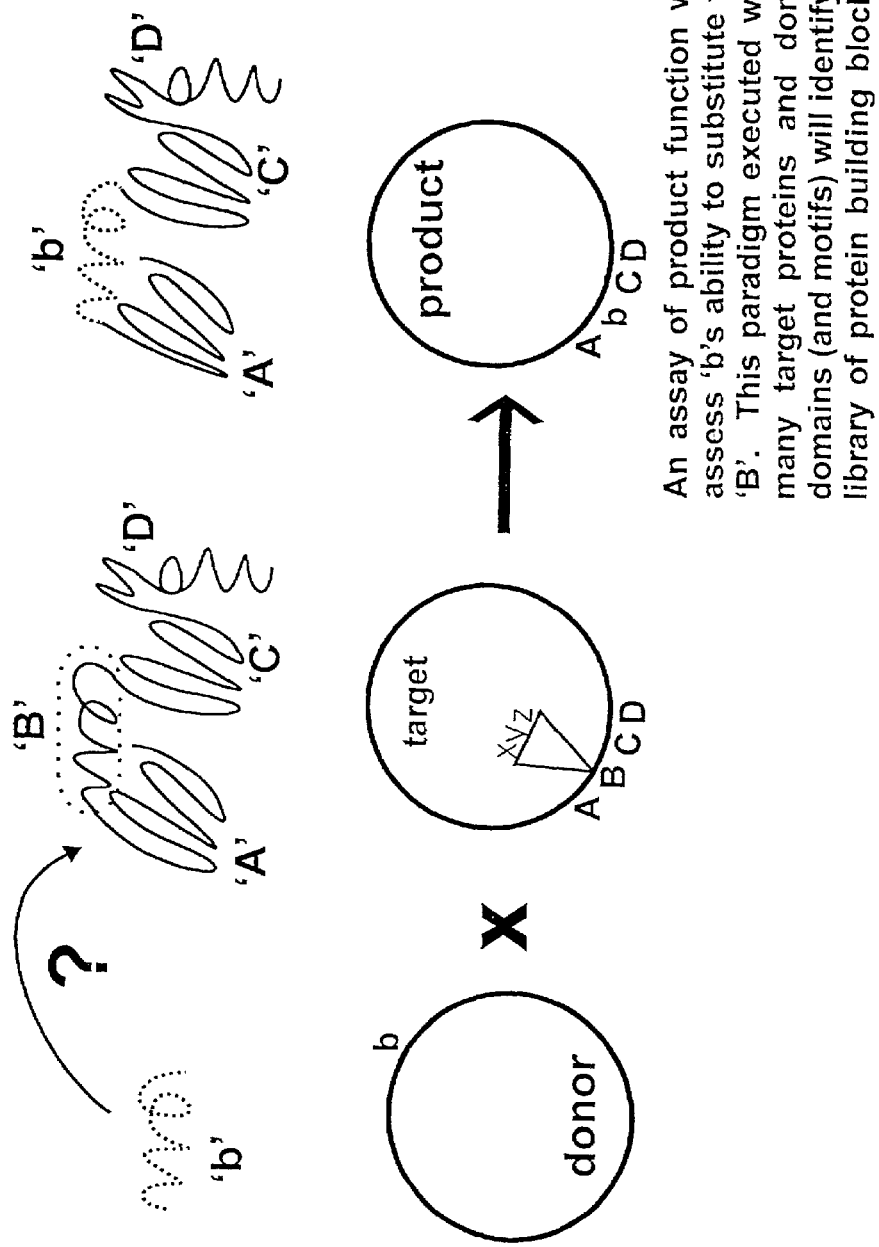

FIG. 8. Identification of structural motifs. FIG. 8 describes how a novel protein ("AbCD") can be generated by DGA starting with a target recombination module ("ABCD") comprising a negatively selectable marker in "B" and a donor recombination module "b". The activity of "AbCD" can be compared with the activity of "ABCD" to determine whether "b" can functionally substitute for "B". This information can be used to generate additional variants. See Section 5.2.5.

Figure 9:
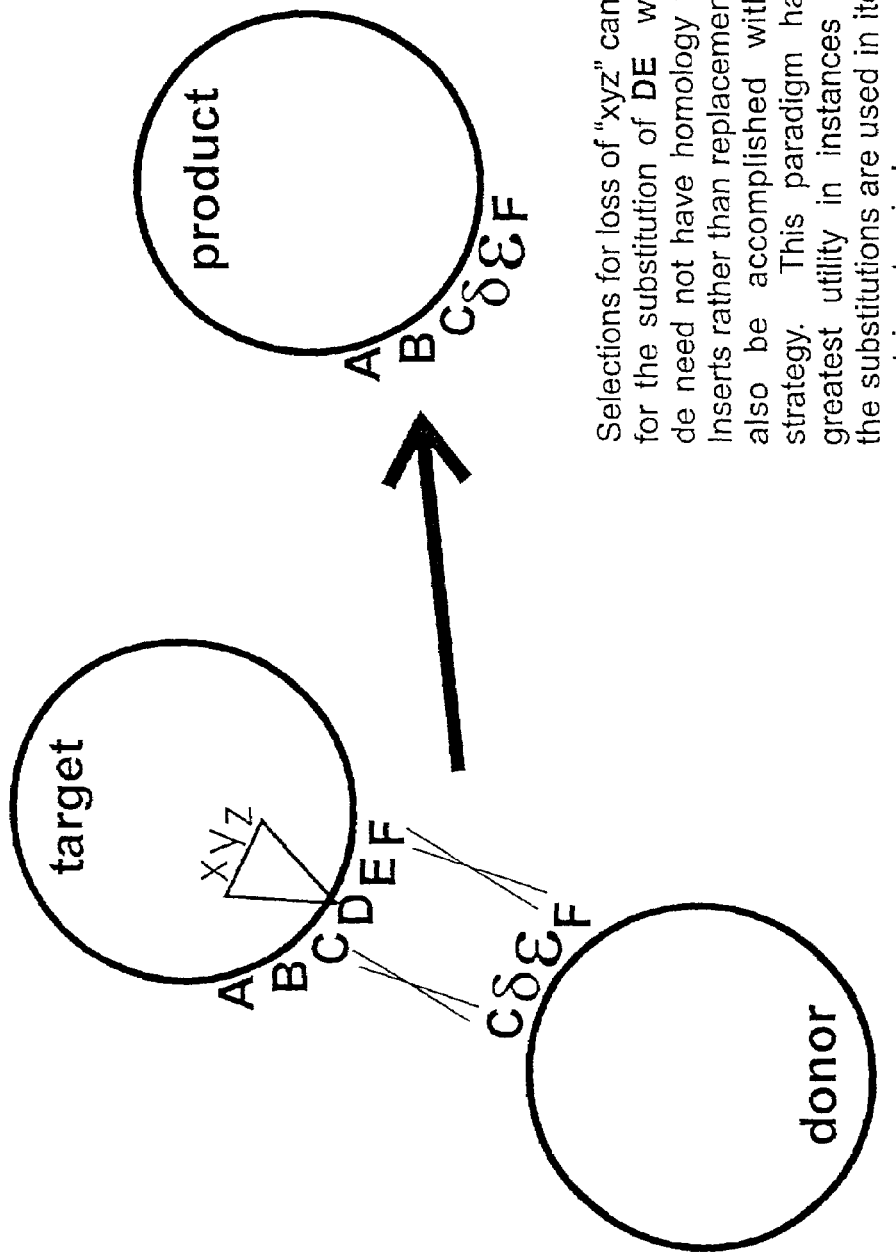

FIG. 9. Insertional acquisition and substitution. FIG. 9 shows how DGA can be utilized to replace sequences "DE" in the target recombination module ("ABCDEF", where a negatively selectable marker ("xyz") is inserted into "D") with non-homologous sequences "δ∈". This is achieved by subjecting the target recombination module to DGA with a donor recombination module ("Cδ∈F") in which the non-homologous sequences are flanked by homologous sequences ("C" and "F"). See Section 5.3.

Figure 10:
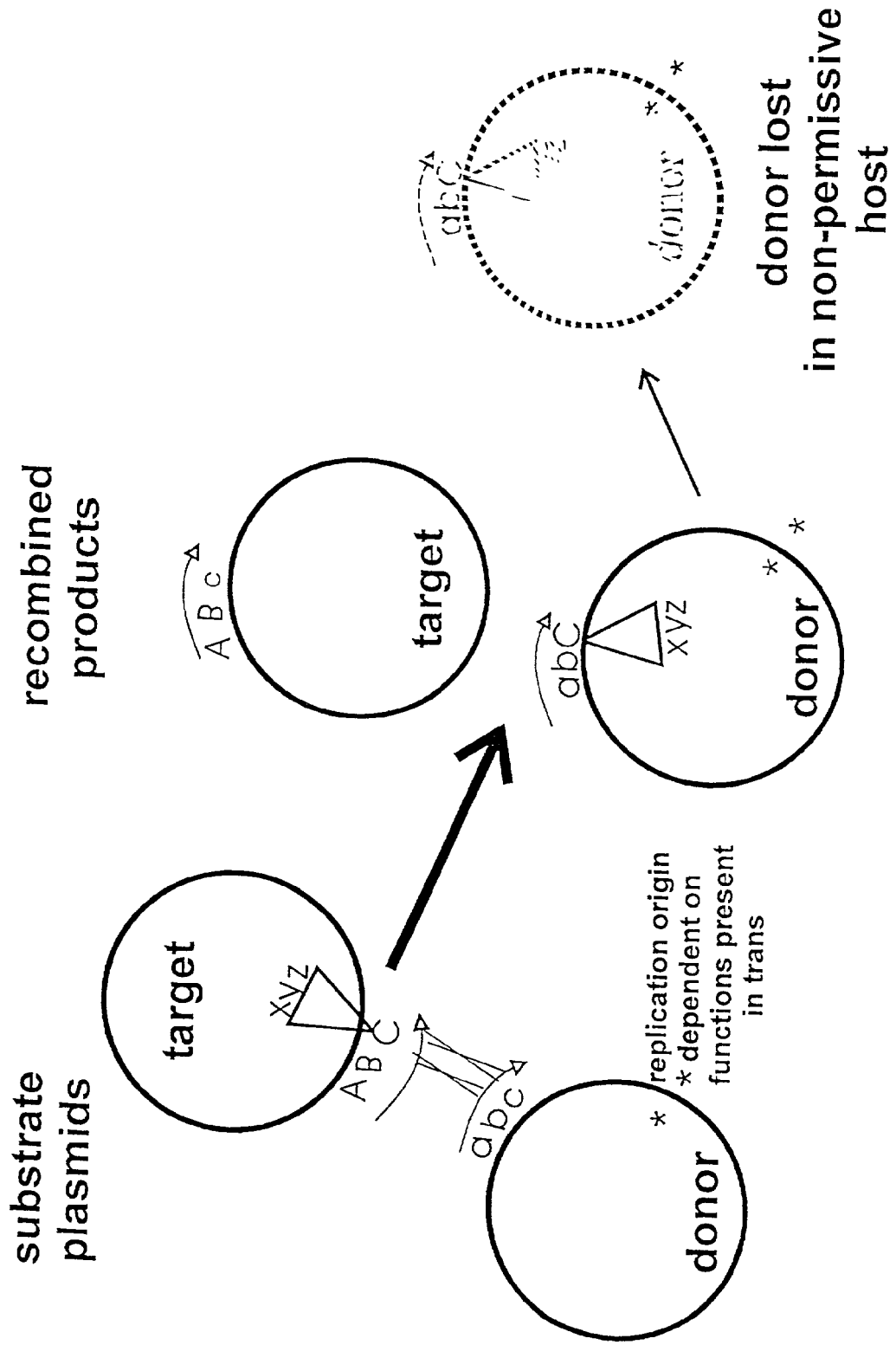

FIG. 10. Selection for Segregation of Donor Vector. FIG. 10 show a DGA process, essentially as described in FIG. 3, utilizing a "suicide" donor vector. A suicide donor vector has an origin of replication compatible with the cell in which the donor vector is propagated (e.g., a donor cell) but is incompatible with the target cell. This DGA configuration allows the elimination of recombined donor vectors following DGA.

Figure 11:
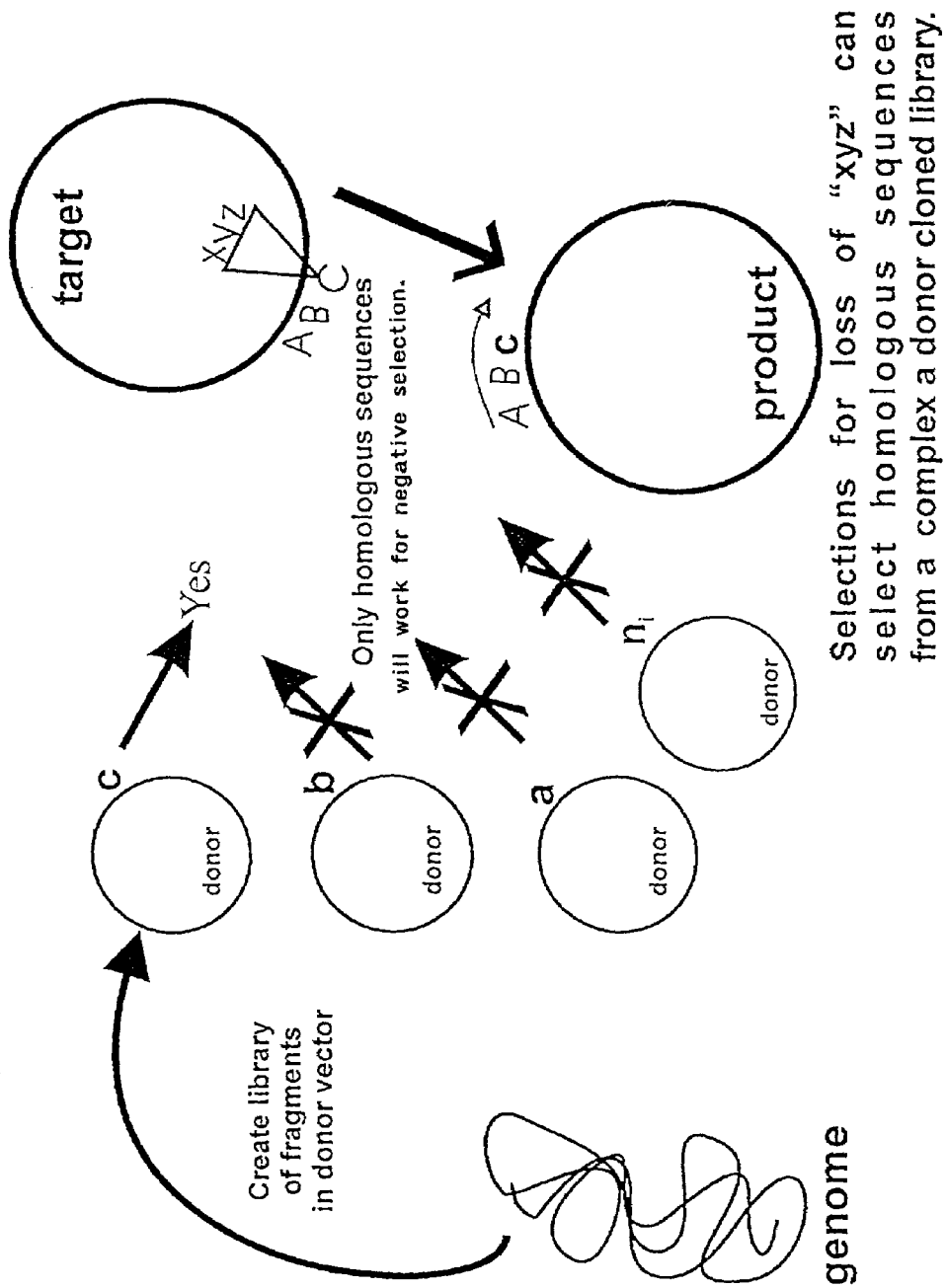

FIG. 11. Sequence isolation. FIG. 11 shows how DGA can be utilized to isolate novel homologous sequences to a target sequence of choice from a nucleic acid library. Nucleic acid sequences from a library (e.g., "c", "b", "a") are inserted as donor recombination modules into a donor vector. Using the negative selection method described in FIG. 3, only recombination events that result in deletion of the negatively selectable marker ("xyz") from the target recombination module ("ABC" comprising the negative selection marker in "C") are identified. In the example shown in FIG. 11, the donor recombination module "c" will recombine with the target recombination module to generate "ABc", thereby identifying "c" as a homologous sequence to "C". This method is described in Section 5.2.5.

Figure 12:
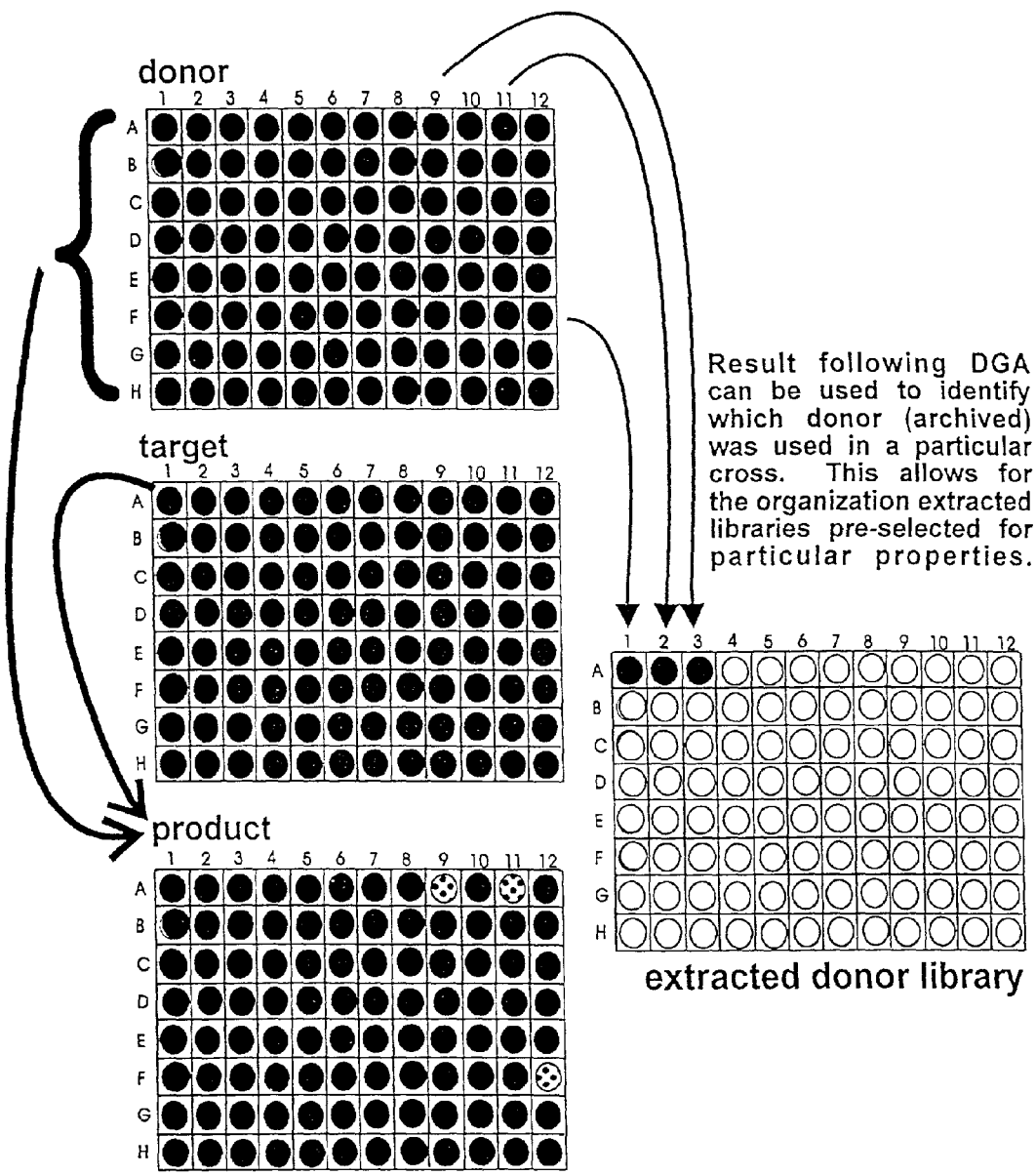

FIG. 12. Creation of extracted libraries. FIG. 12 shows an "extracted donor library", in which donors producing products with desired properties are set aside to produce the extracted library, which is a specialized library containing modules or sequences of similar or related function. See Section 5.3.

Figure 13:
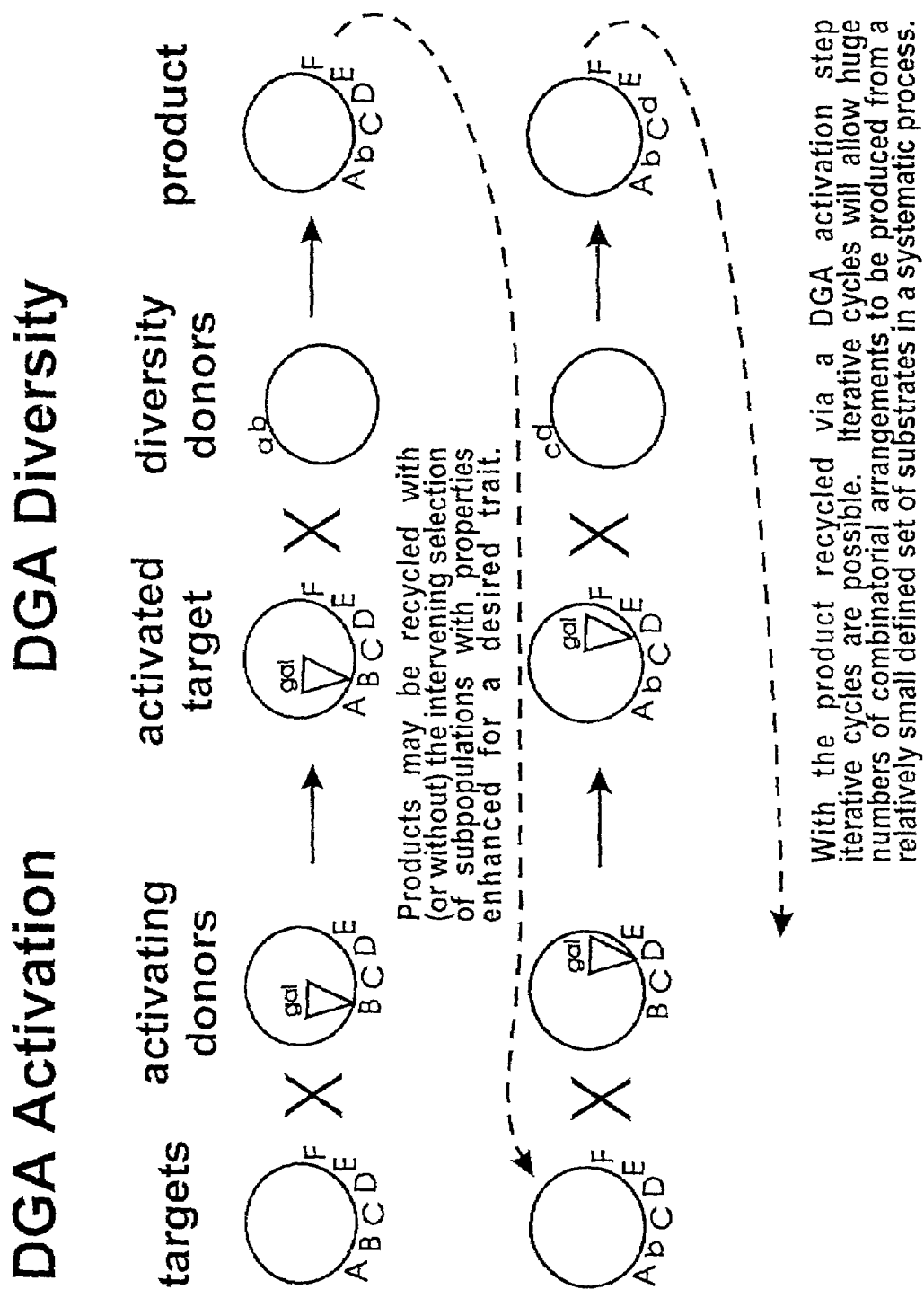

FIG. 13. Iterative cycling of Product to Target. FIG. 13 shows how a target recombination sequence ("ABCDEF") can be activated by insertion of a negatively selectable marker ("gal") by DGA in which the "activating" donor recombination module ("BCDE") comprises the negatively selectable marker in "B". After one round of DGA between the activated target ("ABCDEF" comprising the "gal" marker in "B") with a diversity donor ("ab"), which produces the variant "AbCDEF", the new product can be activated with another activating donor ("BCDE") with a negatively selectable marker in a different position (in "D"). A second round of DGA with a second diversity donor ("cd") produced yet another variant product ("AbCdEF"). This process can be repeated to produce large numbers of substrates for future rounds of DGA.

Figure 14:
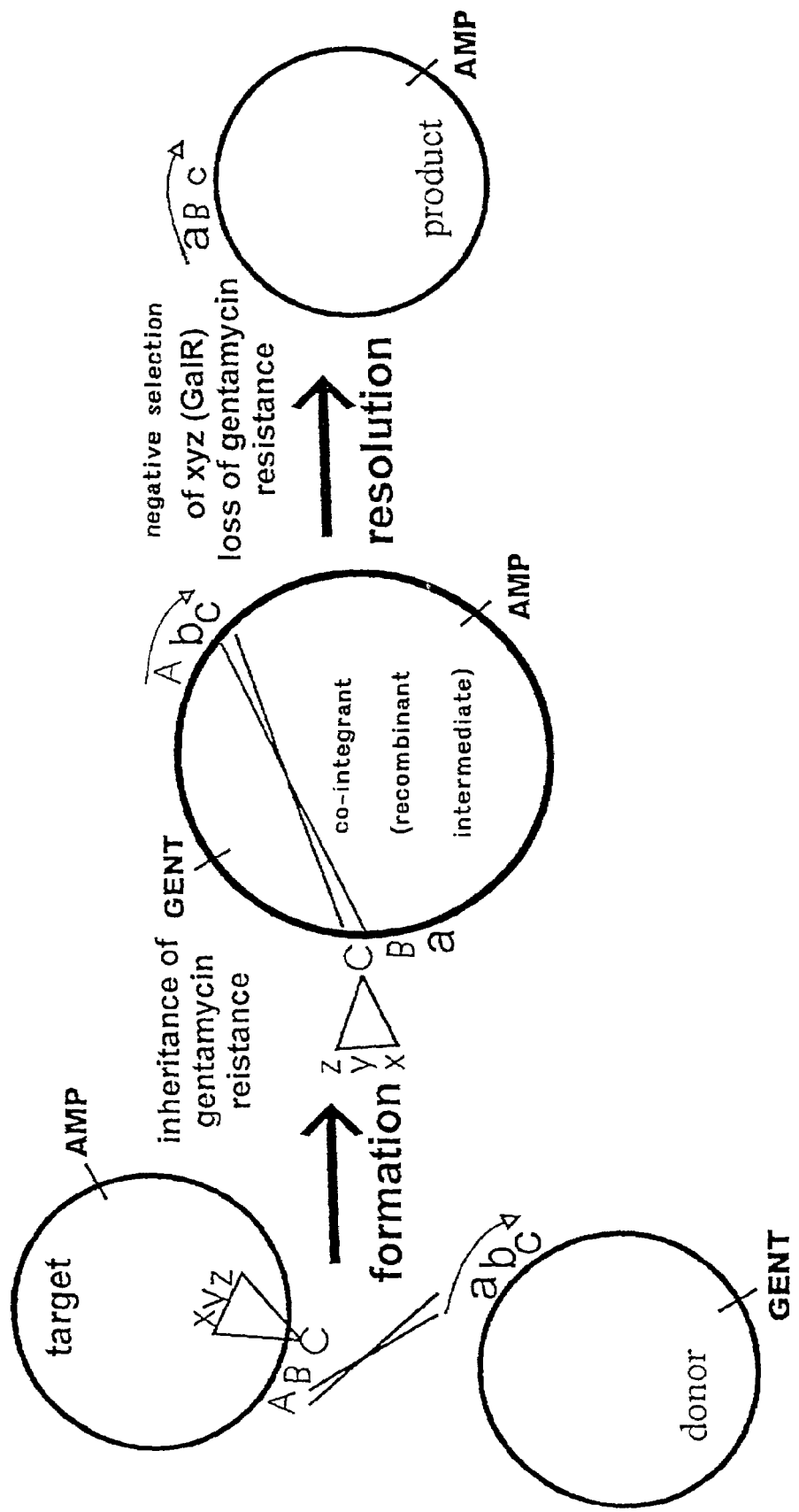

FIG. 14. Schematic of two step co-integrant formation and resolution. FIG. 14 shows the generation of a co-integrant, which is an intermediate of homologous recombination, which comprises target vector sequences (including an AMP selection cassette) and donor vector sequences (including a gentamycin resistance cassette). Selection against the negatively selectable marker ("xyz") in the target recombination module ("ABC") will select for recombination products of DGA. For further details, see Section 5.2.2.

Figure 15:
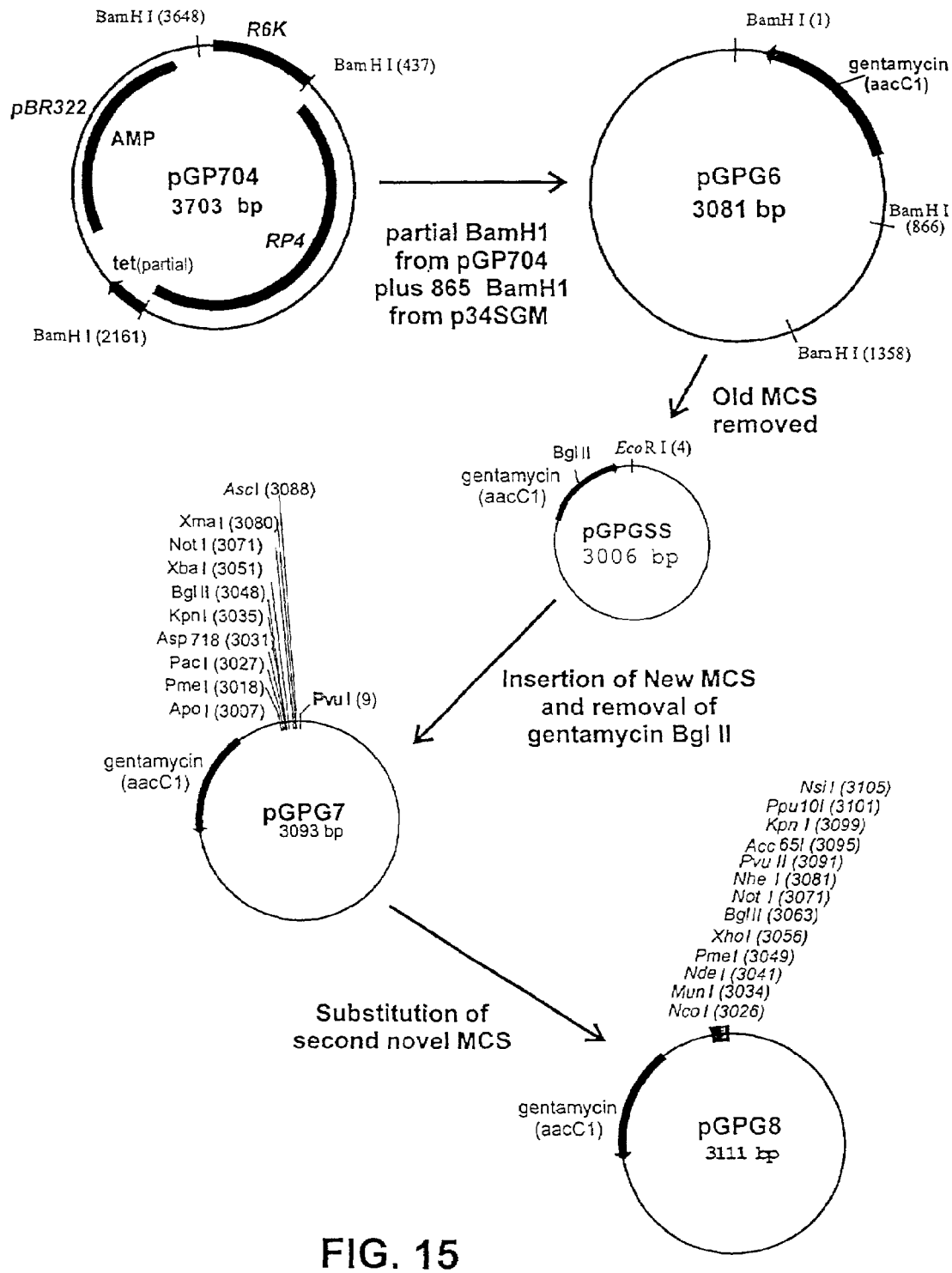

FIG. 15. Schematic of pGPG plasmid series creation and features. For additional details on the construction of the pGPG plasmid series, see Section 6.1.1.

FIG. 16 Sequence of 3A13 (SEQ ID NOs: 21 and 22) and 5A20 (SEQ ID NOs: 19 and 20) sequences in pGPG. For a description of these plasmids, see Section 6.1.2.

FIG. 17A–17B. Sequence of complete (A) *lichenformis* (SEQ ID NOs: 13 and 14) (5A36) and (B) *subtilis* (SEQ ID NOs: 15 and 16) (3A1) subtilisins in target vector. For details, see section 6.2.1.

Figure 18:
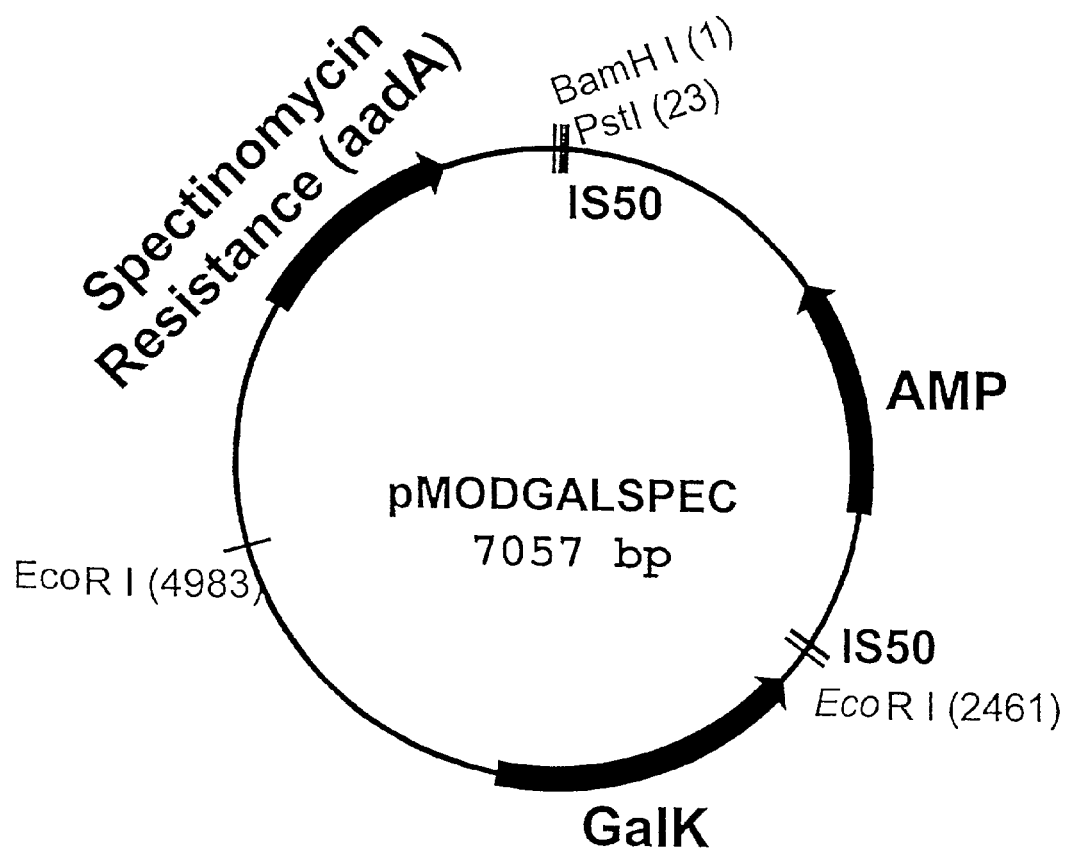

FIG. 18. Schematic representation of selectable/negative selection inserts. For details, see section 6.2.3.

Figure 19:
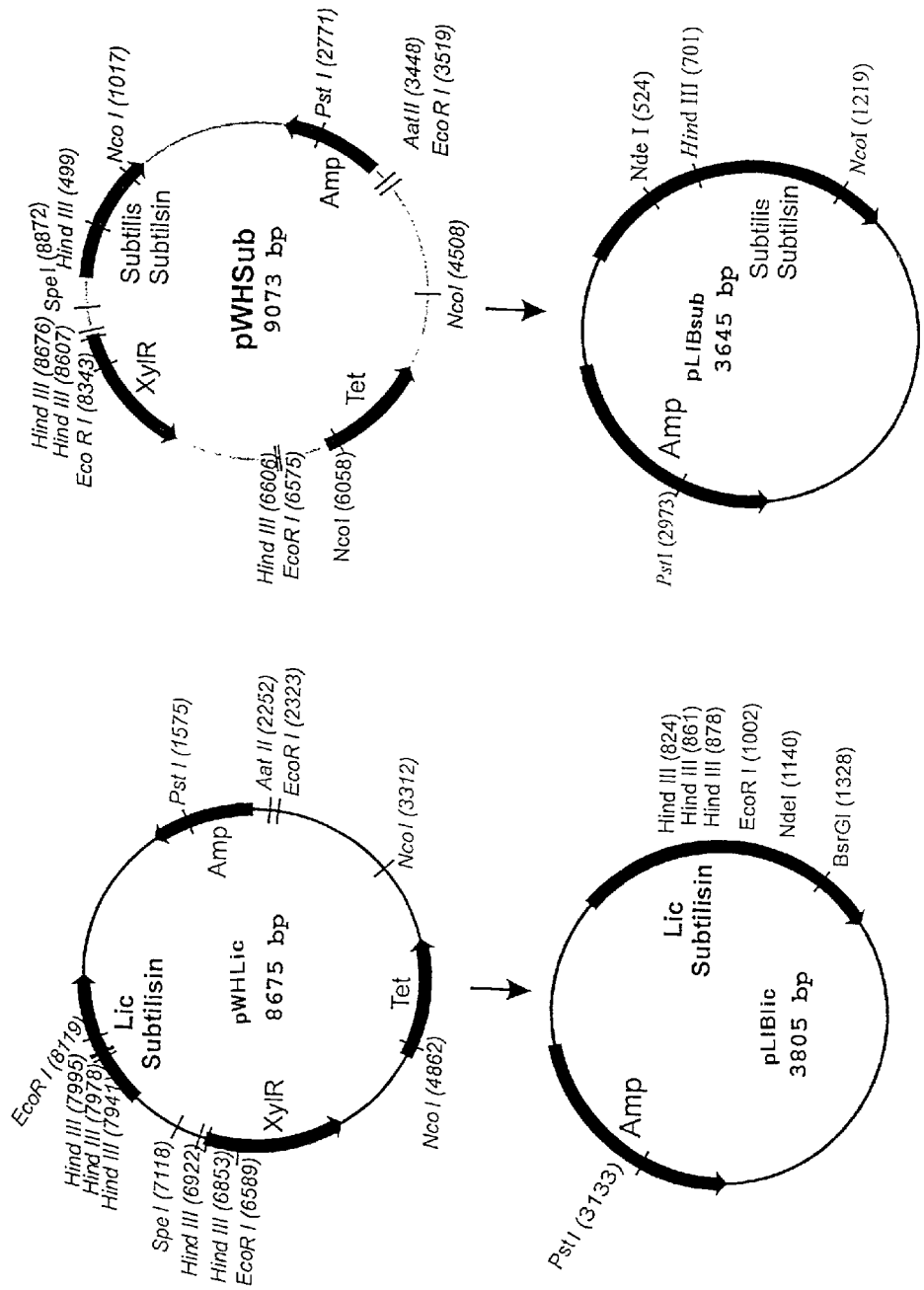

FIG. 19. Schematic representation of reduced target vectors. For details of these vectors, see Section 6.2.5.

Figure 20:
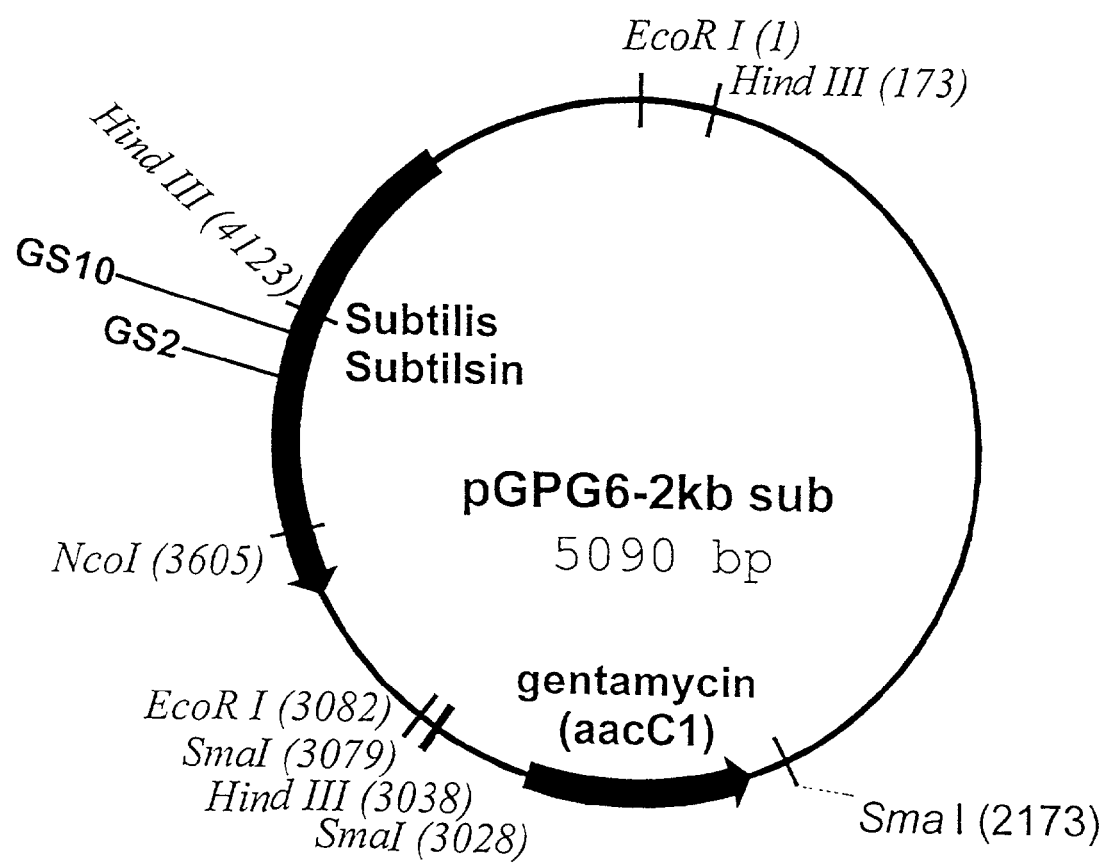

FIG. 20. Diagram of Gal-Spec and Kan-Suc inserts in target vectors. For details of these vectors, see Section 6.2.4.

Figure 21:
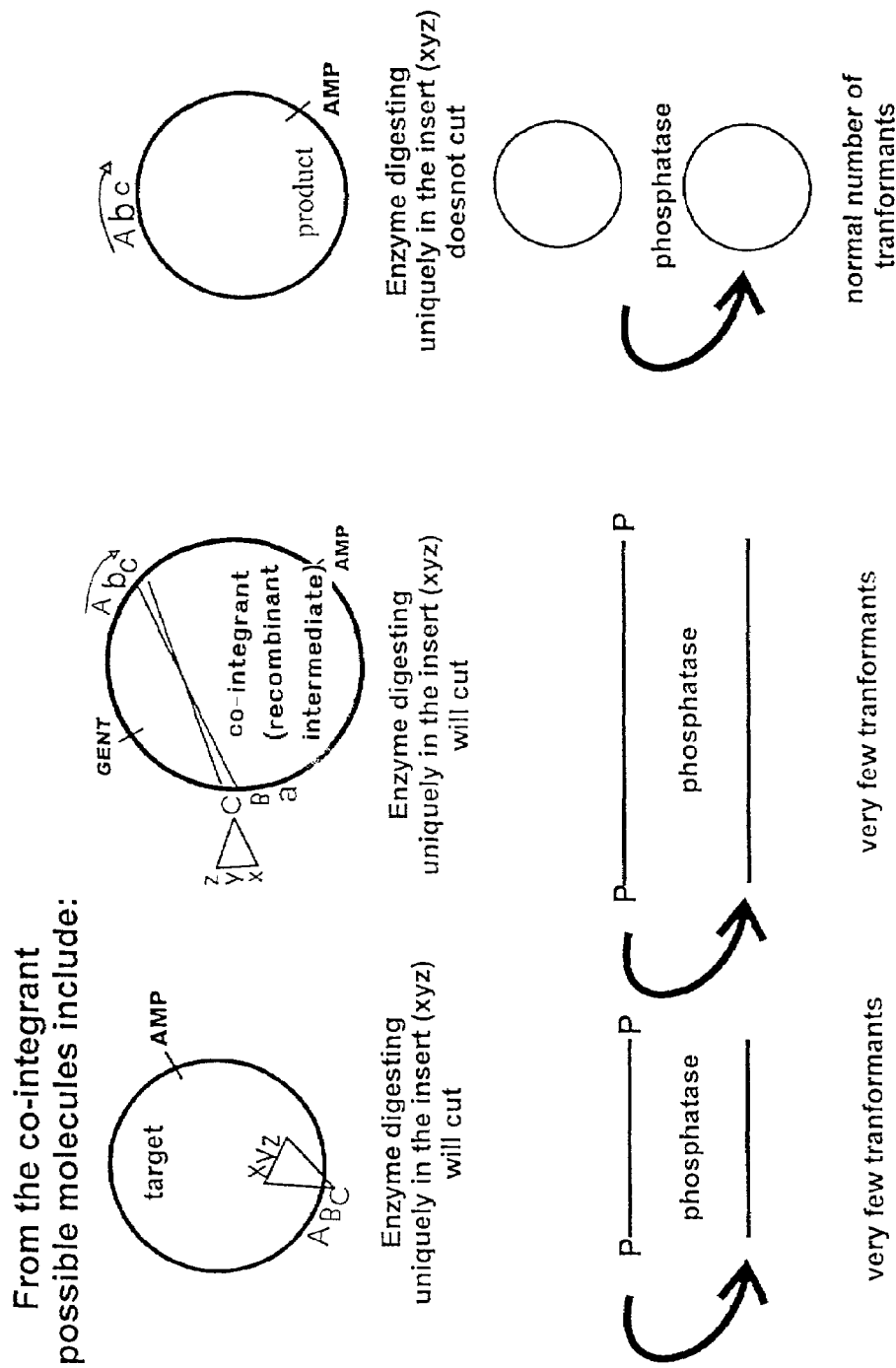

FIG. 21. Diagram showing principles of restriction nuclease-based selection against unrecombined target and donor vectors. Such methods are described in Section 5.1.2.1.1.

Figure 22:
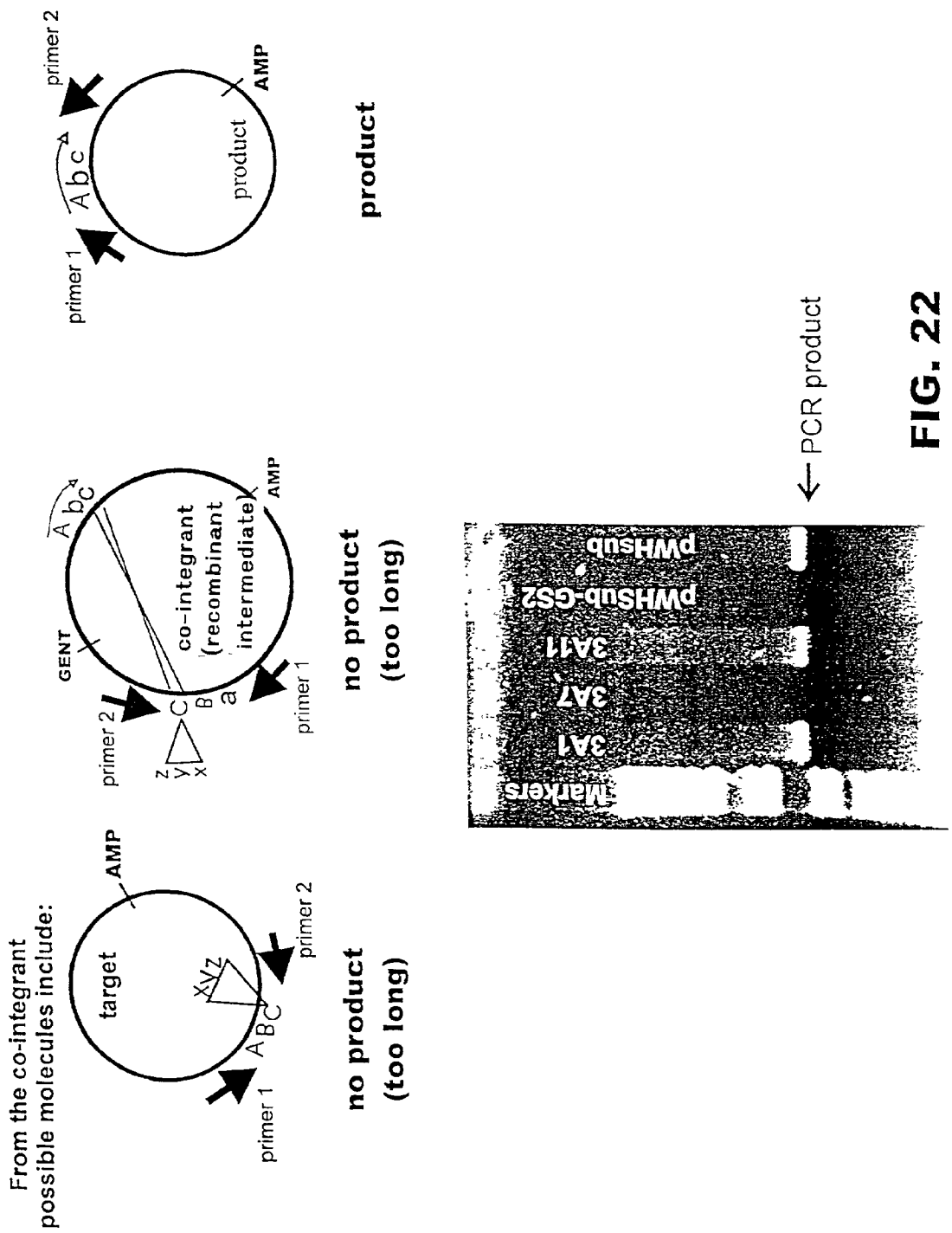

FIG. 22. Diagram showing principles of PCR size-based molecular selection against unrecombined target and donor vectors. Such methods are described in Section 5.1.2.1.1.

Figure 23:
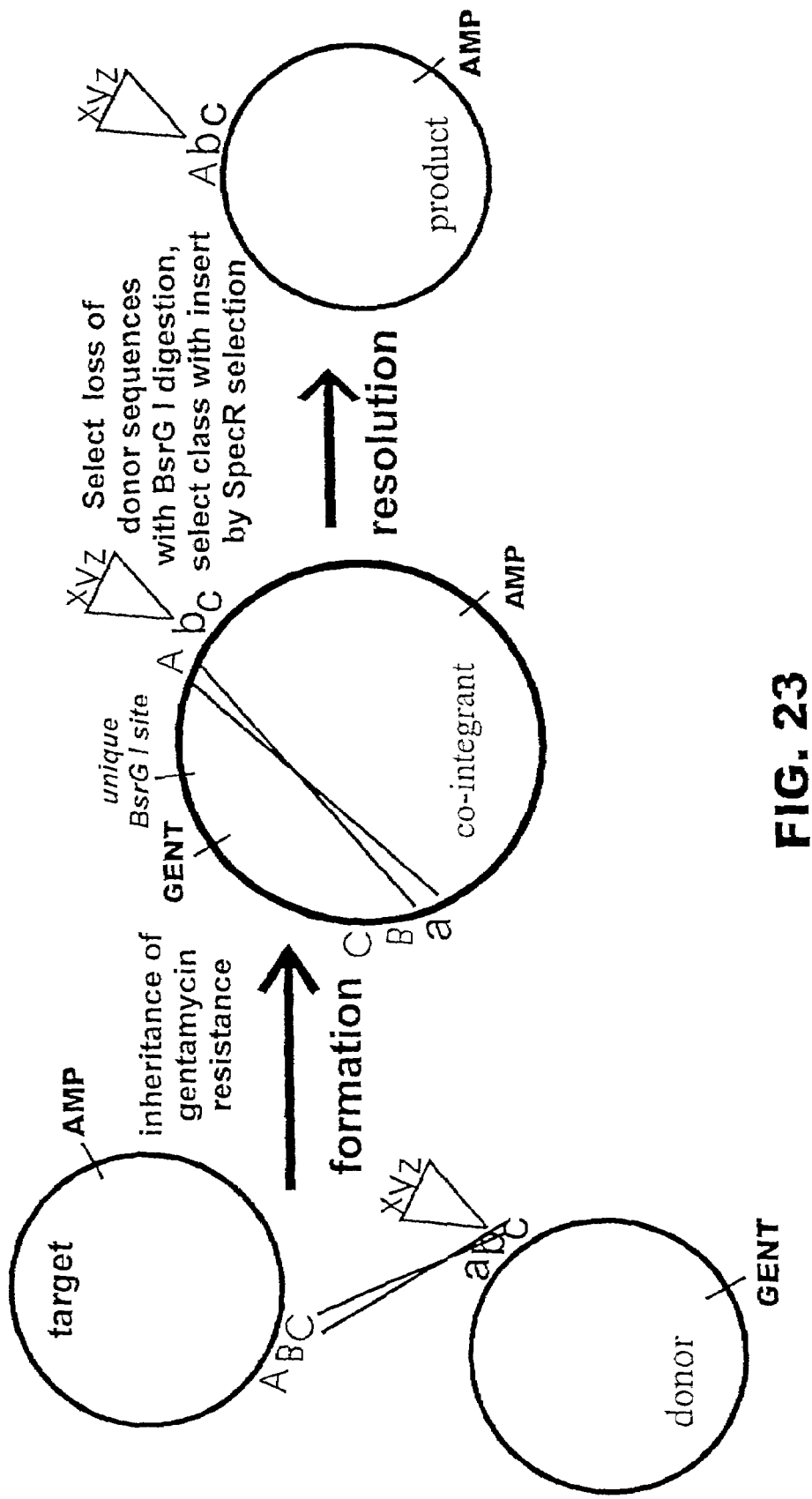

FIG. 23. Schematic and data describing use of DGA to place inserts unto target vector. FIG. 23 show how DGA (with the molecular restriction nuclease-based selection) can be used to insert donor sequences into a stretch of homologous target DNA, as described in Section 6.5.3.

FIG. 24A–24B. Table of oligonucleotides used in this study.

5. DETAILED DESCRIPTION OF THE INVENTION

Described herein are methods and compositions for directed gene assembly ("DGA"). The DGA system can iteratively be utilized until an optimized sequence for a desired trait has "evolved". First, a target sequence of interest is subjected to a systematic process that results in variation within the target. Variation is preferably generated by conjugative transfer of donor sequences into the target cell followed by homologous recombination between a donor sequence and the target sequence, as discussed in detail herein. The present invention also encompasses the use of methods other than conjugation to transfer the donor vector into the target cell, including but not limited to transformation or phage-mediated transfer. Second, the resulting sequence variants can be subjected to a selection process in which the sequences are selected or screened for exhibition of a desired trait. One or more iterations of the DGA process can be utilized to further optimize a desired trait. The starting material for each subsequent iteration is based on information obtained via analysis of variants obtained in the prior iteration(s). For example, sequence information obtained can indicate what domain or domains of the target sequence should be targeted for further sequence variation. Thus, rather than producing purely random sequence variants from a variant obtained in one round of DGA, the present method involves iterative DGA to systematically generate truly directed variants. Such DGA cycles can be reiterated as many times as necessary until sufficient optimization of the sequence of interest for the desired trait is attained.

The methods for DGA described herein utilize classical molecular and genetic techniques. In a preferred embodiment, DGA exploits the techniques of bacterial conjugation and homologous recombination. The DGA system is based on a collection of donor vectors and target vectors, and donor vector and target vector libraries. The target vectors are constructed and transformed into host strains, thereby creating target cellular, e.g., bacterial cell, populations. The donor vectors can, for example, be in the form of transformable plasmids or phage genomes. In a more preferred embodiment, donor vectors are constructed and transformed into host strains, thereby creating donor cellular populations. In one embodiment, donor and target cell populations are bacterial cell populations. In another embodiment, the donor and target cell populations are bacterial cell populations that are designed to be capable of bacterial conjugation with each other, such that, upon mixing of the donor and target cell populations, bacterial conjugation allows delivery of donor vector sequences from the donor cell to the target cell. Once the donor vector sequences that include the donor recombination module are in a target cell which expresses homologous recombination activity, homologous recombination results in rearrangement of target DNA sequences, due to regions of sequence homology between the donor and target gene sequences.

As used herein, two sequences are "homologous" if they share a region of sequence identity, optionally interrupted by one or more mismatched base pairs, such that they are capable of homologous recombinational exchange with each other. In a preferred embodiment, two homologous double-stranded sequences are completely identical. In another embodiment, the extent of homology is interrupted by not more than 1 mismatched base pair every approximately 10 base pairs of identical nucleotides. In a preferred embodiment, the extent of homology is a continuous stretch of at least 30, 40, 50, 60, 70, 80 90 or 100 base pairs of identical nucleotides. In various embodiments, the extent of homology between homologous sequences is a continuous stretch of at least 6, 8, 10, 15, 20, 25, 30, 35, 40, 50, 60, 75 or 100 base pairs of identical nucleotides. In an alternative embodiment, a stretch of identical nucleotides can be interrupted by 1, 2, 3, 4, 5, 6, 7, 8, 9 or 10 non-identical nucleotides per 100 identical nucleotides. In yet other embodiments, the extent of sequence identity between donor sequences and target sequences (i.e., each pair of first and second sequences) is at least 70%, more preferably at least 75%, more preferably at least 80%, more preferably at least 85%, yet most preferably at least 90% or 95% identity. In certain specific embodiments, the extent of sequence identity between donor and target sequences is at least 92%, 94%, 96%, 98% or 99%. Homologous sequences may be interrupted by one or more non-identical residues, provided they are still efficient substrates for homologous recombination.

The use of homologous recombination to promote rearrangements, particularly when coupled with bacterial conjugation, allows successive iterations of "evolution cycles" without requiring new rounds of in vitro molecular biological manipulations. Thus, this system provides faster and more cost effective methods, as compared to other methods for directed evolution, such as gene shuffling approaches.

Described below, are compositions and methods relating to DGA systems. In particular, Section 5.1 describes compositions suitable for practicing DGA, including donor vectors and libraries, target vectors and libraries, and cells carrying such vectors. Section 5.2, below, describes the DGA methods, including methods for the generation and selection of sequence variants, methods for optimization of a desired trait, and methods for reiteration of the DGA process. Finally, Sections 5.3, 5.4 and 5.5, below, describe archived collections of libraries and databases.

5.1 Compositions Suitable for Use in Directed Gene Assembly

In this section, compositions suitable for practicing DGA, including donor vectors and libraries, target vectors and libraries, and cells carrying such vectors are described in detail.

5.1.1 The Donor Vector

The invention encompasses donor vectors and donor vector libraries. A summary of the basic characteristics of the donor vector is presented in FIG. 1. Briefly, the donor vector comprises a donor recombination module, optionally a conjugative transfer element, and standard sequences required for maintenance and propagation of the donor vector in the cell, such as an origin of replication and a selectable marker. The donor vector can optionally further comprise a multiple cloning site and/or an additional selectable marker, in particular a positively selectable marker.

Preferably, the donor vector contains only a minimum amount of vector sequence homologous to other standard vectors, if any at all. Such a feature limits the amount of unwanted homologous recombination between donor and target vectors. Nonetheless, appropriate selection schemes can readily be devised to select against such rare, extra-recombination module recombination events. It is noted that the homology referred to herein refers to homology outside the donor and target recombination modules, and, in appropriate embodiments, outside the first and second non-functional selectable marker fragments.

The features of the donor vector are described in detail hereinbelow. The DNA vectors described herein may be constructed using standard methods known in the art (see Sambrook et al., 1989, Molecular Cloning, A Laboratory Manual, 2d Ed., Cold Spring Harbor Laboratory Press, Cold Spring Harbor, N.Y.; Ausubel, et al., 1989–1999, Current Protocols in Molecular Biology, Green Publishing Associates and Wiley Interscience, N.Y., both of which are incorporated herein by reference in their entirety). For example, synthetic or recombinant DNA technology may be used. Oligonucleotides may be synthesized using any method known in the art (e.g., standard phosphoramidite chemistry on an Applied Biosystems 392/394 DNA synthesizer). Further, reagents for synthesis may be obtained from any one of many commercial suppliers. Finally, it is noted that a donor vector can be constructed or derived from what is referred to herein as a "pre-donor" vector or plasmid molecule. Such a pre-donor molecule comprises the donor vector features described herein, including a multiple cloning site, but lacks a complete donor recombination module. In one embodiment, the pre-donor molecule contains a first and second donor DNA sequence within the multiple cloning site, but lacks a selectable marker between the two donor DNA sequences. Subsections of Section 6.1, below, describe the construction of pre-donor molecules.

5.1.1.1 The Donor Recombination Module

The donor vector contains at least two regions of sequence homology to a target vector: a first donor DNA sequence which is homologous to a first target DNA sequence; and a second donor DNA sequence which is homologous to a second target DNA sequence, so that homologous recombination can occur between donor and target vectors in a cell which capable of supporting homologous recombination (see e.g., Doherty et al., 1983, J. Mol.

Biol. 167: 539–60; and Laban and Cohen, 1981, Mol. Gen. 184: 200–7 for general discussion of homologous recombination). These regions of sequence homology reside within "recombination modules" on the respective vectors, with a donor recombination module on the donor vector, and a target recombination module on the target vector.

The donor recombination module comprises, in the following order from 5' to 3': a first donor DNA sequence; optionally, a third donor DNA sequence; and a second donor DNA sequence. The first and second donor DNA sequences are homologous to sequences in the target DNA and are designed so that homologous recombination between these sequences and the target DNA sequences will occur and result in sequence exchange. Upon homologous recombination between homologous sequences of the donor and target vectors, sequences residing between the regions of homology are exchanged, creating a new product comprising a sequence variant of the target sequence. This product comprises a variant product module.

The optional third donor sequence is not homologous to sequences in the target DNA and is preferably a negatively selectable sequence (see Section 5.1.2.1.1, infra), which can be present either alone or in conjunction with a positively selectable marker (preferably different from the positively selectable marker or markers present elsewhere on the donor vector), for example, present as part of a selectable marker cassette. Such cassettes include, but are not limited to, Gal-Spec and Kan-Suc cassettes, as described in Section 6, below.

Homologous recombination in the target cell results in strand exchange between donor and target DNA sequences. To the extent that target DNA sequences are part of or correspond to target gene sequences, in general, it is preferred that the donor vector comprises donor DNA sequences homologous to a portion of the target gene smaller than the entire target gene. Such a situation represents another way the extent of the region exchanged in the recombination process can be directed to a particular region of the target gene. To avoid recombination events outside the target gene in the target vector, the donor vector is preferably designed so that the only target gene homology lies within the recombination module. Thus, the donor vector should generally not share sequence homology of 10 or more contiguous base pairs with the target vector outside the target recombination module.

DNA sequences for use with these vectors and methods may come any source, including, but not limited to, prokaryotic, archaebacterial or eukaryotic DNA sequences, or from viral, phage or synthetic origins. For example, nucleic acid sequences may be obtained from the following sources: human, porcine, bovine, feline, avian, equine, canine, insect (e.g., *Drosophila*), invertebrate (e.g., *C. elegans*), plant, microbial (e.g., thermophilic bacteria) etc. In one embodiment, the DNA donor sequences are derived from characterized cloned DNA sequences and libraries of sequences. In another embodiment, the source DNA is produced synthetically, for example, by synthesizing oligonucleotides. Stretches of random oligonucleotides can be embedded into the homologies used to direct recombination in the DGA strategy of the present invention. The random nucleotides can be present as continuous stretches or be interspersed with regions of fixed homologies; so long as homolgous recombination between the target and donor sequences can still occur. The use of random synthetic sequences within the context of the DGA approach to directed evolution has broad application to all the potential applications of directed evolution, extending well beyond those of typical random peptide libraries which most typically address specific binding interactions (see, e.g., Brown, 2000, Curr. Opin. Chem. Bio. 14: 16–21). In another embodiment, sequences are generated by mutagenesis, and cloned into donor vectors that can be used in DGA.

Such DNA sequences may be obtained and used to construct donor vectors suitable for use in the DGA system, as described above, by standard procedures known in the art, such as, for example, standard molecular biology techniques, such as PCR and molecular cloning, etc. (see, e.g., Sambrook et al., 1989, supra; Ausubel, et al., supra; Glover (ed.), 1985, DNA Cloning: A Practical Approach, M. L. Press, Ltd., Oxford, U.K. Vol. I, II). Libraries of donor vectors may be archived, for multiple use with different target vectors (see Sections 5.3 and 5.4 hereinbelow).

5.1.1.2 Conjugative Transfer Sequences

In embodiments where the donor vector is transferred to target cells by means of conjugative transfer, the donor vector comprises sequences that direct the conjugative transfer of donor DNA sequences from the donor cell to the target cell using the process of bacterial conjugation process. During conjugation, a physical bridge is formed between two bacterial cells which allows the exchange of plasmid DNA (see, e.g., Wallets and Wilkins, 1984, Microbiol. Rev. 48: 24–41).

Systems for bacterial conjugation, and the genes and sequences required therefor, are known in both gram-negative bacteria, including *E. coli* (see Nunez et al., 1997, Mol. Microbiol. 24: 1157–68; Wallets and Skurray, 1987, Cellular and Mol. Biol. (Ed. F. C. Neidhardt) pp. 1110–1133); Wallets and Skurray, 1982, Ann. Rev. Genet. 14:41–76) and gram-positive bacteria (Firth et al., 1999, Mol. Microbiol. 31:1598–600). Such sequences can be inserted into donor vector, which can confer conjugative transferability to donor plasmid. In one embodiment, conjugative transfer functions are provided in trans from gene sequences present on the bacterial chromosome, thereby preventing transfer of the donor vector in the target cell (Metcalf et al. 1994, Gene 138:1–7). Donor cells designed in this way also produce more copies of the vector on which the conjugative transfer sequence resides. In a preferred embodiment, sequences from the conjugative plasmid R6K is used (for review see Filutowicz and Rakowski, 1998, Gene 223:195–204). The donor vector contains a minimal cis-acting R6K sequence, while trans-acting conjugation genes required for recognition, transfer, and structural functions are provided by sequences on the chromosome of the target cell. Minimal lambda phages designed for convenient cloning are well known to those trained in the art of molecular biology (see Miller 1992, supra). Derivatives with conditional lethal mutations that require propagation in an amber suppressor host provide a convenient gene delivery system as infection of such phage into a bacterium without an amber suppressor produces in no infection and simply results in the delivery of DNA to a host strain, i.e., a target cell.

5.1.1.3 Origin of Replication

The donor vector requires an origin of replication, which is needed for propagation of the vector. In this respect, donor vectors must be designed to be compatible with other plasmids in the donor cell, as well as target cell vectors.

For cloning and propagation in *E. coli*, any *E. coli* origin of replication may be used, examples of which are well-known in the art (see Miller, 1992, A Short Course in Bacterial Genetics, Cold Spring Harbor Laboratory Press, NY, and references therein). Non-limiting examples of readily available plasmid origins of replication are ColE1-derived origins of replication (Bolivar et al., 1977, Gene 2:95–113; see Sambrook et al., 1989, supra), p15A origins present on plasmids such as pACYC184 (Chang and Cohen, 1978, J. Bacteriol. 134:1141–56; see also Miller, 1992, supra, p.10.4–10.11), and pSC101 origin are all well known in the art.

For example, in one embodiment, a high-copy replicating plasmid is used, such as a plasmid containing a ColE1-derived origin of replication, examples of which are well known in the art. One example is an origin from pUC19 and its derivatives (Yanisch-Perron et al., 1985, Gene 33:103–119), which have convenient cloning sites for insertion of foreign genes. An example of a medium-copy plasmid with a ColE1-derived origin of replication is pBR322 (Bolivar et al., 1977, Gene 2:95–113; see Sambrook et al., 1989, supra).

In one embodiment, a donor plasmid having a p15A origin of replication is used, to be compatible with a target plasmid having a ColE1-derived origin of replication. One example of a plasmid having a p 15 origin of replication is pACYC184, one of the pACYC100 series of plasmids, which exist at 10–12 copies per cell (Chang and Cohen, 1978, J. Bacteriol. 134:1141–56; see also Miller, 1992, p. 10.4–10.11). In another embodiment, another ColE1 compatible plasmid, pSC101 origin, such as pSC101, which exists at approximately 5 copies per cell, may be used. Both pACYC and pSC101 plasmid vectors have convenient cloning sites and can co-exist in the same cell as pBR and pUC plasmids.

Other suitable plasmid origins of replication include lambda or phage P1 replicon-based plasmids, for example the Lorist series (Gibson et al., 1987, Gene 53: 283–286). In another embodiment, synthetic origins of replication may be used. In another embodiment, non-plasmid vectors may also be used. For example, λ vectors, such as λgt11 (Huynh et al., 1984, in "DNA Cloning Techniques: A Practical Approach," Vol I, D. Glover, ed., pp 49–78, IRL Press, Oxford), or the T7 or SP6 phage systems (Studier et al., 1990, Methods Enzymol. 185:60–89) can be used. Such viral systems would not require conjugation for delivery of DNA sequences.

In yet another embodiment, the origin of replication of a donor vector and/or a target vector is compatible with replication in a Salmonella species, most preferably *Salmonella typhimurium*. For examples of origins of replications compatible with Salmonella, see, e.g., Miller, J. H., 1992, A Short Course in Bacterial Genetics, Cold Spring Harbor Laboratory Press, NY; Neidhardt, F. C., ed., 1987, *Escherichia coli* and *Salmonella typhimurium*, American Society for Microbiology, Washington, D.C.

The positively selectable sequence can be present at any position of the donor DNA vector as long as it does not interfere with vector functions (for example replication in donor cells, conjugative transfer, if utilized, other selectable markers present on the vector). Among the cells that can be utilized in conjunction with the vectors and methods described herein are naturally transformable bacterial cell such as *Acinetobacter calcoaceticus* (ATCC No. 33305). An exemplary origin of replication that can be utilized in vectors intended to be present in *A. calcoaceticus* is the origin of replication preset in the cryptic plasmid pWH1277 described in Hunger et al., 1990, Gene 87:45–51.

In a preferred embodiment, the origin is a conditional origin of replication, that is, is one that is dependent on transacting replication functions that are not present in the target cell. For a discussion of such a transacting factor see Kruger et al., 2001, J Mol. Biol. 306:945–55. Constructed in this way, the donor vector cannot replicate in the target cell, thereby facilitating its loss after it is transferred into the target cell.

5.1.1.4 Selectable Markers

To maintain the donor vector in the cell, the vector typically contains a selectable marker. Any selectable marker known in the art can be used. Donor vectors must be compatible with vectors of the target cell, which requires the choice of a selectable marker different than, and compatible with any selectable markers expressed in the target cell. Any gene that conveys a readily identifiable or selectable phenotypic change, such as resistance to an antibiotic effective in *E. coli*, can be used. Preferably, the selectable marker is an antibiotic resistance gene, such as the kanamycin resistance gene from TN903 (Friedrich and Soriano, 1991, Genes. Dev. 5:1513–1523), or genes that confer resistance to other aminoglycosides (including but not limited to dihydrostreptomycin, gentamycin, neomycin, paromycin and streptomycin), the β-lactamase gene from IS1, that confers resistance to penicillins (including but not limited to ampicillin, carbenicillin, methicillin, penicillin N, penicillin O and penicillin V). Other selectable genes sequences including, but not limited to gene sequences encoding polypeptides which confer zeocin resistance (Hegedus et al. 1998, Gene 207:241–249). Other antibiotics that can be utilized are genes that confer resistance to amphenicols, such as chloramphenicol, for example, the coding sequence for chloramphenicol acetyltransferase (CAT) can be utilized (Eikmanns et al. 1991, Gene 102:93–98). As will be appreciated by one skilled in the art, other non-antibiotic methods to select for maintenance of the plasmid may also be used, such as, for example a variety of auxotrophic markers (see Sambrook et al., 1989, supra; Ausubel et al., supra), which can be selected by adding or subtracting a particular nutrient from the growth media.

5.1.2 The Target Vector

In addition to the donor vector, the invention also encompasses target vectors and target vector libraries. A summary of the basic characteristics of the target vector is presented in FIG. 2. Briefly, the target vector comprises a target recombination module, preferably, sequences that allow transcription of sequences within the first and/or second target DNA sequences of the target recombination module, and standard sequences required for maintenance and propagation of the vector in the cell, e.g., an origin of replication and a selectable marker.

Preferably, the target vector contains only a minimum amount of vector sequence homologous to other standard vectors, if any at all. Such a feature limits the amount of unwanted homologous recombination between donor and target vectors. Nonetheless, appropriate selection schemes can readily be devised to select against such rare, extra-recombination module recombination events. It is noted that the homology referred to herein refers to homology outside the donor and target recombination modules, and, in appropriate embodiments, outside the first and second non-functional selectable marker fragments.

In a specific embodiment, a target vector comprises a target recombination module, one or more origins of replication, and one or more selectable markers (e.g., an antibiotic resistance gene). The target recombination module is designed to enable selection for recombinant variant target vectors, and to provide a mechanism for selection against non-recombinant vectors, both donor and targets. To this end, as described in detail below, a recombinant selection system is built into sequences within or immediately flanking the target recombination module.

In a variation of this method, the target vector is present in the target cell integrated into the target cell genome. In such an embodiment, the vector need not contain sequences required for maintenance and propagation of the vector and, therefore, comprises a target recombination module. Preferably, the target recombination module is integrated in a manner that readily allows excision or isolation of the module out genome, i.e., via flanking unique restriction sites or by specific amplification of the module.

Finally, it is noted that a target vector can be constructed or derived from what is referred to herein as a "pre-target" vector or plasmid molecule. Such a pre-target molecule comprises the target vector features described herein, including a multiple cloning site, but lacks a complete target recombination module. In one embodiment, the pre-target molecule contains a first and second target DNA sequence within the multiple cloning site, but lacks a selectable marker between the two target DNA sequences. Section 6.2.1, below, describe the construction of pre-target molecules.

5.1.2.1 The Target Recombination Module

The target vector comprises a target recombination module comprises, in the following order from 5' to 3': a first target DNA sequence and a second target DNA sequence. The target recombination module further comprises additional sequences to select products of recombination. As discussed in detail below, such sequences can allow selection against non-recombined target vectors using negatively selectable markers, and/or for recombined target molecules using positively selectable markers.

Target sequences from which the variant sequences are generated by the methods of the invention can include any DNA sequence of interest. For example, a target sequence can encode a polypeptide of interest, or a fragment thereof (e.g., a structural or biological domain of the polypeptide of interest). Among the nucleic acid sequences that can be varied according to the methods of the present invention are ones that encode polypeptides that include, but are not limited to polypeptides, or portions thereof, involved in cell proliferation, development, differentiation, signal transduction, enzymatic reactions, either in vivo or in vitro. Alternatively, for example, a target sequence can be a regulatory sequence e.g., a sequence that controls, positively or negatively, the temporal and/or spatial, cell or tissue-specific expression, of a coding region to which the regulatory sequence is operably attached. In another embodiment, a target sequence encodes a nucleic acid, e.g., an antisense or ribozyme molecule, that can modulate the expression of a gene or transcript in trans.

5.1.2.1.1 Negatively Selectable Markers

In one embodiment, the target vector comprises a target recombination module comprising, in the following order from 5' to 3': a first target DNA sequence; a negatively selectable marker, and a second target DNA sequence. The first and second target DNA sequences are respectively homologous to sequences in the first and second donor DNA sequences, described in Section 5.1.1.1, above, designed so that homologous recombination between donor and target sequences results in sequence exchange.

The negatively selectable marker is included in the target recombination module to facilitate selection for target recombination modules that have successfully undergone homologous recombination. In principle, any negative selection system that allows selection against non-recombined target vector can be used for DGA. Examples of such negatively selectable markers are provided hereinbelow.

In one embodiment, the negatively selectable marker is a sequence that encodes a conditional lethal gene product, whose expression is detrimental to cell growth under a particular set of conditions. Recombination results in the exchange of the negatively selectable marker. Under selective conditions, the lethal function is expressed, and only the recombined products with variant recombination modules will survive. This selection for recombinant products does not depend on the precise nature of the specific recombinant products (FIG. 3). A large number of conditionally lethal sequences are known which can be used in these assays, including, but not limited to, sucrose sensitivity (Lawes and Maloy, 1995, J. Bacteriol. 177:1383–7), and galactose sensitivity (Ahmed, 1984, Gene 28:37–43). Selection against the conditionally lethal marker will enrich for the subpopulation of recombinants which can be tested for the desired phenotype.

In another embodiment, the negatively selectable marker is a polar sequence (see FIG. 4). Certain sequences, such as sequences found within the transposon Tn5 or Tn10 have the capacity to block the progress of RNA polymerase along a DNA template, resulting termination of transcription. Thus, the presence of these so-called polar sequences can block the expression of downstream genes (Merrick et al., 1978, Mol. Gen. Genet. 165: 103–11).

For the purposes of a negatively selectable marker comprising a polar sequence, it is necessary to construct a target vector comprising: a promoter sequence on the 5' side of the first target DNA sequence, a polar sequence placed in the target recombination module 3' to the first target DNA sequence, and 5' to the second target DNA sequence, and a reporter gene placed downstream from the 3' side of the second target DNA sequence, such that expression of the reporter gene is dependent upon transcription initiated at the promoter sequence and continuing through the recombination module. Thus, the presence of the polar sequence within the module blocks transcription unless homologous recombination between donor and target sequence results in the removal of the polar sequence and expression of the reporter gene. Selection for the expression of the downstream reporter gene requires the removal of the polar insert.

For the purposes of this selection scheme a "reporter gene" sequence can comprise any gene sequence which expresses or encodes a detectable or positively selectable gene product (preferably a protein). In a preferred embodiment, the activity or presence of such a gene product allows cell growth under selective conditions. A variety of such reporter gene sequences well known to those of skill in the art can be utilized. For example, β-lactamase, which confers resistance to the penicillin family of antibiotics can be used, or sequences which confer resistance to other antibiotics, such as tetracycline, streptomycin, gentamycin, neomycin, kanamycin, hygromycin, or chloramphenicol. Non-antibiotic methods, such as, for example, auxotrophic markers (see Sambrook et al., 1989, supra; Ausubel et al., supra) may also be used as reporter genes, as will be appreciated by one skilled in the art, other which can be selected on particular growth conditions. Detectable markers suitable as reporter genes include but are not limited to β-galactosidase and green fluorescent protein.

In other embodiments, the negatively selectable marker is any nucleic acid having a sequence that confers certain physical properties that can be the subject of selection. For example, in one embodiment, the negatively selectable marker is a nucleic acid sequence comprising a restriction enzyme recognition site that is unique to the target vector and thus absent from the variant target produced by homologous recombination. The digestion of a mixture of molecules containing the resolved recombinant structure with the enzyme will convert the target vector, but the not the desired recombinant target variant, from a circular to a linear molecule. Circular molecules are more effective at transforming cells than linear molecules, and this difference can be dramatically enhanced by subsequent phosphatase or exonuclease treatment. In this way a property of the insert (as revealed by nuclease treatment) can provide a molecular selection for the recovery of the desired recombinant class.

In another selection method based on the physical properties of a sequence inserted into the target module, the general property of DNA length (without regard to sequence particulars) can also provide a mechanism to select recombinant molecules using PCR. By limiting the extension time of a PCR reaction driven by primers outside the target gene, PCR reaction extension time can be used to size-select the amplification of a desired product class. A thermostable polymerase will proceed at a rate of about 17 bases per second requiring about 90 seconds to complete a 1.5KB segment. Thus, for example, if such a segment had an insert of an additional 4KB, PCR could not amplify the 5.5 KB target with a 90 second extension time. If both the 1.5 KB (target) and 5.5 KB (target plus insert) were subjected to the PCR amplification procedure (together) with the same outside primers, only the 1.5 KB piece would be amplified. Such a PCR strategy can be used to recover a true recombinant (without an insert) from a background of material with an insert. In an alternative mode of the embodiment, size selection of the PCR product can be achieved by agarose gel electrophoresis rather than by limiting the extension time for a PCR reaction. In this mode of the embodiment, the sequence inserted into or deleted from the target module can be of any size, with the constraint that the size difference between the PCR products of the unrecombined target module and the recombinant variant target module should be detectable.

The negatively selectable marker can be present in the target vector either alone or in conjunction with a positively selectable marker (preferably different from the positively selectable marker or markers present on the donor vector), for example, present as part of a selectable marker cassette. Such cassettes include, but are not limited to, Gal-Spec and Kan-Suc cassettes, as described in Section 6, below.

5.1.2.1.2 Positively Selectable Markers

In another embodiment, recombinants may be selected by reconstruction of a flanking positively selectable marker. In this embodiment, the donor and target vectors are designed so that homologous recombination between regions of homology on the donor and target vectors result in the reconstruction of a sequence which encodes a selectable marker which was absent in both donor and target vectors. Thus, selection for the newly reconstructed selectable marker allows for selection of a recombination event that also results in the creating of a variant target gene sequence.

For example, in one embodiment of this method, outlined in FIG. 5, the target vector comprises a target recombination module comprising, in the following order from 5' to 3': a sequence wxy, a non-functional fragment of a sequence wxyz, which in turn encodes a functional gene product; a first target DNA sequence (AB in FIG. 5); and a second target DNA sequence (c) in FIG. 5). The donor recombination module comprises, in the following order from 5' to 3': a sequence xyz, which is a second non-functional fragment of the sequence wxyz; a first donor sequence (ab in FIG. 5); and a second donor sequence ("c") in FIG. 5). The first and second target DNA sequences are homologous to a sequences in the first and second donor DNA sequences, as described in Section 5.1.1.1, above. Recombination between donor and target sequences results in reconstruction of the sequence wxyz, which is able to encode a functional selectable marker. Thus, selection for the newly reconstructed selectable marker allows for selection of a recombination event, and selection against cells which lack recombinant vectors. Other variations of this method include embodiments wherein the incomplete sequences are located immediately 3' to the second donor sequence and second target DNA sequences.

Further, any gene that conveys a readily identifiable or selectable phenotypic change, such as resistance to an antibiotic effective in *E. coli*, can be used as a selectable marker. Preferably, the selectable marker is an antibiotic resistance gene, such as the kanamycin resistance gene from TN903 (Friedrich and Soriano, 1991, Genes. Dev. 5:1513–1523), or genes that confer resistance to other aminoglycosides (including but not limited to dihydrostreptomycin, gentamycin, neomycin, paromycin and streptomycin), the β-lactamase gene from IS1, that confers resistance to penicillins (including but not limited to ampicillin, carbenicillin, methicillin, penicillin N, penicillin O and penicillin V). Other selectable genes sequences include, but are not limited to gene sequences encoding polypeptides which confer zeocin resistance (Hegedus et al. 1998, Gene 207:241–249). Other antibiotics that can be utilized are genes that confer resistance to amphenicols, such as chloramphenicol, for example, the coding sequence for chloramphenicol transacetylase (CAT) can be utilized (Eikmanns et al. 1991, Gene 102:93–98). As will be appreciated by one skilled in the art, other non-antibiotic methods to select for maintenance of the plasmid may also be used, such as, for example a variety of auxotrophic markers (see Sambrook et al., 1989, supra; Ausubel et al., supra), which can be selected by adding or subtracting a particular nutrient from the growth media.

5.1.2.2 Additional Target Vector Sequences

As described above for the donor vector, the target vector is compatible with all vectors present in the donor cell with respect to replication origin and the selectable marker and/or reporter genes, and is compatible with any other vectors residing in the target cell. Such requirements are described in Sections 5.1.1.3 and 5.1.1.4, above. As discussed in those sections, the chosen vector must be compatible with the donor vector plasmid described in Section 5.1, above. One of skill in the art will readily be aware of the compatibility requirements necessary for maintaining multiple plasmids in a single cell. Methods for propagation of two or more constructs in procaryotic cells are well known to those of skill in the art. For example, cells containing multiple replicons can routinely be selected for and maintained by utilizing vectors comprising appropriately compatible origins of replication and independent selection systems (see Miller et al, 1992, supra; Sambrook et al., 1989, supra).

Optionally, the target vector has additional features necessary for the screening or selection of the desired phenotypic characteristic of the recombined target gene, which is referred to herein as the "variant target gene", and which contains a "variant sequence module". In certain embodiments, for example, where screening or selection of the desired phenotypic characteristic of the variant target gene is performed within the target cell itself, or where variant target gene products are purified from the target cell, signals for expression of the variant target gene, and/or a reporter gene construct may be included in the target vector. In an alternative embodiment, the variant target gene is transferred to a secondary host for screening or selection of the desired phenotype. In this embodiment, the target vector may contain sequences that allow transfer, maintanence or propagation of the vector in the secondary host cell (e.g., mammalian tissue culture cells). For example, the target vector may include specialized origins of replication and expression systems, that allow expression of the variant genes in a secondary host. In one embodiment, for example, the target vector further comprises an SV40 origin of replication. FIG. 2 summaries these features.

In one embodiment, the target vector may contain sequences for regulating expression of the target DNA sequence, target gene, or variant target gene. With respect to regulatory controls which allow expression, either regulated or constitutive, at a range of different expression levels, a variety of such regulatory sequences are well known to those of skill in the art. The ability to generate a wide range of expression is advantageous for utilizing the methods of the invention, as described below. Such expression can be achieved in a constitutive as well as in a regulated, or inducible, fashion.

Inducible expression yielding a wide range of expression can be obtained by utilizing a variety of inducible regulatory sequences. In one embodiment, for example, the lacI gene and its gratuitous inducer IPTG can be utilized to yield inducible, high levels of expression of the target gene sequences, e.g., a reassembled target gene sequence, when the sequences are transcribed via the lacOP regulatory sequences.

Preferably, the expression of a variant target gene is controlled by an inducible promoter. Inducible expression yielding a wide range of expression can be obtained by utilizing a variety of inducible regulatory sequences. In one embodiment, for example, the lacI gene and its gratuitous inducer IPTG can be utilized to yield inducible, high levels of expression of a target sequence, e.g., a reassembled target gene, when sequences encoding such polypeptides are transcribed via the lacOP regulatory sequences. A variety of other inducible promoter systems are well known to those of skill in the art which can also be utilized. Levels of expression from reassembled target gene constructs can also be varied by using promoters of different strengths.

Other regulated expression systems that can be utilized include but are not limited to, the araC promoter which is inducible by arabinose (AraC), the TET system (Geissendorfer and Hillen, 1990, Appl. Microbiol. Biotechnol. 33:657–663), the $p_L$ promoter of phage λ temperature and the inducible lambda repressor $CI_{857}$ (Pirrotta, 1975, Nature 254: 114–117; Petrenko et al., 1989, Gene 78:85–91), the trp promoter and trp repressor system (Bennett et al., 1976, Proc. Natl. Acad. Sci USA 73:2351–55; Wame et al., 1986, Gene 46:103–112), the lacUV5 promoter (Gilbert and Maxam, 1973, Proc. Natl. Acad. Sci. USA 70:1559–63), lpp (Nokamura et al., et al., 1982, J. Mol. Appl. Gen. 1:289–299), the T7 gene-10 promoter, phoA (alkaline phosphatase), recA (Horii et al. 1980), and the tac promoter, a trp-lac fusion promoter, which is inducible by tryptophan (Amann et al., 1983, Gene 25:167–78), for example, are all commonly used strong promoters, resulting in an accumulated level of about 1 to 10% of total cellular protein for a protein whose level is controlled by each promoter. If a stronger promoter is desired, the tac promoter is approximately tenfold stronger than lacUV5, but will result in high baseline levels of expression, and should be used only when overexpression is required. If a weaker promoter is required in bacterial cells, other bacterial promoters are well known in the art, for example, maltose, galactose, or other desirable promoter (sequences of such promoters are available from Genbank (Burks et al. 1991, Nucl. Acids Res. 19:2227–2230).

In another embodiment, where it is desired to transfer the variant target gene into a secondary host for expression and screening assays, a target vector may also contain sequences for expression of the reassembled target gene in eukaryotic cells. Methods for the construction of such vector sequences may include in vitro recombinant DNA and synthetic techniques and in vivo recombinants (genetic recombination). Expression of nucleic acid sequence encoding a reassembled target protein or peptide fragment may be regulated by a second nucleic acid sequence so that the reassembled target protein or peptide is expressed in a host transformed with the recombinant DNA molecule. For example, expression of a reassembled target gene or gene product may be controlled by any promoter/enhancer element known in the art. Promoters which may be used to control reassembled target gene or gene product include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); plant expression vectors comprising the nopaline synthetase promoter region (Herrera-Estrella et al., 1984, Nature 303: 209–213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115–120); promoter elements from yeast or other fungi such as the Gal 4 promoter, the ADC (alcohol dehydrogenase) promoter, PGK (phosphoglyceroyl kinase) promoter, alkaline phosphatase promoter, and the following animal transcriptional control regions, which exhibit tissue specificity and have been utilized in transgenic animals: elastase I gene control region which is active in pancreatic acinar cells (Swift et al, 1984, Cell 38:639–646; Ornitz et al. 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318: 533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94; myelin basic protein gene control region which is active in oligodendrocyte cells in the brain (Readhead et al., 1987, Cell 48:703–712); myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

In another embodiment, the target vector comprises sequences for transfer of the recombined vector carrying the variant recombination module to a secondary host organism for expression, screening, and/or selection assays. For example, so-called shuttle vectors have been designed to allow replication in a host bacterium, such as *E. coli*, and also allow transfer and replication in a variety of organisms, such as other bacteria (e.g., Bruckner, 1992, Gene 122: 187–92); yeast (e.g., Brunelli and Pall, 1993, Yeast 9: 1309–18); plants (e.g. Stanley, 1993, Curr. Opin. Genet. Dev. 3: 91–6); and mammalian systems (e.g. Karreman, 1998, Nucleic Acids Res. 26: 2508–10), where the subsequent selections can be performed. To act as a shuttle vector, the target vector should be able to replicate in the bacterial host to take advantage of both rapid generation times and, optionally, the simple genetic conjugation-based exchange systems. The target vector can readily be modified to include features of shuttle vectors, which are well know to those of skill in the art (see, e.g., Pouwels, Cloning Vectors: a Laboratory Manual, Supplementary Update 1988, Elsevier; New York, N.Y. 1988).

In yet another embodiment, the target vector comprises restriction endonuclease recognition sites to facilitate molecular manipulation of the variant target module, for example so that the variant target can be cloned into a different vector.

5.1.3 Cells

Target host cells may be of any cell type which is capable of supporting homologous recombination. A cell capable of supporting homologous recombination contains a recombinase activity that catalyzes strand exchange between sequences with stretches of homology. In a preferred embodiment, the cells are bacterial cells and typically contain one or more bacterial recombinases. In embodiments where the donor vector is transferred to a bacterial target cell by conjugation of a bacterial donor cell with the bacterial target cell, donor and target host cells may be of any cell type which is capable of conjugative transfer of DNA. Such cells are well known to those of skill in the art. See, e.g., Ely, B., 1985, Mol. Gen. Genet. 200:302–304. In embodiments where the donor vector is transferred to a target cell by conjugation, the target host cell is preferably naturally transformable to circumvent the need for preparing competent cells for transformation. In embodiments where the donor vector is transferred to a target cell by infection with a phage comprising the donor vector, the target cell must be capable of supporting transfer of donor sequences by the phage of choice. In a preferred embodiment, the phage comprising the donor vector is not capable of a full cycle of infection in the target cell, e.g., cannot lyse a target cell into which a donor vector has been transferred.

Preferably, the target cell and, where utilized, the donor cell, are gram-negative bacterial cells, but gram-positive cells are also possible. More preferably, the host cell is an Enterobacterial cell. Members of the family Enterobacteriaceae include, but are not limited to, species of *Escherichia, Salmonella, Citrobacter, Klebsiellae*, and *Proteus*. Most preferably the host cell is an *Escherichia coli* cell. Naturally transformable bacteria for use with transformation-mediated transfer of the donor vector into the target cell include, for example, *Acinetobacter calcoaceticus, Haemophilus influenzae* and *Neisseria meningitidis* (Smith et al., 1999, Res. Microbiol. 150(9–10):603–16). In embodiments where donor cells are utilized, the donor and target cells should comprise sequences or genetic backgrounds that allow independent selection for or against the presence of either the donor or the target cell. For example, the growth requirements and/or antibiotic resistance characteristics of the target and donor cells can be designed such that the presence of target cells can be selected for and/or the presence of donor cells can be selected against. Alternatively, methods for segregation of donor sequences can be utilized such as those described, below, in Section 5.2.3.

Target cells can also be derived from any organism, including, but not limited to, yeast, insect, or mammalian cells, provided they express, or can be engineered to express, a homologous recombinase activity capable of mediating recombination between two DNA molecules containing at least one region of sequence homology. The recombinase is preferably a recombinase derived from *E. coli*. Such recombination-proficient cells may be made electrocompetent in advance and stored at −70° C.

5.1.4 Determining Sequence Identity between Donor and Target Modules

As discussed above, the donor and the target sequences are homologous to each other. The extent of homology between the first donor sequence and the first target sequence, or between the second donor sequence and the second target sequence, is preferably at least 70% sequence identity. In other embodiments, the extent of sequence identity preferably at least 75%, 80%, 85%, 90% or 95% identity. In certain specific embodiments, the extent of sequence identity between donor and target sequences is at least 92%, 94%, 96%, 98% or 99%. A percentage of sequence identity between donor and target sequences that is 95% or greater, most preferably at least 98%, is desirable when the one-step selection method is utilized for selection of recombinant modules. Homologous sequences may be interrupted by one or more non-identical residues, for example for addition of novel sequences that can add function to a protein as described in Section 5.2.3, supra, provided they are still efficient substrates for homologous recombination.

To determine the percent identity of two nucleic acid sequences, the sequences are aligned for optimal comparison purposes (e.g., gaps can be introduced in the sequence of the donor sequence for optimal alignment with the target nucleic acid sequence, particularly where one or both of the donor and target sequences are interrupted by extraneous sequences). The nucleotides at corresponding nucleotide positions are then compared. When a position in the donor sequence is occupied by the same nucleotide as the corresponding position in the target sequence, then the molecules are identical at that position. The percent identity between the two sequences is a function of the number of identical positions shared by the donor and target sequences (i.e., % identity=# of identical overlapping positions/total # of positions×100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul (1990) Proc. Natl. Acad. Sci. U.S.A. 87:2264–2268, modified as in Karlin and Altschul (1993) Proc. Natl. Acad. Sci. U.S.A. 90:5873–5877. Such an algorithm is incorporated into the NBLAST and XBLAST programs of Altschul et al., 1990, J. Mol. Biol. 215:403–0. BLAST nucleotide searches can be performed with the NBLAST nucleotide program parameters set, e.g., for score=100, wordlength=12 to obtain nucleotide sequences homologous to a donor or target nucleic acid. To obtain gapped alignments for comparison purposes, Gapped BLAST can be utilized as described in Altschul et al., 1997, Nucleic Acids Res. 25:33 89–3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., www.ncbi.nlm.nih.gov). Another preferred, non-limiting example of a mathematical algorithm utilized for the comparison of sequences is the algorithm of Myers and Miller, (1988) CABIOS 4:11–17. Such an algorithm is incorporated in the ALIGN program (version 2.0) which is part of the GCG sequence alignment software package.

The percent identity between two sequences can be determined using techniques similar to those described above, with or without allowing gaps. In calculating percent identity, typically only exact matches are counted.

5.2 Methods for Directed Gene Assembly

The methods of the invention, as described in detail herein, can be used for a number of purposes, such as: 1) reassembling genes from sequence-related members of gene families; 2) site-directed mutagenesis; 3) inserting or substituting sequences in a target gene to construct recombined vectors; and 4) combinations of these processes. Variant sequences resulting from any of these processes can, for example, be archived and/or tested for optimization of a desired phenotype. These methods are described in detail herein.

In general, the DGA method comprises the steps of: transferring a donor vector, optionally contained within a donor cell, as described in Section 5.1.1, above, into a target cell having a target vector containing a target gene or gene sequence of interest, as described in Section 5.1.2, above, allowing homologous recombination to occur between the donor vector and the target vector, and selecting for a target cell containing a variant of the target gene of interest. Conditions that allow homologous recombination to occur merely refer to standard growth or maintenance conditions for the particular cells being used in the particular instance. As also discussed above, the target gene or gene sequence of interest can, in an alternative embodiment, be integrated into the genome of the target cell.

Prior to the step of transferring the donor vector into the target cell, the donor sequences may be subjected to any of a variety of mutagenesis procedures in order to produce a pool of diverse donor sequences. A schematic of this strategy is shown in FIG. 6. Mutagenesis procedures are well known in the art. In one embodiment, donor vectors may be mutagenized either in vitro, prior to introduction into donor cells by in vitro mutagenesis protocols (e.g., Edward, 1996, Methods Mol. Biol. 57: 97–107). In another embodiment, donor vector may be mutagenized in in vivo, for example using *E. coli* mutator strains (see e.g., Horst et al., 1999, Trends Microbiol., 7:29–36; Miller and Michaels, 1996, Gene 179:129–32; Miller, 1998, 409:99–106). Some non-limiting examples of such mutator strains are mut D, mut S, mut Y, and mut M.

As described in Sections 5.2.1 and 5.2.2 below, selection for a target cell containing a variant gene can be accomplished be a one-step method or, preferably when the percentage sequence identity between the donor and target is less than 95%, a two step method. The one-step method selects for the product of the homologous recombination, i.e. a variant target gene. This selection can be direct or indirect, the former entailing selection for recombed sequences and the latter entailing selection against unrecombined target sequences. The two-step selection method entails, prior to selection for the variant target gene, the additional step of selecting for the intermediate of homologous recombination, a structure known as a co-integrant. Following selection of variant target molecules, the donor sequences can be segregated as described in Section 5.2.3, infra.

It is noted that multiple selections can be performed at any of the selection steps. For example, appropriate target and donor vectors can be designed such that a multiple selection for loss of a negatively selectable marker and a molecular selection (e.g., using amplification to select for a particular size of sequence) can be performed. Multiple selections can make possible the identification and isolation of particularly rare events such as, for example, identification and isolation of a somatic mutation in a population of wild type allele copies. A representative, non-limiting example of multiple selection is demonstrated in Section 6.5, below.

5.2.1 One-step Selection of Variant Target Molecule

Homologous recombination between the donor recombination module of the donor vector and the recombination module of the target vector gives rise to a variant target molecule. The one-step selection method of the variant target described hereinbelow is preferably used where the target and donor sequences being recombined share at least 95% sequence identity. Recombinant products may be selected in a number of ways, depending on the choice of selectable markers in the target vector, as described above in Sections 5.1.2.1.1 and 5.1.2.1.2. As described therein, recombinant variant modules maybe selected by placing sequences that are detrimental to cell growth under a controlled set of conditions, so-called conditional lethal sequences, within a region targeted (see Section 5.1.2.1.1), or by the elimination of a polar sequence (see Section 5.1.2.1.1).

Because the target vector has a negative selection marker between the first target sequence and the second target sequence, selection of a variant target molecule can simply entail selection against the negative selection marker, which is lost as a result of the homologous recombination process. Thus, in one embodiment, selection for recombinants is by a negative selection method, as described above in Section 5.1.2.1.2, above. This method comprises the steps of: (a) transferring a donor vector into a target cell, e.g., a bacterial cell, which is capable of homologous recombination, wherein (i) said donor vector comprises a donor recombination module comprising, in the following order from 5' to 3': a first donor DNA sequence and a second donor DNA sequence, and (ii) said target cell comprises a target vector comprising a target recombination module comprising, in the following order from 5' to 3': a first target DNA sequence; a negatively selectable marker; and a second target DNA sequence, wherein said first donor DNA sequence is homologous to said first target DNA sequence, and said second donor DNA sequence is homologous to said second target DNA sequence; and (b) selecting for a population of target cells which do not contain the negatively selectable marker, so that a population of a variant sequence modules in cells is generated. The cells undergoing DGA are subjected to conditions that allow homologous recombination to take place. Conditions that allow homologous recombination to occur merely refer to standard growth or maintenance conditions for the particular cells being used in the particular instance. Such conditions are well known to the skilled artisan.

Generally, selecting for target cells that do not contain the negatively selectable marker is accomplished by subjecting the cells to conditions that do not allow growth of donor cells or of target cells that still contain the negatively selectable marker (i.e., have not undergone recombination with the donor vector resulting in loss of the negatively selectable marker). To ensure loss of donor cells, for example, a selectable marker (e.g., a tetracycline resistance-encoding element) can be included in the chromosomal background of the target cell, but be absent from the donor cell. Imposing appropriate selective pressure (e.g., inclusion of tetracycline) results in selected loss of donor cells. In a variation of this method, the target recombination module is present in the target cell integrated into the target cell genome. Preferably, the target recombination module is integrated in a manner that readily allows excision or isolation of the module out genome, i.e., via flanking unique restriction sites or by specific amplification of the module.

In an alternative method, a positive selection method, as described above in Section 5.1.2.1.2, above, is used to select for recombinants. In this case, a first non-functional fragment of a positively selectable marker flanks the donor recombination module, and a second non-functional fragment of the marker flanks the target recombination module. Appropriate recombination between the marker fragments and between the donor and target recombination modules results in reconstruction of a function marker. Thus, selection for the presence of a functional positively selectable marker selects for a recombinant target gene of interest. This method comprises the steps of: a) transferring a donor vector into a target cell, e.g., a bacterial cell, which is capable of homologous recombination, wherein i) said donor vector comprises a donor recombination module comprising, in the following order from 5' to 3': a first non-functional fragment of a positively selectable-marker; a first donor DNA sequence; and a second donor DNA sequence; ii) said target cell comprises a target vector comprising a target recombination module comprising, in the following order from 5' to 3': a second non-functional fragment of the positively selectable-marker; a first target DNA sequence; and a second target DNA sequence, wherein said first donor DNA sequence is homologous to said first target DNA sequence, and said second donor DNA sequence is homologous to said second target DNA sequence, and recombination between said first non-functional fragment of the positively selectable-marker and said the second non-functional fragment of the positively selectable-marker results in a functional positively selectable marker; and (b) selecting for a population of target cells which contain the positively selectable marker, so that a population of a variant sequence modules in the cells is generated. In a variation of this method, the target recombination module is present in the target cell integrated into the target cell genome. Preferably, the target recombination module is integrated in a manner that readily allows excision or isolation of the module out genome, i.e., via flanking unique restriction sites or by specific amplification of the module.

5.2.2 Two-step Selection of Variant Target Molecule

In another embodiment, a two-step procedure is used to select for the product of homologous recombination, which entails selection of an intermediate state in the process followed by selection of the product of homologous recombination. In such an embodiment, the intermediate state is one in which the target cell contains both the donor vector and the target vector. Without wishing to be bound by any theory or mechanism, it is believed that this intermediate state more particularly involves an intermediate of the homologous recombination process referred to as a co-integrant. In the latter embodiment, a fourth element is required, namely a positively selectable sequence in the donor DNA to allow for selection of the intermediate state. This sequence can be present at any position of the donor vector that does not interfere with standard vector functions (e.g., vector replication).

The invention encompasses, first, a method for generating a population of variant sequence modules in cells, e.g., bacterial cells, said method comprising: (a) transferring a donor vector into a target cell which is capable of homologous recombination, wherein (i) said donor vector comprises a donor recombination module comprising, in the following order from 5' to 3': a first donor DNA sequence and a second donor DNA sequence, and additionally comprises a positively selectable marker; and (ii) said target cell comprises a target vector comprising a target recombination module comprising, in the following order from 5' to 3': a first target DNA sequence; a negatively selectable marker; and a second target DNA sequence, wherein said first donor DNA sequence is homologous to said first target DNA sequence, and said second donor DNA sequence is homologous to said second target DNA sequence; (b) selecting for target cells that contain the positively selectable marker; and (c) selecting for a population of target cells which do not contain the negatively selectable marker, so that a population of variant sequence modules in cells, in particular, the target cells, is generated. Generally, selecting for target cells that do not contain the negatively selectable marker is accomplished by subjecting the cells to conditions that do not allow growth of donor cells or of target cells that still contain the negatively selectable marker (i.e., have not undergone recombination with the donor vector resulting in loss of the negatively selectable marker). To ensure loss of donor cells, for example, a selectable marker (e.g., a tetracycline resistance-encoding element) can be included in the chromosomal background of the target cell, but be absent from the donor cell. Imposing appropriate selective pressure (e.g., inclusion of tetracycline) results in selected loss of donor cells. In a variation of this method, the target recombination module is present in the target cell integrated into the target cell genome. Preferably, the target recombination module is integrated in a manner that readily allows excision or isolation of the module out genome, i.e., via flanking unique restriction sites or by specific amplification of the module.

In another embodiment, the invention provides a method for generating a population of a variant sequence modules in cells, e.g., bacterial cells, said method comprising:(a) transferring a donor vector into a target bacterial cell which is capable of homologous recombination, wherein (i) said donor vector comprises a donor recombination module comprising, in the following order from 5' to 3': a first non-functional fragment of a first positively selectable marker; a first donor DNA sequence; and a second donor DNA sequence, and additionally comprises a second positively selectable marker; (ii) said target cell comprises a target vector comprising a target recombination module comprising, in the following order from 5' to 3': a second non-functional fragment of the positively selectable marker; a first target DNA sequence; and a second target DNA sequence, wherein said first donor DNA sequence is homologous to said first target DNA sequence, and said second donor DNA sequence is homologous to said second target DNA sequence, and recombination between said first non-functional fragment of the selectable marker and said second non-functional fragment of the selectable marker results in a functional selectable marker; (b) selecting for target cells that contain the second positively selectable marker; and (c) selecting for a population of target cells which contain the first functional positively selectable marker, so that a population of a variant sequence modules in the cells is generated. In a variation of this method, the target recombination module is present in the target cell integrated into the target cell genome. Preferably, the target recombination module is integrated in a manner that readily allows excision or isolation of the module out genome, i.e., via flanking unique restriction sites or by specific amplification of the module.

With respect to co-integrants, without wishing to be bound by any theory or mechanism, co-integrant formation is driven by homologous recombination in regions of shared homology. Co-integrants are intermediates of homologous recombination that can be selected for by subjecting target cells into which a donor vector has been transferred to conditions that select for a marker present on a target vector. Co-integrants are unstable in the absence of selective pressure. Co-integrant structures can resolve in one of two different ways; the reverse reaction yields the original donor and target, and a forward reaction produces a variant target. Without wishing to be limited by any particular theory or mechanism, in the methods described herein, it is believed that placement of the negatively selectable marker in the target and subsequent selection against said marker drives the recombination event in the forward direction. Recombination between regions of homology either side of the site of the negative selection insert will lead to a recombination event that directs the assembly of the gene with the desired new segment of DNA. FIG. 14 shows how the process of co-integrant formation followed by DGA-selected resolution breaks the process illustrated in FIG. 3 into sequential and separable steps.

In a preferred version of this embodiment, the donor vector is a suicide vector (see Section 5.2.3, below) that replicates only in the donor cell, not the target cell. Use of a suicide vector, coupled with selection for the second positively selectable marker favor co-integrant formation.

The selection for and maintenance of co-integrants can be useful in generating diversity, as a single co-integrant can give rise to a family of recombinant molecules. Specifically, selection for co-integrant formation selects for a first recombination event, and co-integrant resolution can be accomplished via recombination at a number of positions, thereby creating a family of sequence variants. A representative example of this is presented, below, in Section 6.5.1.

Thus, in one embodiment of the present invention, selection of a variant target molecule comprises two steps. In the first step, selection for the co-integrant is achieved by selecting for a positively-selectable marker on the donor vector. In the second step, selection for unrecombined target vectors is achieved as described in Section 5.2.1 above, for example, by selecting against a negatively-selectable marker in the target module.

5.2.3 Segregation of Donor Sequences

In certain embodiments of the invention, selection for the segregation of donor sequences, that is, loss or removal of unrecombined donor sequences and non-recombination module sequences, after selecting for cells containing recombinant variant modules is desired. In one embodiment, both replication functions and transfer functions are provided from genes provided in trans to the donor vector to prevent replication and transfer of the donor vector following in the target cell (Metcalf et al., 1994, Gene 138:1–7). Where a reciprocal homologous recombination event replaces a conditionally lethal, negatively-selectable marker, recombination may result in exchange of the conditionally lethal marker to a second replicon. If the second replicon has a conditional origin of replication, then loss of the counter-selected marker can be facilitated by conditions that are incompatible with replication of the second replicon (Penfold and Pemberton, 1992, Gene 118:145–6). This strategy is outlined in FIG. 10. In a preferred embodiment of the present invention the donor vector replicates in the donor cell but fails to replicate in the target cell. The use of such a suicide vector facilitates selection for recombinants when selecting for a negatively selectable marker, because the donor vector is lost from the target cell following recombination.

5.2.4 Phenotype Optimization

Once sequence variants are generated, the variant sequences or genes can be screened and optimized for a desired phenotype of interest. The selection process drives the optimization of the sequence or gene during iterative rounds of the process. The selection method chosen will be depend on the nature of the target sequence and the desired property to be optimized, and will be apparent to the skilled artisan in the particular area of interest. The sequences can be subjected to any selective pressure appropriate to optimize the particular phenotype of interest. Selection can occur in the target cells containing the variant sequences, or can be performed in a secondary cell type, either in culture or in vivo. Representative, non-limiting, examples of the types of phenotype optimization the DGA methods of the present invention can be used in conjunction with are presented hereinbelow.

In one embodiment, for example, the variant target sequence may encode a transcription factor for which the property of increased ability to activate a particular target gene is desired. In this case, the selection system could comprise a reporter gene, operatively linked to a transcription factor binding site, such that binding of the transcription factor results in expression of the reporter gene. The assay can comprise identifying a variant transcription factor that results in increased activation of the reporter gene relative to the target gene, i.e. the wild-type transcription factor. Such an assay may be accomplished either in the target cell itself, or the recombinant variant gene may be transferred to a secondary host cell for expression and selection.

Alternatively, the variant target sequence can encode an enzyme whose activity is to be optimized (e.g., substrate can be modified and/or activity can be increased or attenuated). For example, in the case of industrial enzymes, the phenotype of an enzyme of interest can be subjected to appropriate selective pressure to optimize such phenotypic properties as the substrate specificity, temperature resistance, salt tolerance, pH range, or solvent tolerance or otherwise extend the environmental parameters under which enzymes that have industrial applications, including but not limited to, proteases, esterases, oxidases, dehydrogenases, catalases, lactases, or other such enzymes function.

In the agricultural area, for example, variant target sequences can be subjected to appropriate selective pressures to optimize properties of food storage proteins to improve quality traits of a crop. For example, the DGA methods of the present invention can be utilized to alter genes encoding pathogen resistance determinants to extend the range of pathogen resistance, or to modify sequences involved in e.g., salt, drought, and temperature tolerance to modify (e.g., enhance) growth characteristics of a plant of interest.

In the medical area the DGA methods of the invention can, for exampe, be used to optimize antibody characteristics (e.g., enhance, modifiy antigen specificity and/or improve binding), to produce a large pool of antibody diversity in vitro, and/orto humanize antibodies, e.g., rodent antibodies. Further, proteins or polypeptides exhibiting therapeutic efficacy or potential can be optimized via the DGA methods of the present invention. For example, enzymes with therapeutic applications can have their reaction parameters made more amenable to the particular therapeutic situation. Further, proteins, e.g., growth factors, can be optimized to beneficially alter efficacy, production or range of biological activities. Still further, the DGA methods of the present invention can be used to reduce the immunogenicity of protein therapeutics, or to enhance the antigenicity of immunizing antigens.

5.2.5 Directed Gene Assembly Variations

The DGA methods described in Section 5.2 sets forth the basic elements of DGA. Presented in this section are a few of the variations or modifications of the basic DGA method, e.g., methods for production of complex populations of variants or variants having additional sequences that do not solely correspond to sequences homologous to sequences originally present in the target modules, that can also be routinely practiced.

For example, in one embodiment, a target recombination module comprises more than one negatively selectable marker, in order to direct recombination into more than one region of the target vector. An example of a target vector comprising two negatively selectable markers, galE and sucB, in a single target vector is illustrated in FIG. 7. FIG. 7 shows a target recombination module with two negatively selectable markers inserted into the coding sequence of the target gene. Such sequences can be constructed by any method described herein for construction of target recombination modules containing a single negatively selectable marker, or by standard techniques well known in the art. For example, methods can be employed that comprise cloning into available restriction sites or transpositional insertion using insertion elements containing a negatively selectable marker.

In a non-limiting example of such an embodiment, first, a population of bacteria containing a target vector is mixed with a population of bacteria containing a library of donor vectors comprising gene or sequence fragments from a variety of genes related to the target gene (that is, represent homologs of, or at a minimum, exhibit sufficient sequence homology to allow homologous recombination with target gene sequences). In FIG. 7, two each of two family members is used for illustration purposes. Selection against the donor cells using the first negatively selectable marker on the target vector (in the example, gal) selects for and thereby produces recombinant molecules. Specifically, each donor vector can recombine with the target vector, resulting in replacement of the sequence flanking the first negatively selectable marker sequence by donor DNA. Different variant sequences are produced in each case, provided there is variation, e.g., allelic variation, between different exchange points. This principle is illustrated in FIG. 7, showing two possible products with each donor vector. The product of the first exchange event still contains the second negatively selectable marker and, therefore, the target gene product itself still cannot be expressed. Nonetheless, these intermediate variant sequences can be produced and selected for because selection was exerted for a recombination event, independent of the nature of the target gene product, illustrating one of the advantages of the DGA methods of the present invention.

The variant target sequences generated via the first exchange can then become substrates for a second set of homologous recombination exchanges. (It is noted that, alternatively, such sequences can be archived for future use in another DGA application.) The second round of recombination produces and selects for taget recombination modules that have undergone recombination to lose the second negatively selectable marker. If desired, the resulting variant target sequences can then be expressed to assess the properties of the variant target gene product produced therefrom. This procedure is illustrated with one of the products of the first exchanges illustrated in FIG. 7. As FIG. 7 demonstrates, each individual member of the first exchange has the potential to produce an array of variant sequences. The procedure employed, therefore, provides for the combinatorial amplification of variant sequences.

FIG. 7 illustrates the process with a single target and two donors. Larger libraries of donors and/or targets can be used to produce vastly larger ensembles of product molecules. It is also possible to more carefully control the process by restricting the size of the donor DNA sequences, thus restricting the extent of the regions participating in the exchanges. The final products in such a strategy can, for example, be achieved employing a sequential procedure wherein a single negatively selectable marker is employed for the first product series and an intervening step is used to introduce a second collection of negatively selectable markers prior to the second round of targeting as described below, and illustrated in FIG. 8.

In another embodiment, the DGA methods of the present invention can be used to insert a heterologous sequence into a target gene or sequence, or replace a target gene or sequence with a heterologous gene sequence. The recombination events replacing the negatively selected insert require homology flanking both sides of the insert. Just as flanking homology can delete intervening non-homologous material, flanking homology can be used to introduce non-homologous sequences as inserts into a sequence, or as substitutions in a deletion-insertion process replacing existing segments of DNA. The fundamentals of such a procedure are illustrated in FIG. 9. Insertion of sequences is useful, for example, for introducing novel sequences that can add function to a protein, e.g. a second activity in a sequential enzyme pathway or specific cellular localization functions. For example, sequences encoding additional protein domains can be introduced into the coding region of a target gene sequence of interest. Further, additional selectable markers can be introduced into a target gene or sequence of interest via such an embodiment, thereby creating or modifying a target vector.

In addition to insertions of new sequences, a directed homologous recombination event can be used to replace segments of the target recombination module with sequences from the donor recombination module. The substitution process can, for example, execute the combinatorial replacement of sequences that are structural homologs of segments, e.g., segments in a gene family, that may fail to have the sequence homology required for the direct homologous replacement in a re-assortment process. For example, such an embodiment can result in "domain swapping," that is, sequences encoding a particular domain can be substituted for sequences encoding a different, either related or unrelated, domain. Such structurally related stretches, with low homology will also in many instances fail to provide adequate substrates for PCR re-assortment strategies. Insertional substitution can substantially extend the scope of sequences that can be directed to participate in a combinatorial re-assortment process.

Still further, the DGA methods of the present invention can also be used to generate new target vectors by, for example, moving negatively selectable markers from donor vectors to target vectors. To accomplish this, selectable markers are placed in the target recombination module. The resulting vector can then be used as a donor vector in a DGA procedure to new target vectors. A representative example of this is demonstrated in Section 6.5.3, below.

This process of "variant"—variant target recombination module production can be iterated any number of times by performing genetic crosses without in vitro manipulations. The process both uses and can produce reagents that may be archived. The method is illustrated in FIG. 8.

In another embodiment, the DGA methods of the present invention can be used to isolate specific sequences of interest from a library of sequences. For example, a library of donor vectors can be presented to a collection of target cells containing a target vector with a target recombination module. Selection can be designed such that the only cells allowed to grow are those target cells that have undergone selection with a donor DNA sequence. Because such a recombination event requires a minimum amount of homology, such a scheme serves to identify sequences within the library that contain homologous sequence. Thus, DGA allows, for example, evolutionary re-assortment from libraries of sequences without the need for prior identification and isolation of homologous candidate sequences. Further, the donor DNA sequences need not have extensive homology with the target DNA sequences, as long as sufficient homology exists to support homologous recombination. Limited homologies across gene segments are sufficient, especially when cells, e.g., mutL cells, that lack mismatch repair function, are utilized. Such an embodiment can be used, for example, to capture homologous domains from otherwise dissimilar proteins. This strategy is illustrated in FIG. 11.

Multiplexing embodiments of the DGA methods of the present invention can readily be practiced. For example, DGA can be used to produce sequences that encode new proteins, by, e.g., replacing particular structural motifs in a target protein with new sequence, using a DGA re-assortment or insertional substitution strategies. The context of the structural motif is likely to be important, however, and adjustments may be required to create a functional polypeptide. However, using conventional protocols, the suitability of the structural motif in the new context of the novel protein can be evaluated in one context at a time. By combining mutagenesis of the donor or target vector with a re-assortment or insertional substitution procedure, multiple novel proteins comprising an array of variants in a variety of contexts can routinely be evaluated.

The multi-component nature of the DGA process lends itself to combinatorial strategies. These combinatorial strategies can take place over an extended period of time and components of the process, because they are actual living replicating entities—cells, e.g., bacteria, containing the donor and target vectors—may be archived (see below) and amplified as desired in subsequent iterations of an experimental series. It is also possible that a target gene produce may have a variety of potential evolutionary endpoints, in which case, entire sets of vectors, e.g., target vectors, can be reused in subsequent series of phenotype optimization experiments with different goals and results based on the application of different selective pressures and different subsequent direction of further sequence variation via DGA.

Conjugational gene transfer, a preferred procedure for transfer donor DNA into a target cell, is amenable to automation. Using liquid handling automation individual members of a donor library can be arrayed. Again employing liquid handling automation, an arrayed collection of donors may be individually mixed with a target. The behavior of the products resulting from the DGA exchanges can then be determined for an arrayed collection of products with reference maintained to the original donors that produced individual targets.

DGA can be used to query a domain or structural motif to see if it can substitute for an existing sequence in a target protein. To query a candidate sequence, a negatively selectable marker is be placed into a segment encoding the portion of the test protein with the domain (or structural motif) in question. DGA is then be used to drive the recombination process. If the queried candidate sequence has sufficient homology to drive the process it can be recombined directly from a donor vector. If the queried candidate sequence is of distant homology or a non-homologous structural homologue (candidate), it can be embedded into homologous sequences flanking the selectable marker as described above. In either instance counter-selection against the targeted selectable marker can be used to drive the recombination process directing the gene assembly. DGA drives the production of the gene product and the product can be tested and compared with the parental gene (summarized in FIG. 8). Relative activities (defined by the specifics of the test protein) define the relative ability of the candidate sequence to substitute for the domain (or structural motif) in the test protein. It is also possible to combine the above procedure with mutagenesis to assess the "sequence space" neighboring the precise input combination. In this way information about the full potential of the queried motif in the new context can be derived.

5.3 Libraries

The invention further provides libraries suitable for the practice of directed gene assembly. Such libraries can be donor or vector libraries and can comprise a plurality of any of the donor or target vectors of the invention, including vectors comprising variant target sequences that have been produced via DGA. Such libraries can also comprise variant target gene or target gene sequences produced via DGA that no longer contain intervening selectable markers and encode variant target gene products, including optimized variant target gene products. Such libraries can also comprise cells containing co-integrant configurations that can, at a desired point, be resolved. Libraries can also comprise a plurality of archived sequences or modules, (see Section 5.4, below) optionally present within cells.

In one embodiment, the vectors of the library are present within cells (e.g., donor cells for donor vectors and target cells for target vectors), e.g., bacterial cells.

In another embodiment, the library vector, preferably the donor library vectors, is a suicide vector. In yet another embodiment, the vectors of the donor libraries contain defective conjugative transfer sequences. In another embodiment, such vectors are present in donor cells that complement the conjugative transfer sequence defect.

In still another embodiment, the members of the library are arrayed. In another embodiment, the members are arrayed in a 96 (e.g., 8×12), 384 (e.g., 16×24), or a 1536 (e.g., 32×48) matrix or plate, e.g., microtiter plate. In yet another embodiment, the donor library is present in a multiplicity of cells, e.g., bacterial cells, each cell containing a member of the library the members of which are arrayed. In another embodiment, such cells are arrayed in a 96 (e.g., 8×12), 384 (e.g., 16×24), or a 1536 (e.g., 32×48) matrix or plate, e.g., microtiter plate.

Donor vectors generally have a greater potential for subsequent reuse than target vectors. Firstly, the requirements of the donor vector are less constraining as there are no requirements for second origins (as with shuttle vectors often utilized as target vectors) or expression-related sequences. Donor libraries, therefore, can be universal as they can be be compatible with many target libraries. In such universal donor library embodiments, it is generally preferable to use smaller donor DNA sequences as such sequences are more likely to be useful and usable in multiple proteins.

For example, proteins are comprised of a finite variety of structural motifs (Thornton et al., 1999, J. Mol. Biol. 293: 333–42). Sequences encoding motif-sized pieces in a donor library, for example, are likely to have uses in a large variety of proteins. It is possible to directly pursue the acquisition of a collection of protein motifs in a specialized donor library as described, above, in Section 5.3.

Further, as discussed above, in Section 5.3, homology-based isolation of gene sequences from libraries is a powerful application of DGA technology. Using this application a collection of gene sequences can be created in a donor vector producing a plurality of potential donor sequences. Such pluralities can have many applications across a variety of targets and, hence, represent valuable libraries and archives (see below). For example DNA from an extremeophile such as a thermophilic organism can be used to construct a library that is screened for sequences able to replace segments in enzyme X, based on homology, with the goal of arriving at a more thermal resistant enzyme X. In addition, once made, such a library can prove useful for many subsequent experimental series with other enzymes.

In one donor library embodiment, therefore, the donor vectors of the library comprise related donor DNA sequences. For example, in such a library, the donor DNA is derived from: different homologs of the same gene or gene portion from different species; different members, or portions thereof, of a particular gene family exhibiting amino acid similarity; or different DNA sequences encoding polypeptide domains exhibiting amino acid similarity.

When products with desired properties are identified, the donors that were used in those specific crosses can be isolated and set aside to produce a specialized extracted library (FIG. 12). An extracted library is a library containing modules or sequences of similar or related function. The sequences of such an extracted library are likely to provide similar function or functions to proteins. Members of such extracted libraries can, for exmple, be accumulated during the course of experiments with specific gene product goals. Extracted libraries can also be produced as part of studies designed to isolate protein building blocks (structural motif or domains) for use in phenotype optimization and directed evolution experiments employing DGA strategies. Extracted libraries (regardless of the means used to assemble them), therefore, provide preformatted donor reagents that have described uses in specific contexts and, as such, can also represent archived modules (see the next section).

5.4 Archives

Discussed above and in the examples provided herein are methods and compositions relating to target vectors, donor vectors, and DGA methods. The present invention is also directed to archived sequences of any sequence or module produced via such methods. An archived module, as used herein, refers to a donor DNA sequence or target DNA sequence, whether or not the target sequence has undergone DGA or phenotype optimization, where the sequence comprising the archived module is known or has been demonstrated to encode a protein segment or domain that provides a particular function (e.g., ligand binding, enzymatic activity, structural activity), and has been stored and catalogued (archived), e.g., for future use, such as future use in similar or different DGA situations. The size and numbers of archived modules, and the information associated with the archives limited only by the number of experiments performed.

The bi-molecular nature of the methods described herein allows reagents to be used repeatedly, e.g., as part of a sequential combinatorial process. It also allows the reagents, once created, to be archived. One of the principle advantages of the DGA approach is, in fact, the ability to recycle reagents in subsequent iterations of an experiment. This can be extended beyond a simple set of experiments across many experiments creating an archive of reusable reagents. Many different types of archives are possible ranging from target and donor libraries simply frozen for potential future use, to extracted collections with proven function or use, and extending to archives of structural motifs and domains deliberately isolated as building blocks for rational protein design.

With time and multiple iteration of the process, both within a specific set of experiments and across many different experiments, information about the archived modules is built. Preferably, therefore, archived modules have a history relating to their behavior in previous DGA procedures. That is, in addition to the module itself, there is a store of information relating to the sequence and function history of the archived module. This history grows over time and allows subsequent DGA iterations or projects to be directed by the information accumulated. That is, it is such a history in a related series of experiments that can form the data, or part of the data, analyzed to direct iterative rounds of variant sequence production and phenotype optimization (directed evolution).

For example, in a particular round of DGA, the modules exchanged represent homologous segments of proteins, or at least contain flanking areas of homology. New combinations represent new re-assortments of structural components. Information about how a particular sequence behaves in a given context, or which sequences are functional or optimal in specific context(s), accumulates, and over time provides a database with information about the structural domains and motifs of the proteins involved that describe their use or activity, therefore, suggesting futures uses for the sequences in subsequent phenotype optimization and directed evolution. It is noted that this capacity to produce such archived module collections with associated data further distinguishes the methods of the present invention from random complex permutation sampling approaches to directed evolution.

Archived modules can routinely be frozen and catalogued. In a preferred embodiment, the archived module is present as part of a vector (generally a donor or target vector, with a donor vector being preferred). In another preferred embodiment, the archived module is present within a cell.

Where the donor vector is contained in a host bacterium for conjugation-mediated transfer, dramatic miniaturization can be employed as a single nanoliter of material contains $10^3$ organisms. The growth rate of bacteria (1 generation every 15–20 minutes) allows aliquots to be amplified by a factor of $10^6$ in six hours, and can permit 75 generations of "evolution" to be achieved each day. Simple liquid handling robotic systems can be employed to distribute and mix bacterial populations permitting the plasmid-based donor/target approach to take full advantage of the developments in high throughput screening technologies that were achieved in the 1990s (See, e.g., Cox et al., 2000, Prog. Med. Chem. 37: 83–133).

5.5 Databases

The DGA approaches of the invention generate data relating to, e.g., the behavior of structural motifs and protein domains as, for example, discussed above for archived modules. Such information represents a database of information. As such, the present invention still further provides a computer readable medium having a database recorded thereon in computer readable form, wherein said database comprises one or more module profiles and wherein each module profile describes a phenotype in a DGA assay, and wherein each module profile is associated with a particular vector in a particular target cell.

For example, if the donor input materials are arrayed, the results obtained about the arrayed individual products can be used (see above) to produce extracted libraries. The assembly of extracted libraries with modules of predefined uses will allow the "directed evolution" process to be directed, not only by the results of iterative screening and selections, but also by accumulated knowledge about extracted libraries and our growing understanding of protein structure. The DGA strategy of the present invention naturally lends itself to an eventual integration of directed evolution technologies with the theoretical developments in the field of rational protein design (Regan, 1999, Curr. Opin. Struct. Biol. 9: 494–499).

6. EXAMPLES

The following examples demonstrate construction of a donor vector series (Section 6.1) and a recipient donor series (Section 6.2) into which bacterial subtilisin genes were cloned, subjecting the bacterial subtilisin genes to DGA and two-step selection of variants: first, selection of co-integrant (Section 6.4), and selection of variant modules (Section 6.5). Section 6.6 demonstrates that the foregoing procedures resulted in the generation of a collection of functional variants of subtilisin molecules.

6.1 Donor Vector

6.1.1 The Creation of the pGPG Plasmid Series

A universal pre-donor plasmid, pGPG, was designed for use with the DGA-related subject matter described herein. Briefly, the pGPG plasmid was designed to have: 1) a minimum amount of vector sequence homologous to other standard vectors; 2) a positively selectable marker; and 3) a multiple cloning site into which donor sequences of interest can easily be introduced. As noted below (Section 6.2.4) such a vector can also be utilized in the construction of target vectors.

The pGPG plasmid is a derivative of the R6K plasmid. The plasmid R6K can be transferred between strains by conjugation (Macrina et al., 1974, J. Bacteriol. 120(3): 1387–1400). A significant number of derivatives of R6K have been created, among which are plasmids defective for conjugation (Nunez et al., 1997, Mol. Microbiol. 24:1157–68), replication (Kolter, 1981, Plasmid 5(1):2–9), or for both conjugation and replication (Metcalf et al., 1994, Gene 138:1–7). The plasmids can be rescued by providing the conjugation and/or replication functions in trans. An R6K derivative where replication and conjugation functions are provided in trans is desirable as a donor vector. Once such a derivative is transferred to a target strain which lacks the replication and conjugation functions, the vector DNA exists transiently pending dilution following bacterial growth. The vector DNA is available for recombination, but (in the absence of recombination) will rapidly be lost and will not replicate or participate in subsequent conjugational events. One such plasmid, pGP704 (salmonella.org.vectors/pgp704/), was used as starting point for the creation of the pGPG series of vectors suitable for DGA.

To eliminate sequences from the donor common to most commonly utilized vectors and, at the same time provide a useful selective marker, the plasmid pGP704 was partially digested with Bam HI to produce a 2216 base pair fragment which was ligated with a 865 base pair Bam HI fragment from the plasmid p34SGM (Dennis and Zylstra, 1988, J. Applied Environmental Microbiology 64(7):2710–2715) containing the aacC1 gene and its promoter encoding the function conferring resistance to gentamycin resistance. The resultant ligation mixture was transformed into the π replication proficient host OTG28 (for all strains referred to herein, see Section 6.3, below) and plated on Luria agar selecting gentamycin (10 μg/ml) to isolate the plasmid pGPG6 (FIG. 15).

Further modifications to the pGPG6 were made to produce cloning vectors with unique multiple cloning sites ("MCS"; MCS1, pGPG7 and MCS2, pGPG8). pGPG6 was first cut with SmaI and Sac I, terminal nucleotides were removed (Sac I site) and the resultant molecule was circularized with ligase to produce pGPGSS (FIG. 15). pGPGSS was digested with EcoRI, and synthetic oligonucleotides MCS1F (SEQ ID NO:1) and MCS1R (SEQ ID NO:2) were annealed and then ligated into the EcoRI cut pGPGSS to produce pGPG7p (FIG. 14). In a second manipulation, primer directed mutagenesis (Stratagene La Jolla Calif.; QuikChange XL) using primers BglKF (SEQ ID NO:3) and BglKR (SEQ ID NO:4) was performed according to the vendor's procedures to remove the Bgl II site from the gentamycin resistance sequence producing pGPG7. A further derivative with an alternative multicloning site was made was by cutting pGPG7 with EcoRI and AscI and ligating in annealed CC_UPPER (SEQ ID NO:5) and CC_LOWER (SEQ ID NO:6) to produce pGPG8 (FIG. 15).

6.1.2 Production of Donor Vectors: Cloning Subtilisin Sequences into pGPG

A variety of donor vectors were generated by cloning subtilisin sequences from various species into the MCS of pGPG plasmids. Construction of two representative examples of such subtilisin donor vectors is described herein. In addition to the two representative examples described in detail herein, a number of other subtilisin sequences from B. subtilis and B. lichenformis strains were also successfully cloned into pGPG plasmids using completely analogous procedures.

Six hundred base pair fragments encoding the catalytic and substrate-bindings portions of subtilisins were PCR amplified from the strains 3A13 (*B. subtilis* variety amylosacchariticus) and 5A20 (*B. licheniformis*) using two internal primers (upper—SEQ ID NO:7 and lower—SEQ ID NO:8). The PCR products were cloned into a pGEM derivative using the pGEM easy T vector (Promega; Madison, Wis.), which employs a T/A (Clark, 1988, Nucl. Acids Res. 16:9677–86) cloning strategy, according to the vendor's protocols. The *B. subtilis* clone was digested with EcoRI and the resulting fragment subcloned into the EcoRI sites of pGPG7 to produce pGPG7-3A13. The *lichenformis* clone was digested with Spe I and Sph I and the resulting fragment subcloned into the Xba I and Sph I sites of pGPG7 to produce pGPG7-5A20. The DNA sequences of the *lichenformis* and *subtilis* inserts (SEQ ID NOs:19 and 21, respectively) were determined by standard procedures and are shown in FIG. 16. The two clones encode protein fragments (SEQ ID NOs:20 and 22, respectively) with 8 and 13 amino acid differences relative to the corresponding 200 amino-acid sequenced coding regions of the respective *lichenformis* and *subtilis* subtilisin target sequences described below.

6.2 Target Vectors

6.2.1 Pre-target Vectors

Construction of pre-target vectors capable of driving expression of subtilisin sequences was performed described herein. The vectors are termed pre-target vectors because no negatively selectable marker had yet been introduced into the target sequences present on the vector. Target vector construction (whereby the negatively selectable marker is introduced into the target sequences) is described in the following section.

The vectors described in this section were constructed as derivatives of the vector pWH1520 (MoBiTec Gmbh, Götingen, Germany). pWH1520 provides selection in both *E. coli* (ampicillin resistance) and *B. subtilis* (tetracycline resistance) as well as separate replication origins that function in these bacteria. In addition pWH1520 provides a xylose-regulated promoter (Rygus and Hillen, 1991, Microbiol. Biotechnol. 35:594–599) that is expressed in *B. subtilis*. To verify that subtilisin proteases can be expressed in this system and thereby provide an expressible target for DGA with both the *subtilis* and *lichenformis* subtilisins, intact complete *lichenformis* and *subtilis* protease coding sequences were PCR cloned from *lichenformis* (ATCC No. 14580, ATCC Manassas, Va.) and *B. subtilis* (3A1; BGSC Department of Biochemistry, The Ohio State University Columbus, Ohio). Subtilisin from *lichenformis* was cloned using *B. lichenformis* Subtilisin forward and reverse primers (SEQ ID NOS:9 and 10) and subtilisin from *B. subtilis* was cloned using *B. subtilis* forward and reverse primers (SEQ ID NOS: 11 and 12) using standard PCR conditions. Both set of primers contain appropriately oriented Kpn I and Bgl II sites, allowing the direct cloning of the PCR products as transcriptional fusions into Kpn I/Bgl II cut pW1520. Clones were first verified in *E. coli* by restriction analysis and the coding sequences of both genes were then determined by standard DNA sequencing procedures. The sequences of the *B. lichenformis* gene and encoded protein (SEQ ID NOs:13 and 14) and *B. subtilis* subtilisin genes and encoded proteins (SEQ ID NOs:15 and 16) demonstrated minor variations from those published in GenBank (see FIG. 17).

The functional nature of these clones was assessed by transformation (tetracycline at 15 μg/ml selected) into the subtilisin-defective *B. subtilis* host 1A751 (Apr-, Npr-; BGSC Department of Biochemistry, The Ohio State University Columbus, Ohio). Both plasmids promoted robust clearing zones on standard casein-agar plates (Maerki et al., 1984, J. Chromatogr. 283:406–411) when supplemented with 2% xylose. In the absence of xylose the *B. subtilis* clone (pWHsub) produced no zone while the *lichenformis* clone (pWHlic) produced a reduced zone of clearing, indicating a substantial level of constitutive expression. The control plasmid pWH1520 (no insert) failed to demonstrate any zone with (2%) or without xylose.

6.2.2 Selectable Marker Modules

A cassette containing the negatively selectable galactokinase (GalK) gene and positively selectable aadA gene conferring spectinomycin resistance was generated (Gal-Spec cassette; Section 6.2.3, below) for incorporation into a target vector. With respect to GalK, the GalK gene is a negatively selectable marker because, in strains with a defect in both the galactose kinase gene (galK) and a defect in the galactose epimerase gene (galE), expression of the GalK gene in the presence of galactose is lethal. When GalK is present in a target gene, therefore, selection for growth in the presence of galactose, represents selection for recombination within the target recombination module that effects loss of GalK. A cassette containng the negatively selectable sucrase gene and selectable npt 1 conferring kanamycin resistance was also incorporated into a target vectors, as described in Section 6.2.5, below.

6.2.3 Gal-spec

The Gal-Spec cassette was constructed in the vector pMOD (Epicentre; Madison, Wis.) that contains a multi-cloning site (MCS) between inverted19-bp repeats from the Tn5 transposon. A galactokinase-containing fragment was PCR isolated from the plasmid pKG1800 (Menzel and Gellert, 1987, J. Bacteriol. 169(3):1272–78) using the following: an upper primer (SEQ ID NO:17) and a lower primer (SEQ ID NO:18). This PCR product was digested with BglII to produce a fragment ready for cloning. Digestion of the plasmid pHP45 omega (Fellay et al., 1987, Gene 52:147–54) with Bam HI and gel purification of the aadA harboring 2028 base pair fragment provides DNA containing the aadA gene which confers spectinomycin resistance. The cassette was produced by simultaneously ligating the Bam HI cut pMOD, the BglII flanked galactokinase-containing PCR product and the Bam HI bracketed aadA gel purified fragment. Clones were isolated by selecting for spectinomycin resistance (50 μg/ml) on Luria agar by standard techniques. Clones containing the galactokinase gene were identified by their ability to confer on a galK-host strain the ability to ferment galactose as visualized by their red color on galactose MaConkey agar (Becton Dickson, Difco Division, Franklin Lakes, N.J.). One such isolate (pMODGAL-SPEC) was further characterized by restriction analysis to determine the relative orientation of the cloned pieces. The resultant Gal-Spec cassette is given in FIG. 18. The 4.5 Kb Gal-Spec cassette-containing Pvu II fragment from pMOD-GALSPEC was been used successfully for construction of target vectors by introduction of the cassette into target sequences. The target sequence insertion method utilized herein was in vitro transposition is described in the following section.

6.2.4 Production of Target Vectors: Transposition pf Gal-spec Cassette into Target Sequences Insertions into the target gene encoding the *B. subtilis* subtilisin were made into a pGPG6 derivative carrying the *B.* subtilis subtilisin apr gene. This derivative was made by first cloning the gene into a pGEM derivative using a T/A (Clark, 1988, Nucl. Acids Res. 16:9677–86) cloning strategy (Promega; Madison Wis., pGEM easy T vector) according to the vendor's protocols following PCR amplification from the strain 1A685 (BGSC Department of Biochemistry, The Ohio State University, Columbus, Ohio) using the *B. subtilis* subtilisin Forward and Reverse Primers (SEQ ID NOS. 11 and 12). This product was then (re)cloned as an EcoR I fragment into pGPG6 using standard molecular biology techniques to produce pGPG6-sub.

To perform the transposition, the 4.5 KB Pvu II fragment with the Gal-Spec cassette flanked by the inverted 19 base pair repeats of Tn5 was purified (from the plasmid pMOD-GALSPEC; see Section 6.2.3 above) and mixed with equal molar quantities of pGPG6-sub (paragraph above) in the presence of transposase according to the vendors (EZ::TN transposase kit; Epicentre; Madison, Wis.) directions. The resultant mixture was electroporated into OTG24 and then plated on Luria plates selecting spectinomycin (50 µg/ml) according to standard procedures.

Plasmid DNAs from spectinomycin resistant (and gentamycin 10 µg/ml; pGPG6 marker) isolates represent target vectors, i.e., vectors comprising target sequences into which the selectable marker cassette (which includes a negatively selectable marker) has been inserted. Target vector sequences were screened for the approximate location of the cassette insert by restriction analysis. Those located within the central 600 bp region of interest (see Section 6.1.2) were sequenced to determine the precise location of the inserts. Among those two, GS10 and GS2, were subsequently used in the DGA process, as described below. FIG. 20 shows the plasmid pGPG6-sub with position of the inserts indicated. GS10 and GS2 were used in the DGA allele re-assortment process following DGA mediated transfer to the target plasmid pWHsub (see 6.5.3; below).

It is noted that while these plasmids are, indeed, target vectors, as the term is described herein, the plasmids can also be utilized as donor vectors. For example, once the selectable marker cassette is introduced into a position of interest, DGA procedures can transfer the portion of the target gene carrying the marker cassette of interest to a homologous target gene sequence present on a target vector by using the vector above as the donor vector in the DGA process.

6.2.5 Production of Target Vectors: Direct Cloning of Selectable Marker Cassettes into Target Sequences Described in this section is the construction of target vectors by insertion of a selectable marker cassette into a target gene sequence via direct cloning methods.

To allow the direct cloning of selectable marker cassettes into target DNA sequences of pWHLic and pWHSub, extraneous sequences were deleted from the vectors to reduce them from 9 KB to approximately 3.8 KB in size. This reduction in plasmid size establishes a number of restriction enzymes sites within the target gene sequences as unique sites in these derivatives, thus allowing the direct cloning of the selectable marker cassette (including a negatively selectable marker) and otherwise facilitates their manipulation.

Deletion was accomplished by restriction enzyme-based deletion of the *B. subtilis* selectable (tetracycline resistance) marker and the *B. subtilis* replication origin. pWHLic and pWHSub were digested (separately) with Spe I and Aat II, filling-in with T4 DNA polymerase and subsequent DNA ligation was used to re-circularize the molecule according standard procedures. The resulting vectors, pLIBsub and pLIBlic, were confirmed by a series of restriction nuclease digests and are shown in FIG. 19.

pLIBLic has unique Nde I and BsrG I sites in the central subtilisin region of interest. To produce suitable target vectors in the *lichenformis* gene the plasmid pRL250 was cut with BamH I to produce a 2.3 KB fragment containing the npt I (kanamycin resistance) and sacB (sucrase; sucrose sensitivity) cassette (Kan-Suc). The nucleotide extensions on this fragment were filled-in using T4 DNA polymerase and then ligated into Nde I or BsrG I (separately)-digested pLIBLic preparations, which had been similarly filled in. The resultant ligation mixtures were transformed into OTG 197 selecting kanamycin resistance (40 µg/ml on Luria agar). The structure of the resultant plasmids, pLIBLic-Nde and pLIB-Lic-BsrG, was confirmed by restriction analysis. pLIBLic is illustrated in FIG. 19 with the unique Nde I or BsrG I shown.

6.3 Strains for the Growth and Manipulation of pGPG-derived Target and Donor Vectors Table 1 below describes bacterial strains employed in the generation and use of target and donor vectors derived from pGPG plasmids.

TABLE 1

| Strain | Genotype |
| --- | --- |
| OTG 2 | ΔlacX74 galE galK thi rpsL ΔphoA |
| OTG 24 | DE3(lac) uidA (ΔMluI)::pir(wt) |
| OTG 27 | endA hsdR pro supF/pRK2013::Tn9 |
| OTG 82 | ΔlacX74 galE galK thi rpsL ΔphoA mutL218::Tn10 |
| OTG 83 | ΔlacX74 galE galK thi rpsL ΔphoA zei::Tn10 |
| OTG 197 | DE3(lac) uidA (ΔMluI)::pir(wt)/pRK2013::Tn9 |

The galactose resistance selection requires a strain with a defect in both the galactose kinase gene (galK) and a defect in the galactose epimerase gene (galE). In such a strain, expression of GalK from the Gal-Spec cassette (described in Section 6.2.3) is lethal in the presence of galactose and selection for growth in the presence of galactose is a selection for loss of the cassette. The bacterial strain OTG2 (also known as KS272; Dr. Stanley Maloy, *salmonella*.life.uiuc.edu/strainfinder- .html) has defective galK and galE genes.

The genetic background of OTG2 was modified to include a tetracycline resistance element suitable for selection against donor strains that do not have the tetracycline resistance element. To accomplish this, bacteriophage P1 was grown on RFM 101 (Menzel and Gellert, 1987, Proc. Nat'l Acad. Sci. U.S.A. 84(12):4185–9; zei::Tn10) and CSG 7050 (Singer et al., 1989, Microbiol Rev 53(1):1–24; mutL218::Tn10) and used to transduce OTG 2 to growth on tetracycline-containing media (Luria Agar plus 25 µg/ml tetracycline) to produce OTG82 and 83, respectively. The mutL218 of OTG 82 abolishes mismatch repair. Due to the loss of mismatch repair function, the rate variant production via recombination between less homologous sequences using the procedures described herein is increased.

The use of the pGP704 derivatives as a donor of DNA requires transacting π replication functions, and for conjugative transfer, a mobilizing element. Strains supporting the growth of the plasmids and directing conjugal transfer are well known. Among these are strains OTG 24 (see Metcalf et al., 1994, Gene 138:1–7) and OTG 27 (see Ely B. 1985 Mol Gen Genet 200:302–4). The strain OTG197 was constructed from these strains by conjugal transfer of pRK2013::Tn9 (from OTG 27) into OTG24 on minimal media plates containing 40 mg/ml chloramphenicol. OTG197 was used in all mating experiments below to transfer donor vectors into target cells for variant formation (see Section 6.4).

6.4 Co-integrant Formation

The experiments described in this section demonstrate successful use of the first step of a two-step variant selection using the DGA methods of the invention. For ease of discussion, this first step is referred to herein as co-integrant formation. Use of the term, however, as discussed above, is not intended to bind the subject matter of the invention to a particular theory or mechanism.

In the crosses described below (Table 2), two different target cell strains were used: OTG82 (ΔlacX74 galE galK thi rpsL ΔphoA mutL::TN10) and OTG83 (ΔlacX74 galE galK thi rpsL ΔphoA zei::Tn10) to host the target vectors. Both target strains were transformed with the negatively selectable target plasmid pWHsub-GS2 that was formed by DGA recombination (see Section 6.5.3 below). A set of donor plasmids containing the DNA encoding the central 200 amino acids of the apr gene from different wild type variants (cloned into the EcoR I site of pGPG7; see Section 6.1.2) were used in the crosses. To form co-integrants donor strains with the designated pGPG7 derivatives in the genetic background of OTG197 were grown selectively (plus gentamycin 10 μg/ml, 40 μg/ml chloramphenicol) overnight from isolated single colonies in liquid Luria broth. Target strains were grown selectively in Luria Broth with ampicillin (100 μg/ml) in OTG82 or OTG83.

To perform the crosses, 5 microliters of donor were spotted on the surface of a Luria broth plate together with 5 microliters of target. After the 10 microliter spot dried into the plate (10–30 minutes), the mating mixtures were transferred to an incubator at 37° C. for 4–6 hours. At the end of this incubation interval the patch was transferred with a sterile applicator stick to 200 microliters of Luria broth in the well of a microtiter plate. This 200 microliter aliquot was thoroughly mixed to resuspend the cells and 10 microliters were spotted and spread on a Luria broth plate with 10 μg/ml gentamycin (to select for the pGPG replicon) and 15 μg/ml tetracycline (to select for against the pGPG harboring host strain derived from OTG97). These plates were incubated overnight (14–16 hours) and the number of colonies growing from the various crosses and control (donor and target alone) were scored. The results are tabulated in Table 2:

TABLE 2

| Donor Sequence | Colonies Mut+ Target | Colonies Mut− Target | Colonies Donor Alone | A.A. Differences Relative to Target |
|---|---|---|---|---|
| 3A1 | 58 | 124 | 0 | none |
| 3A3 | 112 | 237 | 0 | 1 |
| 3A6 | 132 | 215 | 0 | 1 |
| 3A7 | 4 | 17 | 0 | 24 |
| 3A11 | 14 | 212 | 0 | 5 |
| 3A13 | 4 | 48 | 0 | 15 |
| 3A14 | 2 | 18 | 0 | 25 |
| None (pGPG7) | 2 | 12 | 0 | N/A |

The results show that co-integrant formation in the Mut-plus strain was significantly above background when five or fewer differences exist (out of 200) amino acids. In the Mut-defective background this was extended to 15 differences. For the various strains listed, the nucleotide changes noted were approximately 3 times those seen at the amino acid level as numerous silent mutations were seen. The placement of a large insert with DGA (see Section 6.5.3, which describes a donor sequence containing a selectable marker cassette) demonstrated that large segments with no homology can be recombined into foreign sequences provided sufficient flanking homology exists.

Eight colonies from each of the crosses with the Mut-defective host were selectively purified by isolating single colonies of agar media (10 μg/ml gentamycin and 15 μg/ml tetracycline) for subsequent Gal-resistance mediated co-integrant resolution (Section 6.5.1). Following purification, the clones were grown (selectively) in liquid and then frozen with 10% glycerol as a cryo-preservative. Such frozen cultures can be used as a source of resolvable co-integrants at a later date. Failure to purify and grow selectively leads to large-scale segregation (>50% gentamycin negative) of the donor plasmid sequences.

Results from a second set of co-integrant forming crosses are shown in Table 3 below. The targets in this set are the Kan-Sac insertions (pLIBLic-Nde and pLIB-Lic-BsrG) described above (Section 6.2.5) transformed into the, OTG82 mutS::TN10 host, and results were identical with both inserts. Donors were clones of the core 200 amino acid encoding sequence from a set of various wild type lichenformis subtilisins as described in Section 6.1.2. Procedures employed were identical to those described above for the B. subtilis subtilisin donors and pWHsub-GS2.

TABLE 3

| Donor Sequence | Colonies Mut− Target | Colonies Donor Alone | A.A. Differences Relative to Target |
|---|---|---|---|
| 5A2 | >500 | 0 | 9 |
| 5A20 | >500 | 0 | 8 |
| 5A30 | >500 | 0 | 7 |
| 5A36 | >500 | 0 | 0 |
| (none) pGPG7 | 20 | 0 | N/A |

These results are consistent with those in Table 2. The presence of homology dramatically stimulated the formation of gentamycin resistant colonies. Based on the numbers above >95% of the gentamycin resistant colonies observed could be attributed to the presence of a shared regions of homology with typical wild type variant sequences. Small microscopic background gentamycin resistant colonies appeared on all plates, which can be attributed to spontaneous events occurring in the target strain as these colonies were also seen in target alone controls. Such colonies were readily distinguishable from the large true co-integrants.

6.5 Co-integrant Resolution

The experiments described in this section demonstrate successful use of the second step of a two-step variant selection using the DGA methods of the invention. In particular, following section describes phenotypic selection for the DGA-directed resolution of co-integrant based on the lethality of galactose (Section 6.5.1), as described in Section 5.1.2.1.1. For ease of discussion, this second step is referred to herein as co-integrant resolution. Use of the term, however, as discussed above, is not intended to bind the subject matter of the invention to a particular theory or mechanism.

6.5.1 Gal-based Resolution

Eight co-integrants each from the crosses summarized in Table 2 were streaked for single colonies (from cultures cryo-preserved in 10% glycerol; described in Section 6.4))

on Luria broth plates with ampicillin (100 µg/ml), spectinomycin (50 µg/ml) and gentamycin (10 µg/ml). Single colonies were inoculated into Luria broth liquid (without drug) and incubated overnight at 37° C. with gyratory shaking. Ten microliters (each) from these cultures were spread on a MacConkey Agar (base; Becton Dickson, Difco Division, Franklin Lakes, N.J.) plated with 2% galactose and 100 µg/ml ampicillin. Following overnight growth three types of galactose-resistant colonies appeared on the agar surface: red colonies (with various morphologies), white opaque colonies and white translucent colonies, in numbers varying from a few dozen to several hundred. Resolved co-integrants were among the white translucent colonies, and a single white colony was picked from each spot, and re-streaked for purification on the same MacConkey agar. These purified white colonies were tested for spectinomycin resistance (50 µg/ml) and gentamycin resistance (10 µg/ml). The resultant colony types are summarized below in Table 4 (Gent=gentamycin, Spec=spectinomycin, R=resistance, and S=sensitivity)

TABLE 4

| Original Donor Sequence | GentS, SpecS | GentR, SpecS | GentS, SpecR | GentR, SpecR |
|---|---|---|---|---|
| 3A1 | 8/8 | | | |
| 3A3 | 6/8 | | 2/8 | |
| 3A6 | 4/8 | | 2/8 | 2/8 |
| 3A7 | | | 3/8 | 5/8 |
| 3A11 | 5/8 | | 1/8 | 2/8 |
| 3A13 | 2/8 | | 5/8 | 1/8 |
| 3A14 | | | 5/8 | 3/8 |
| None (pGPG6) | | | 7/8 | 1/8 |

The phenotype consistent with the co-integrant resolving recombination is "GentS, SpecS." Such a phenotype indicates that the sequence that includes Spec is lost, as are the sequences associated with the Gent-conferring donor vector. Subsequent plasmid purification and restriction analysis demonstrated that this class of galactose resistant colony had a gross structure identical with that of pWHsub, demonstrating loss of the negatively selectable Gal-Spec insert.

Transformation of these plasmids into *B. subtilis* host 1A751 (double protease defect) demonstrated that they all produce active protease. DNA sequence analysis showed that they have, in most instances, inherited alleles from the donor plasmid. To further analyze the uptake of sequences from donor vectors, the two co-integrants from the 3A13 cross which gave rise to the GentS, SpecS galactose-resistant colonies were re-plated and eight new GentS, SpecS galactose resistant colonies were isolated from each for DNA sequence analysis (see Section 6.6.2 below).

6.5.2 Molecular Selection

The following sections describe the use of molecular methods for selecting for variant target molecules. Section 6.5.2.1 describes digesting a population of DNA molecules subjected to DGA with an enzyme whose restriction site is present in the original target vector but absent from the variant target molecule produced by DGA. Thus, unrecombined target vectors are digested by the restriction enzyme and, because they are not linear, are not take up by new host cells, while variant molecules are not linearized by the enzyme and can be selected for by transformation and growth on selective media. Section 6.5.2.2 describes the use of PCR to identify variant target molecules that have lost negatively selectable marker sequences in the selection process.

6.5.2.1 Restriction Enzyme-based Resolution

The Kan-Suc insert in pWLIB-Lic-BsrG contains a unique Xho I restriction site not present in pWHLIB-Lic. According to the strategy above such a site should work to select DGA-directed recombinant molecules (strategy diagramed in FIG. 21). Co-integrants of pGPG7–5A20 (Section 6.1.2) were formed with pWLIB-Lic-BsrG (Section 6.2.5) according procedures described above for the *B. subtilis* subtilisin crosses (Section 6.4). A collection of approximately 500 gentamycin and tetracycline resistant colonies was pooled and plasmid DNA was prepared according to standard procedures. This DNA was digested overnight with excess Xho I according to the vendor's recommendations (New England BioLabs, Beverly, Mass.). The Xho I-digested DNA preparation was then further treated with phosphatase according to standard procedures and used to transform OTG82 selecting ampicillin (100 µg/ml) resistance on Luria Broth agar plates with 5% sucrose. Twenty-six of these colonies were further tested for gentamycin resistance (10 µg/ml; to test for the presence of donor sequences) and kanamycin resistance (40 µg/ml; to test for loss of the insert). Seventeen of the twenty-six had the correct phenotype and were digested with Kpn I and BamH I to test for the presence the apr sequences (less the insert). All clones proved to be correct. The central 600 base pair region of the subtilisin gene was sequenced in these recombinant clones. The results are shown below in Section 6.6.1, and demonstrate that several variant subtilisin coding regions were generated, each of which encoded a variant subtilisin polypeptide exhibiting protease activity.

6.5.2.2 PCR-based Selection

To test the PCR selection strategy, co-integrants were formed as described in Section 6.4 (Table 2) with pGPG7 donor plasmids with the 3A1, 3A7, 3A11 gene sequences and pGPG7 alone. Gentamycin and Tetracycline selected colonies from these crosses were pooled (about 500 colonies each, separately) and DNA prepared according to standard procedures. This DNA, along with control DNA from pWH-Sub, was used as substrates for PCR reactions (29 cycles; 1 min. 93° C., 1.5 min. 57° C., 1.5 min. 72° C.) employing the primers originally described for the isolation of the *B. subtilis* subtilisin coding sequences (see Section 6.2) Products from the PCR reaction were resolved using agar gel electrophoresis with a 0.8% gel employing standard conditions.

The gel-resolved products from this experiment and the strategy for the PCR selection are shown together in FIG. 22. The gel revealed that a PCR product with a size appropriate to the *B. subtilis* subtilisin coding sequences was seen for the unit length gene (pWHsub) but not the gene containing the insert pWHSub-GS2. The unit length product is also noted for pools of DNA derived from the co-integrants made from the 3A1 and 3A11 pGPG7 donors. Co-integrant resolution experiments based on phenotypic selection (galactose resistance) above (Table 4) show that properly resolved structures were readily isolated from 3A1 and 3A11.

6.5.3 DGA-based Sequence Insertion

Section 6.2.4 describes the isolation of Gal-Spec cassettes in the donor plasmid pGPG7-sub, giving rise to plasmids GS2 and GS10. Using such an insert-containing sequence in a donor vector allows the sequence containing the insert to be moved (repeatedly, if desired) into target vectors using DGA. This, therefore, represents an efficient way to create new target recombination modules.

A culture with the pGPG7sub-GS2 plasmid (host strain OTG24) was grown and mixed with a second culture containing the target pWHSub (host strain OTG83) and co-integrants were selected (gentamycin and tetracycline) as described above (Section 6.4).

Individual colonies were purified and the co-integrant structure was confirmed by noting the unselected co-inheritance of spectinomycin resistance and galactose sensitivity.

Two methods were used to isolate resolved structures. In one strategy co-integrants were grown non-selectively in Luria broth and plated for single colonies on agar media containing ampicillin (100 µg/ml) and spectinomycin (50 µg/ml). Plates with isolated single colonies were replica printed to a second agar plate containing ampicillin, spectinomycin, and gentamycin (10 µg/ml). Individual colonies that were ampicillin and spectinomycin resistant but gentamycin sensitive (a marker for the donor sequence) appeared at a frequency of 0.5%. Restriction analysis of these plasmids demonstrated the desired recombinant product.

In a second strategy a restriction enzyme-based molecular selection was employed to isolate the desired recombinants. To do so DNA was prepared from a pool of co-integrants by standard procedures and digested with the restriction enzyme BsrG I which cuts in the pGPG7 sequences but does not cut in the Gal-Spec insert, the coding sequences for subtilisin or the pWH1520 vector. This digestion result in making the co-integrant linear but leaving the desired resolved structure as a circle molecule. The digestion mixture was treated with phosphatase according to standard procedures and used to transform OTG83 selecting spectinomycin (50 µg/ml) resistance. Individual colonies (6) were purified and all proved to be ampicillin and spectinomycin resistant but gentamycin sensitive. Subsequent restriction nuclease analysis showed the expected DNA structure. Phenotypic tests demonstrated the desired galactose sensitive growth. One such colony was retained and used for the crosses described above in Section 6.4. The work required and reagents used to recover the desired resolved structure was substantially less when the molecular selection was applied; 100% of the colonies had the desired structure as opposed to 0.5% in the unselected screened sample.

The movement of the insert to a target cell is illustrated in FIG. 23. These steps show how DGA (with the molecular restriction nuclease-based selection) can be used to insert donor sequences into a stretch of homologous target DNA. In the example, extensive homology extending across the entire subtilisin encoding sequences was used. This homology could have been limited to confine the extent of the subtilisin-encoding sequences participating in the event. Thus, in addition to removal of DNA sequences by DGA (e.g., removal of negatively selectable markers from target vectors; see, e.g., Sections 6.4 and 6.5.1, supra), DGA can be used to insert DNA sequences into target modules. Combining removal and insertion can be used to introduce non-homologous sequences into a target gene, as illustrated in FIG. 9. The non-homologous sequences can, e.g., comprise a selectable marker, or a coding sequence intended to become part of the modified target gene.

6.6 Results

Sections 6.5.1 (3A13 by 3A1) and section 6.5.2.1 (5A20 by 5A36) describe the production of recombinant molecules by a galactose-based and molecular selection-based DGA, respectively. To further investigate the nature of these recombinants, 3 milliliter samples were grown up in Luria Broth with 100 µg/ml ampicillin and plasmid DNA was prepared according to standard procedures (Qiagen; 28159 Avenue Stanford, Valencia Calif.). The DNA sequences of the recombinant molecules were analyzed using Vector NTI software (Informax, 7600 Wisconsin Avenue, Suite #1100, Bethesda, Md.). Results from those analyses are discussed below.

6.6.1 5A20 by 5A36 Crosses

Of the seventeen DGA recombinants derived from the 5A20 by 5A36 cross (described in Section 6.5.2.1, supra), DNA sequence results were obtained for thirteen recombinants. The thirteen sequenced samples defined twelve unique molecules distinguished by re-assortments of the 30 DNA sequence differences between the 5A36 target and the 5A20 donor molecules. All re-assortments were simple rearrangements consisting of contiguous patches of 5A20 sequences replacing stretches of the 5A36 sequence as would be expected from a single double crossover event ensuing from the DGA selected recombination event. No mosaics suggesting multiple crossover events were noted. These DGA exchanges were executed in a mutL strain that precluded mismatch repair, which may give rise to apparent multiple crossover events. Above it was noted that mutL was required for effective co-integrant formation in instances of significant sequence divergence. It is possible that co-integrant structures could have been moved to a mismatch repair proficient strain where mosaics could be observed. In the absence of multiple crossover events, 465 unique molecules are possible from single crossover events between two molecules with 30 differences. The pooling of large numbers co-integrants and the subsequent molecular selection (by restriction digestion) is an effective method of obtaining a random collection of recombinant molecules, which in the instant example yielded 12 out of 13 unique sequences.

To analyze proteins produced from these molecules, the predicted protein sequences were determined by in silico translation (Vector NTI). The resulting coding sequences were aligned, showing that the 12 variants produced represent seven different variant proteins. That is, some DNA variants produced encode the same variant protein. These results also demonstrate that co-integrant selection leads to a family of sequence variants once the co-integrant is resolved.

6.6.2 3A13 by 3A1 Crosses

The sequences of fifteen galactose-resistance-selected recombinants from the 3A13 by 3A1 cross (described in Section 6.5.1 above) were obtained. To analyze the proteins produced from these molecules the predicted protein sequence was determined by in silico translation (Vector NTI). The results showed that seven different variant proteins were produced. As above, therefore, some of the DNA variants produced encode the same variant protein. As also shown, these results further demonstrate that co-integrant selection leads to a family of variants upon co-integrant resolution.

Finally, each of the products encoded by the sequence variants produced by DGA in both crosses (including those for which sequence was not determined) demonstrated functional protease activity by the casein-agar test following introduction into a B. subtilis host. DGA selection is a highly effective way to obtain novel re-assorted structures.

6.6.3 Conclusion

The results described herein demonstrate the successful use to DGA to generate subtilisin variants using the techniques described in Section 5.2 above. Not only was a very high yield of nucleic acid variants generated, these nucleic sequences encoded a variety of subtilisin variant polypeptides, all of which exhibited subtilisin protease activity. Thus, the present invention provides methods of generating variant polypeptides in a more directed, efficient and cost-effective manner than the presently available methods of directed evolution.

The invention described and claimed herein is not to be limited in scope by the specific embodiments herein disclosed since these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. Throughout this application various references are cited, the contents of each of which is hereby incorporated by reference into the present application in its entirety for all purposes.

What is claimed is:

1. A method for generating a population of variant DNA molecules in bacterial cells, said method comprising:
   (a) transferring a donor vector into a bacterial cell capable of homologous recombination, wherein
      (i) said donor vector comprises a donor recombination module comprising, in the following order from 5' to 3': a first donor DNA sequence and a second donor DNA sequence, and
      (ii) said bacterial cell comprises a target vector comprising a target recombination module comprising, in the following order from 5' to 3': a first target DNA sequence; a negatively selectable marker; and a second target DNA sequence,
   wherein said first donor DNA sequence is homologous to said first target DNA sequence, and said second donor DNA sequence is homologous to said second target DNA sequence, wherein at least one of (1) the first donor DNA sequence and the first target DNA sequence are not identical to each other, or (2) the second donor DNA sequence and the second target DNA sequence, are not identical to each other; and
   (b) selecting for a population of bacterial cells within which homologous recombination between the donor vector and the target vector has occurred, such that the cells do not contain the negatively selectable marker, thereby generating a population of variant DNA molecules in bacterial cells.

2. The method of claim 1, wherein the donor vector further comprises a conjugative transfer sequence.

3. The method of claim 2, wherein the donor vector is transferred by conjugative transfer.

4. The method of claim 1, wherein the donor vector is transformed into the bacterial cell.

5. The method of claim 3 or 4, wherein the donor vector is a suicide vector.

6. The method of claim 1, wherein the target vector is integrated into the bacterial cell genome.

7. The method of claim 1, wherein the donor vector is transferred into the bacterial cell via a phage particle.

8. The method of claim 1, wherein the negatively selectable marker comprises a conditionally lethal sequence, and selecting for a population of bacterial cells in step (b) comprises selecting against said conditionally lethal sequence.

9. The method of claim 1, wherein: i) the target vector further comprises a reporter gene sequence downstream of the second target DNA sequence; ii) the negatively selectable marker is a polar insert sequence which prevents expression of the downstream reporter gene, such that the loss of said polar insert results in expression of the reporter gene; and iii) the step of selecting for a population of bacterial cells which do not contain the negatively selectable marker comprises selecting for expression of said reporter gene.

10. The method of claim 1, wherein the negatively selectable marker in the target recombination module comprises a unique restriction endonuclease recognition site.

11. The method of claim 1, wherein selecting for the population of bacterial cells which do not contain the selectable marker comprises amplifying DNA of the cells to determine whether the negatively selectable marker is absent from the cells.

12. The method of claim 1, in which the donor vector further comprises a positively selectable marker.

13. A method for generating a population of variant DNA molecules in bacterial cells, said method comprising:
(a) transferring a donor vector into a bacterial cell which is capable of homologous recombination, wherein:
  (i) said donor vector comprises a donor recombination module comprising, in the following order from 5' to 3': a first non-functional fragment of a selectable-marker; a first donor DNA sequence; and a second donor DNA sequence;
  (ii) said bacterial cell comprises a target vector comprising a target recombination module comprising, in the following order from 5' to 3': a second non-functional fragment of a selectable-marker; a first target DNA sequence; and a second target DNA sequence,
wherein said first donor DNA sequence is homologous to said first target DNA sequence, and said second donor DNA sequence is homologous to said second target DNA sequence, and recombination between said first non-functional fragment of a selectable-marker and said second non-functional fragment of a selectable-marker results in a functional selectable marker wherein at least one of (1) the first donor DNA sequence and the first target DNA sequence are not identical to each other, or (2) the second donor DNA sequence and the second target DNA sequence, are not identical to each other; and
(b) selecting for a population of bacterial cells within which homologous recombination between the donor vector and the target vector has occurred, such that the cells contain the functional selectable marker, thereby generating a population of a variant DNA molecules in bacterial cells.

14. The method of claim 13, wherein the donor vector is transferred by conjugative transfer.

15. The method of claim 13, wherein the donor vector is transformed into the bacterial cell.

16. The method of claim 14 or 15, wherein the donor vector is a suicide vector.

17. The method of claim 13, wherein the target vector is integrated into the bacterial cell genome.

18. The method of claim 13, wherein the donor vector is transferred into the bacterial cell via a phage particle.

19. The method of claim 13, in which the donor vector further comprises a positively selectable marker.

20. The method of claim 19, further comprising prior to step (b):
(c) selecting for a population of bacterial cells comprising the positively selectable marker of the donor vector.

21. The method of claim 1, further comprising:
(c) selecting said population of bacterial cells of step (b) for a desired phenotype.

22. A method for optimizing a phenotype comprising the method of claim 21, further comprising:
(d) repeating steps (a)–(c),
wherein the target recombination module used in step (d) is obtained from a bacterial cell selected in step (c).

23. The method of claim 1 or 13, in which the donor vector further comprises a third donor sequence, located 3' to the first donor sequence and 5' to the second donor DNA sequence.

24. The method of claim 23, wherein the third donor sequence comprises a negatively selectable marker.

25. The method of claim 22, in which the target recombination module of step (d) is identical to the target recombination module of step (a).

26. The method of claim 22, in which the target recombination module of step (d) is different from the target recombination module of step (a).

27. The method of claim 1, 13, or 22, further comprising, prior to step (a), the step of mutagenizing the donor vector.

28. The method of claim 21, further comprising, prior to step (a), the step of mutagenizing the donor vector.

29. The method of claim 27, wherein the step of mutagenizing the donor vector is carried out in vitro.

30. The method of claim 28, wherein the step of mutagenizing the donor vector is carried out in vitro.

31. The method of claim 27, wherein the step of mutagenizing the donor vector is carried out in vivo.

32. The method of claim 28, wherein the step of mutagenizing the donor vector is carried out in vivo.

33. The method of claim 1, 13, or 22, wherein the donor vector is a suicide vector.

34. The method of claim 21, wherein the donor vector is a suicide vector.

35. The method of claim 1, 13, or 22, wherein the bacterial cell is an *E. coli* cell.

36. The method of claim 21, wherein the bacterial cell is an *E. coli* cell.

37. The method of claim 13, further comprising:
(c) selecting said population of bacterial cells of step (b) for a desired phenotype.

38. A method for optimizing a phenotype comprising the method of claim 37, further comprising:
(d) repeating steps (a)–(c), wherein the target recombination module used in step (d) is obtained from a bacterial cell selected in step (c).

39. A method of claim 38, in which the target recombination module of step (d) is identical to the target recombination module of step (a).

40. The method of claim 38, in which the target recombination module of step (d) is different from the target recombination module of step (a).

41. The method of claim 38, further comprising, prior to step (a), the step of mutagenizing the donor vector.

42. The method of claim 37, further comprising, prior to step (a), the step of mutagenizing the donor vector.

43. The method of claim 41, wherein the step of mutagenizing the donor vector is carried out in vitro.

44. The method of claim 42, wherein the step of mutagenizing the donor vector is carried out in vitro.

45. The method of claim 41, wherein the step of mutagenizing the donor vector is carried out in vivo.

46. The method of claim 42, wherein the step of mutagenizing the donor vector is carried out in vivo.

47. The method of claim 38, wherein the donor vector is a suicide vector.

48. The method of claim 37, wherein the donor vector is a suicide vector.

49. The method of claim 38, wherein the bacterial cell is an *E. coli* cell.

50. The method of claim 37, wherein the bacterial cell is an *E. coli* cell.

51. The method of claim 12, further comprising prior to step (b):
 (c) selecting for a population of bacterial cells comprising the positively selectable marker of the donor vector.

52. The method of claim 13, wherein the donor vector further comprises a conjugative transfer sequence.

53. The method of claim 52, wherein the donor vector is transferred by conjugative transfer.

54. The method of claim 15 or 53, wherein the donor vector is a suicide vector.

* * * * *